United States Patent
McCairn et al.

(10) Patent No.: US 11,596,697 B2
(45) Date of Patent: Mar. 7, 2023

(54) NANOPARTICLE CONJUGATES

(71) Applicant: Chromition Limited, Stockport (GB)

(72) Inventors: Mark McCairn, Manchester (GB); Michael Turner, Manchester (GB); Benjamin Lidster, Manchester (GB)

(73) Assignee: Chromition Limited, Stockport (GB)

( * ) Notice: Subject to any disclaimer, the term of this patent is extended or adjusted under 35 U.S.C. 154(b) by 1162 days.

(21) Appl. No.: 16/070,712

(22) PCT Filed: Jan. 18, 2017

(86) PCT No.: PCT/EP2017/051014
§ 371 (c)(1),
(2) Date: Jul. 17, 2018

(87) PCT Pub. No.: WO2017/125456
PCT Pub. Date: Jul. 27, 2017

(65) Prior Publication Data
US 2019/0022248 A1   Jan. 24, 2019

(30) Foreign Application Priority Data

Jan. 19, 2016   (GB) ..................................... 1601004

(51) Int. Cl.
*A61K 9/00*   (2006.01)
*A61K 47/69*   (2017.01)
(Continued)

(52) U.S. Cl.
CPC ........ *A61K 47/6929* (2017.08); *A61K 47/558* (2017.08); *A61K 47/6898* (2017.08); *A61K 49/0054* (2013.01); *A61K 49/0093* (2013.01);

*C09K 11/06* (2013.01); *C09K 11/07* (2013.01); *B82Y 5/00* (2013.01); *C08G 2261/3142* (2013.01); *C09K 2211/1007* (2013.01); *C09K 2211/1029* (2013.01);
(Continued)

(58) Field of Classification Search
CPC .................................................. A61K 47/6929
See application file for complete search history.

(56) References Cited

U.S. PATENT DOCUMENTS 10,703,857 B2   7/2020   McCairn et al.
11,149,110 B2   10/2021   McCairn et al.
(Continued)

FOREIGN PATENT DOCUMENTS

CN   102627776 A   8/2012
WO   WO-2013/101902 A2   7/2013
(Continued)

OTHER PUBLICATIONS

Vusala et al., "Facile Synthesis of Cross-Linked Patchy Fluorescent Conjugated Polymer Nanoparticles by Click Reactions," Polym. Chem., 2:2818-2824 (2011).
(Continued)

*Primary Examiner* — Paul W Dickinson
(74) *Attorney, Agent, or Firm* — Foley Hoag LLP; David P. Halstead; Alexander J. Chatterley

(57) ABSTRACT

Conjugates comprising a drug, cell or biological molecule bound to a photoluminescent polymer nanoparticle, in particular a cross-linked polyfluorene nanoparticle, are described herein, as well as their methods of manufacture and their uses in biological imaging and sensing applications.

15 Claims, 15 Drawing Sheets

(51) Int. Cl.
*A61K 49/00* (2006.01)
*C09K 11/06* (2006.01)
*C09K 11/07* (2006.01)
*A61K 47/54* (2017.01)
*A61K 47/68* (2017.01)
*B82Y 5/00* (2011.01)

(52) U.S. Cl.
CPC ............ *C09K 2211/1416* (2013.01); *C09K 2211/1425* (2013.01); *C09K 2211/185* (2013.01)

(56) References Cited

U.S. PATENT DOCUMENTS

| | | |
|---|---|---|
| 2011/0068322 A1 | 3/2011 | Pickett et al. |
| 2014/0017130 A1 | 1/2014 | Trogler et al. |
| 2015/0270455 A1 | 9/2015 | Naasani et al. |
| 2016/0272884 A1 | 9/2016 | Kim et al. |

FOREIGN PATENT DOCUMENTS

| | | |
|---|---|---|
| WO | WO-2014/017983 A1 | 1/2014 |
| WO | WO-2015/052529 A1 | 4/2015 |
| WO | WO-2016/009231 A1 | 1/2016 |

OTHER PUBLICATIONS

Wu et al., "Synthesis and Characterization of Spiro-Linked Poly(terfluorene): a blue-emitting polymer with controlled conjugated length," Journal of Materials Chemistry, 12(1):2893-2897 (2002).
Behrendt et al., "Fluorescent nanoparticles from PEGylated polyfluorenes," Polymer Chemistry, 4: 1333-1336 (2013).
Behrendt et al., "Hybrid inorganic-organic composite nanoparticles from crosslinkable polyfluorenes," Journal of Materials Chemistry C, 1: 3297-3304 (2013).
Ekiz et al., "Synthesis and Characterization of Cross-Linked Waterdispersible conjugated polymer nanoparticles," Bilkent University: 89 pages (2012).
Marsitzky et al., "Amorphous Poly-2, 7-fluorene Networks," Chem. Mater., 13: 4285-4289 (2001).
Moon et al., "Organic Sol-Gel Synthesis of Microporous Molecular Networks Containing Spirobifluorene and Tetraphenylmethane Nodes," Journal of Polymer Science, Part A, Polymer Chemistry, 51: 1758-1766 (2013).
Park et al., "Pattern Formation of Silver Nanoparticles in 1-, 2-, and 3D Microstructures Fabricated by a Photo- and Thermal Reduction Method," Advanced Functional Materials, 20: 2296-2302 (2010).
Park et al., "White-Emitting Conjugated Polymer Nanoparticles with Cross-Linked Shell for Mechanical Stability and Controllable Photometric Properties in Color-Conversion LED Applications," ACS Nano, 5(4): 2483-2492 (2011).
Patra et al., "Fluoresecent nanoparticles based on a microporous organic polymer network: fabrication and efficient energy transfer to surface-bound dyes," ChemComm, 47: 9612-9614 (2011).
Schmidt et al., "Microporous Conjugated Poly(thienylene arylene) Network," Advanced Materials, 21: 702-705 (2009).
Sun et al., "Toward High Molecular Weight Triphenylamine-Based Hyperbranched Polymers," Macromolecules, 38: 2651-2658 (2005).
Wang et al., "Synthesis and Characterization of Highly Stable Blue-Light-Emitting Hyperbranced Conjugated Polymers," Journal of Polymer Science, Part A, Polymer Chemistry, 46: 790-802 (2008).
Xin et al., "Hyperbranced Oxadiazole-Containing Polyfluorenes: Toward Stable Blue Light PLEDS," Macromolecules, 38: 6755-6758 (2005).
Zhang et al., "Preparation of Chiral and Fluorescent Nanoparticles of Hyperbranched Conjugated Polymers by the Solvent Chirality Transfer Technology," College of Chemistry, Chemical Engineering and Materials Science, Soochow University, Suzhou 215123, 4: 426-435 (2013).
U.S. Appl. No. 16/070,778, Allowed.

NANOPARTICLE CONJUGATES

RELATED APPLICATIONS

This application is a § 371 national-stage application based on Patent Cooperation Treaty Application serial number PCT/EP2017/051014, filed Jan. 18, 2017, which claims the benefit of priority to United Kingdom Patent Application No. 1601004.3, filed on Jan. 19, 2016.

INTRODUCTION

The present invention relates to conjugates formed between photoluminescent nanoparticles and a drug molecule, biological molecule or cell. The present invention further relates to the methods of manufacture of these conjugates and to their use in biological imaging applications.

BACKGROUND OF THE INVENTION

Molecular dyes and Quantum Dots (QDs) have previously shown promise in a number of in vitro and in vivo bioimaging applications, where they can be internalized by cells, allowing individual organelles to be stained. However, their propensity for photooxidative degradation, which in the case of QDs can release toxic heavy metal species (e.g. cadmium and lead), ultimately precludes their use in humans or in long-term cell-tracking applications. Moreover, the use of such heavy metals is heavily restricted in certain territories, thereby underlining a need for less-toxic alternatives.

There is therefore a need for viable alternatives to molecular dyes and QDs for biological imaging applications, which are bright, stable, of high purity and are less toxic.

The present invention was devised with the foregoing in mind.

SUMMARY OF THE INVENTION

According to a first aspect of the present invention there is provided a conjugate comprising a drug molecule, biological molecule or cell bound to a photoluminescent polymer nanoparticle, wherein the drug molecule, biological molecule or cell is bound to the photoluminescent polymer nanoparticle by:
(i) a covalent bond formed by the reaction of functional groups present on the photoluminescent polymer nanoparticle with functional groups present on the drug molecule, biological molecule or cell;
(ii) the affinity pairing between a first moiety that is covalently attached to the photoluminescent polymer nanoparticle and a second moiety present on the drug molecule, biological molecule or cell;

and wherein the photoluminescent polymer nanoparticle is formed from a π-conjugated cross-linked polymer or a salt thereof, the π-conjugated cross-linked polymer comprising
a) 80-99.9 mol. % of π-conjugated monomers, and
b) 0.1-20 mol. % of a cross-linker having the formula I shown below:

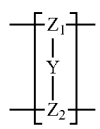

(I)

wherein
$Z_1$ and $Z_2$ are monomeric moieties, and
Y is absent, a bond, or a linking group; and
c) one or more functional groups (e.g. amino, carboxy, hydroxyl, halogen, vinyl, alkenyl, alkynyl, carbonyl or thiol groups) capable of reacting with functional groups on the drug molecule, biological molecule or cell to form a covalent bond linking the nanoparticle to the drug molecule, biological molecule or cell or a first moiety capable of affinity pairing with a second moiety present on the drug molecule, biological molecule or cell.

According to a second aspect of the invention there is provided an aqueous composition comprising a plurality of conjugates as defined herein dispersed within an aqueous medium.

According to a third aspect of the present invention, there is provided a method of forming a conjugate as defined herein, the method comprising the steps of:
(i) forming the nanoparticles by emulsion polymerisation, mini-emulsion polymerisation or dispersion polymerisation techniques to provide an aqueous suspension of nanoparticles; and
(ii) reacting and/or mixing the nanoparticles with the drug molecule, biological molecule or cell so as to form an aqueous suspension of the conjugate.

According to a fourth aspect of the present invention, there is provided a conjugate or an aqueous composition obtainable, obtained, or directly obtained, by a method defined herein.

According to a fifth aspect of the present invention, there is provided a use of a conjugate or aqueous composition defined herein in for biological imaging.

DETAILED DESCRIPTION OF THE INVENTION

Definitions

Unless otherwise stated, the following terms used in the specification and claims have the following meanings set out below.

References to "affinity pairing" or "affinity pairs" herein refer to a non-covalent interaction between a first moiety on the nanoparticle and a second moiety bound to the drug or biological molecule. The non-covalent binding between the moieties may be driven by one or more ionic, hydrophobic, van der Waals and/or hydrogen bonding interactions. The strength of the interaction needs to be sufficiently high to bind and hold the nanoparticle and drug or biological molecule together in biological fluids and cell culture media.

References herein to the "Stille reaction" (also known as Stille coupling) refer to a well-known chemical reaction coupling involving an organotin compound with an $sp^2$-hybridized organic halide catalyzed by palladium. The reaction is widely used in organic synthesis. The use of Stille polymerisation reactions for the production of conjugated polymer systems is described in, for example, Chem. Rev. 2011, 111, 1493-1528. The general reaction scheme is shown below:

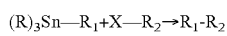

wherein
R is a hydrocarbyl substituent group, such as (1-6C)alkyl;
$R_1$ and $R_2$ are both monomeric units to be coupled; and
X is reactive group, typically a halide, such as Cl, Br, I, or a pseudohalide, such as a triflate, $CF_3SO_3^-$.

References to the "Suzuki reaction" refer to the well-known organic reaction of an aryl- or vinyl-boronic acid with an aryl- or vinyl-halide. Suzuki reactions are typically catalyzed by a palladium(0) complex catalyst. This reaction is well known in the chemical field and follows the general reaction scheme shown below:

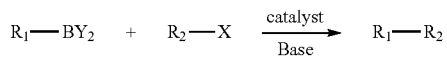

The reaction also works with pseudohalides, such as triflates (OTf), instead of halides. Boronic esters and organotrifluoroborate salts may be used instead of boronic acids. For polymer synthesis, $R_1$ and $R_2$ will represent monomeric units.

The term "hydrocarbyl" includes both straight and branched chain alkyl, alkenyl and alkynyl groups.

The term "alkylene" includes both straight and branched chain alkylene groups. References to individual alkylene groups such as "propylene" are specific for the straight chain version only and references to individual branched chain alkylene groups such as "isopropylene" are specific for the branched chain version only. For example, "(1-20C)alkylene" includes (1-14C)alkylene, (1-12C)alkylene, propylene, isopropylene and t-butylene. A similar convention applies to other radicals mentioned herein.

The terms "alkenylene" and "alkynylene" include both straight and branched chain alkenyl and alkynyl groups.

The term "aryl" is used herein to denote an aromatic carbocyclic ring system such as, for example, a phenyl, naphthalene, spirofluorene or anthracene ring. In an embodiment, an "aryl" is a phenyl, naphthalene or spirofluorene ring, and in particular it is phenyl or spirofluorene.

The term "heteroaryl" or "heteroaromatic" means an aromatic mono-, bi-, or tri-cyclic ring incorporating one or more (for example 1-4, particularly 1, 2 or 3) heteroatoms (for example N, O, P, S, Si, Ge, As or Se). Examples of heteroaryl groups are monocyclic, bicyclic and tricyclic groups containing from five to eighteen ring members. The heteroaryl group can be, for example, a 5- or 6-membered monocyclic ring, a 8-, 9- or 10-membered bicyclic ring or a 15-, 16-, 17- or 18-membered tricyclic ring. Suitably each ring in a bicyclic or tricyclic ring system comprises five or six ring atoms.

The term "cross-linked" used herein in relation to polymers does not encompass linear or hyperbranched polymers. The polymeric "branches" of hyperbranched polymers all emanate from a single focal point. In contrast, the polymeric strands of the cross-linked polymers forming part of the invention do not all converge to a single focal point. Rather, the strands of the cross-linked polymers forming part of the invention are randomly cross-linked to one another throughout polymer, with none of the cross-linking sites representing a single focal point in the sense of hyperbranched polymers. Furthermore, 4 or more polymeric chains emanate from a given cross-linking site within the polymers forming part of the invention, whereas the single focal point (or other branch points) within a hyperbranched polymer is only 3 coordinate. Moreover, the cross-linked polymers forming part of the invention are cross-linked to the extent that they are insoluble in all solvents (including aqueous, organic, polar and non-polar solvents), whereas hyperbranched polymers are commonly soluble.

The term "salt" used herein encompasses any suitable salt. Suitable salts include, but are not limited to, carboxylate salts (e.g. R—C(O)O$^-$M$^+$, wherein M$^+$ is a suitable cation, e.g. Na$^+$), ammonium salts (e.g. R—NH$_3^+$X$^-$, wherein X$^-$ is any suitable anion, e.g. Cl$^-$), alkoxides (e.g. R—O$^-$M$^+$, wherein M$^+$ is a suitable cation, e.g. Na$^+$), thiolates (e.g. R—S$^-$M$^+$, wherein M$^+$ is a suitable cation, e.g. Na$^+$), sulfates. (e.g. R—OSO$_2$O$^-$M$^+$, wherein M$^+$ is a suitable cation, e.g. Na$^+$), sulphites (e.g. R—SO$_2$O-M$^+$), phosphite (e.g. ROPO$_2$ONa) and zwitterionic salts (e.g. betaines).

The Conjugates of the Invention

As discussed hereinbefore, the present invention provides a conjugate comprising a drug molecule, biological molecule or cell bound to a photoluminescent polymer nanoparticle, wherein the drug molecule, biological molecule or cell is bound to the photoluminescent polymer nanoparticle by:
(i) a covalent bond formed by the reaction of functional groups present on the photoluminescent polymer nanoparticle with functional groups present on the drug molecule, biological molecule or cell;
(ii) the affinity pairing between a first moiety that is covalently attached to the photoluminescent polymer nanoparticle and a second moiety present on the drug molecule, biological molecule or cell;

and wherein the photoluminescent polymer nanoparticle is formed from a π-conjugated cross-linked polymer or a salt thereof, the π-conjugated cross-linked polymer comprising
a) 80-99.9 mol. % of π-conjugated monomers, and
b) 0.1-20 mol. % of a cross-linker having the formula I shown below:

wherein
$Z_1$ and $Z_2$ are monomeric moieties, and
Y is absent, a bond, or a linking group; and
c) one or more functional groups (e.g. amino, carboxy, hydroxyl, halogen, vinyl, alkenyl, alkynyl, carbonyl or thiol groups) capable of reacting with functional groups on the drug molecule, biological molecule or cell to form a covalent bond linking the nanoparticle to the drug molecule, biological molecule or cell or a first moiety capable of affinity pairing with a second moiety present on the drug molecule, biological molecule or cell.

As indicated above, in one embodiment the photoluminescent polymer nanoparticle comprises one or more functional groups that are capable of reacting with functional groups present on the drug molecule, biological molecule or cell to form a covalent linkage/bond between the nanoparticle and the drug molecule, biological molecule or cell. Any suitable covalent linkage would suffice. In an embodiment, the covalent linkage/bond is selected from an amide, disulphide, ether, thioether, amine, imine, enamine or ester linkage etc.

In an embodiment, the photoluminescent polymer nanoparticle is a photoluminescent π-conjugated polymer nanoparticle.

Suitably, the photoluminescent polymer nanoparticle comprises:
(i) one or more hydroxyl groups that are capable of reacting with carboxy groups present on the drug molecule, biological molecule or cell to form ester bonds that couple the polymeric nanoparticle to the drug molecule, biological molecule or cell;

(ii) one or more amino groups that can react with carboxy groups present on the drug molecule, biological molecule or cell to form amide bonds that couple the polymeric nanoparticle to the drug molecule, biological molecule or cell;

(iii) one or more carboxy groups that can react with amino groups present on the drug molecule, biological molecule or cell to form amide bonds that couple the polymeric nanoparticle to the drug molecule, biological molecule or cell;

(iv) one or more thiol groups that can react with thiol groups present on the drug molecule, biological molecule or cell to form disulphide bonds that couple the polymeric nanoparticle to the drug molecule, biological molecule or cell;

(v) one or more vinyl groups that can react with thiol groups present on the drug molecule, biological molecule or cell to form sulphide bonds that couple the polymeric nanoparticle to the drug molecule, biological molecule or cell; and/or (vi) one or more carbonyl groups that can react with amine groups present on the drug molecule, biological molecule or cell to form imine or enamine bonds that couple the polymeric nanoparticle to the drug molecule, biological molecule or cell.

Suitably, at least a proportion of the functional groups are present on the surface of the nanoparticle.

It will also be appreciated that the photoluminescent polymer nanoparticle may be bound to the drug molecule, biological molecule or cell by the affinity pairing/binding that can occur between certain moieties that can be covalently bound to nanoparticle and the drug molecule, biological molecule or cell to bind the nanoparticle to the drug molecule, biological molecule or cell. Thus, the photoluminescent polymer nanoparticle may have a first moiety covalently attached to it which binds with a high affinity to a second moiety present on the drug molecule, biological molecule or cell. For example, one of the first or second moieties that form the affinity pairing may be streptavidin and the other may be biotin, one may be an antibody and the other may be antigen, one may be an epitope and the other may be a paratope, one may be DNA, RNA or PNA strand and the other may be a complimentary DNA, PNA, or RNA strand, or one may be a drug and the other may be a receptor that the drug binds to. Thus, examples of suitable moieties that bind to one another with high affinity include streptavidin/biotin; DNA, RNA, or PNA with complimentary DNA, RNA or PNA, antibody/antigen, and perfluoroalkyl compounds.

In an embodiment, one of the first or second moieties that form the affinity pairing is streptavidin and the other is biotin. In a further embodiment, the first moiety bound to the photoluminescent polymer nanoparticle is a streptavidin molecule which binds with a high affinity to a second biotin moiety present on the drug molecule, biological molecule or cell. In another embodiment, the first moiety bound to the photoluminescent polymer nanoparticle is biotin which binds with high affinity to a second streptavidin moiety present on the drug molecule, biological molecule or cell.

In an embodiment, the photoluminescent polymer nanoparticle is bound to the drug molecule, biological molecule or cell by a covalent amide bond (formed by the reaction of a carboxy group present on the nanoparticle or the drug/biological molecule or cell with an amino group present on the other, or by the interaction between a streptavidin moiety present on one of the nanoparticle or the drug/biological molecule or cell with a biotin moiety present on the other.

In another embodiment, the photoluminescent polymer nanoparticle comprises one or more additional functional groups in addition to the functional group(s) used to conjugate the photoluminescent polymer nanoparticle to the drug molecule, biological molecule or cell. The one or more additional functional groups may serve to increase the hydrophilicity of the photoluminescent polymer nanoparticle. Hence, in an embodiment, the one or more additional functional groups may be hydrophilic. Suitable hydrophilic functional groups include —$OSO_3H$, or a suitable salt thereof (e.g. —$OSO_3Na$), —$SO_3H$ or a suitable salt thereof (e.g. —$SO_3Na$), —$[(CH_2)_2$—$O]_nH$ or a suitable terminal functionality thereof (e.g. —$[(CH_2)_2$—$O]_nMe$), —$[O$—$(CH_2)_2]_nOH$ or a suitable terminal functionality thereof (e.g. —$[O$—$(CH_2)_2]_nOMe$), —$[CH_2MeCH_2$—$O]_n$— or a suitable terminal functionality thereof (e.g. —$[CH_2MeCH_2$—$O]_n$-Me), —$[OCH_2MeCH_2]_n$— or a suitable terminal functionality thereof (e.g. —$[OCH_2MeCH_2]_n$-Me), phosphite —$OPO_2ONa$ and zwitterionic salts (e.g betaines).

The Photoluminescent Polymer Nanoparticle

As indicated above, the nanoparticle is formed from a π-conjugated cross-linked polymer or a salt thereof, the π-conjugated cross-linked polymer comprising
  a) 80-99.9 mol. % of π-conjugated monomers, and
  b) 0.1-20 mol. % of a cross-linker having the formula I shown below:

wherein $Z_1$ and $Z_2$ are monomeric moieties, and

Y is absent, a bond, or a linking group.

The nanoparticles utilised in the conjugates of the present invention offer a number of advantages when compared with the state of the art. Importantly, the nanoparticles are formed from π-conjugated cross-linked polymers. The π-conjugated cross-linked polymers themselves comprise a backbone of π-conjugated monomers, with cross-linking moieties interspersed along the π-conjugated backbone. The structure of the cross-linking moieties is such that one monomer spans two polymeric backbone chains. Therefore, during assembly of the polymer, the incorporation of the cross-linking moieties into the π-conjugated backbone chain provides a direct site for the propagation of a further π-conjugated backbone chain on both sides of the cross-linking moiety. Hence, the cross-links in the polymers forming the present nanoparticle compositions are formed in-situ during linking of the monomer units, meaning that the degree of cross-linking can be readily adjusted simply by varying the concentration of cross-linker. Owing to their π-conjugated structures, cross-linked polymers of this type provide good electron delocalisation properties. Such polymers also offer the possibility of electron delocalisation between adjacent backbone chain via the cross-linker. In contrast to this direct, in-situ formation of cross-links discussed above, prior art CPNs have focussed on the preparation of polymers formed from monomers having specially-modified pendant side chains that are amenable to cross-linking under certain conditions. Whilst being a viable method, such an approach necessarily requires the initial step of forming the polymer backbone chains prior to placing the backbone chains under suitable conditions to induce cross-linking between them. This multi-step approach is more complex than that used to prepare the polymers forming the present compositions, and the degree of cross-linking between the polymeric chains is notably more difficult to control.

Aside from manufacturing simplicity and tuneability, the π-conjugated cross-linked polymers forming part of the invention lend themselves to obtaining nanoparticle compositions exhibiting significantly higher levels of purity. The insoluble cross-linker renders the nanoparticle composition insoluble in water and organic solvents, such that the π-conjugated cross-linked polymers exhibit swelling when brought into contact with a solvating solvent. Swelling the polymers in this manner allows impurities trapped within the polymeric network, such as catalysts and other reagents, to be easily removed by washing. Unlike prior art compositions, the resulting high purity photoluminescent nanoparticle compositions are therefore highly suitable for use in biological applications, such as bioimaging, and other in vivo processes.

Having regard to formula I, $Z_1$ is able to polymerise with π-conjugated polymer and aromatic monomers so as to form a first polymeric chain. $Z_2$ is able to polymerise with π-conjugated polymer and aromatic monomers so as to form a second polymeric chain, adjacent to the first polymeric chain, thereby linking together two adjacent polymeric chains. Accordingly, $Z_1$ and $Z_2$ may independently be selected from any of the examples of the moieties forming part or all of the monomers that are defined herein. In an embodiment, $Z_1$ and $Z_2$ are π-conjugated. In another embodiment, $Z_1$ and $Z_2$ are aromatic.

Still having regard to formula I, it will be appreciated that $Z_1$ and/or $Z_2$ may have more than 2 covalent attachment points (for attaching to the π-conjugated monomers). For example $Z_1$ and/or $Z_2$ may have 3 covalent attachment points.

Still having regard to formula I, Y may be any suitable linker group, and may be π-conjugated or non-π-conjugated. Exemplary linker groups include an atom (e.g. O, S), a metal (e.g. Ir, Pt, Rh, Re, Ru, Os, Cr, Cu, Pd, Au) or other group (e.g. $-SiR_2-$, $-CH=CH-$, $-C_6H_4-$). When Y is a bond, it may be a single or double bond. When Y is absent, $Z_1$ is directly linked to $Z_2$, e.g. $Z_1$ is fused to $Z_2$ or is connected thereto by a common (shared) spiro carbon atom.

The cross-linker of formula (I) may take a variety of forms. In particular, Y may be absent, a bond, or a linking group.

Where Y is absent (and $Z_1$ and $Z_2$ are linked directly to each other), the cross-linker may have a structure according for formula (Ia) below:

(Ia)

Examples of such cross-linkers include, but are not limited to:

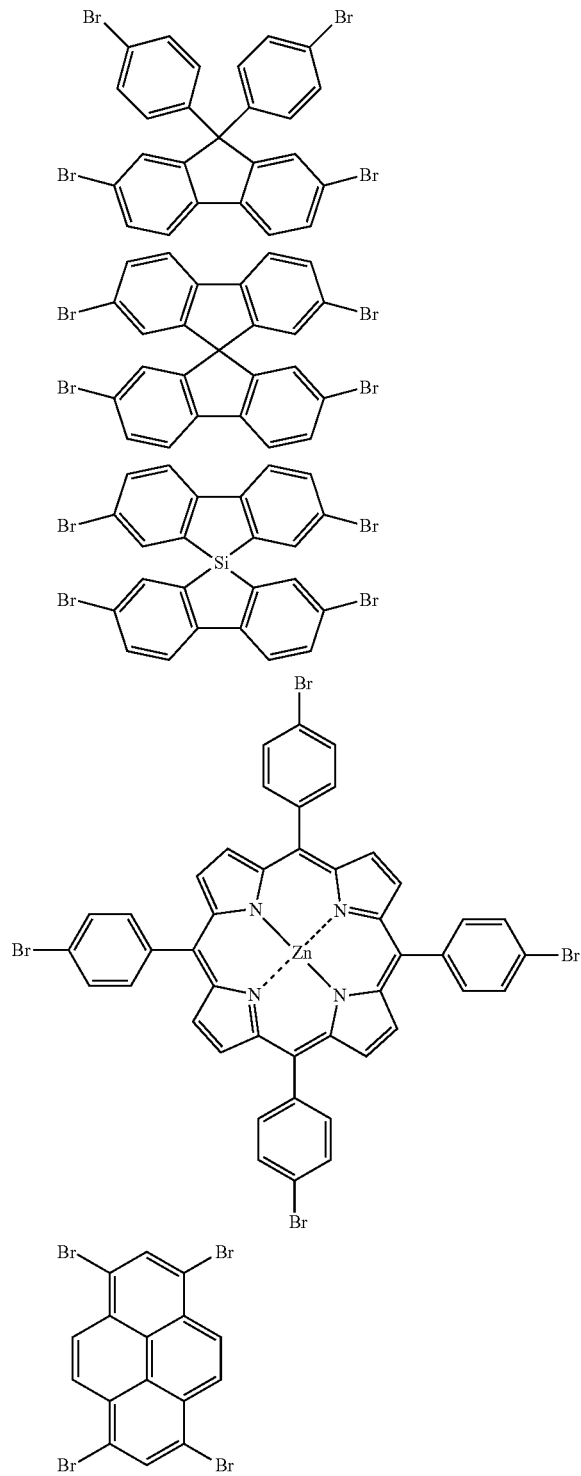

In such embodiments, $Z_1$ may be directly connected to $Z_2$ in the sense that $Z_1$ is fused to $Z_2$, or $Z_1$ and $Z_2$ share one or more common atoms.

Where Y is a bond (single or double), the cross-linker may have a structure according for formula (Ib) below:

(Ib)

Examples of such cross-linkers include, but are not limited to:

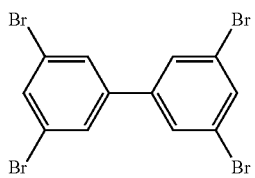

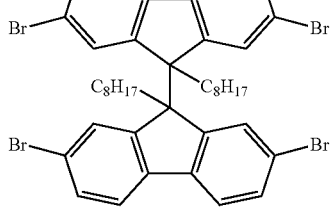

Where Y is a linking group, the linking group may be π-conjugated or non-π-conjugated. Examples of cross-linkers having π-conjugated linking groups include, but are not limited to:

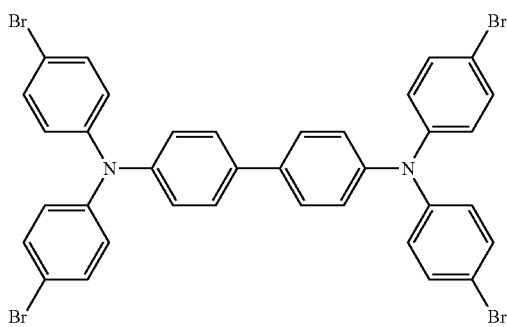 [SMILES: Brc1ccc(N(c2ccc(Br)cc2)c2ccc(-c3ccc(N(c4ccc(Br)cc4)c4ccc(Br)cc4)cc3)cc2)cc1]

Examples of cross-linkers having non-π-conjugated linking groups include, but are not limited to:

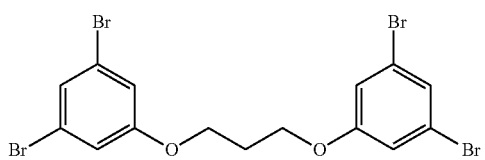

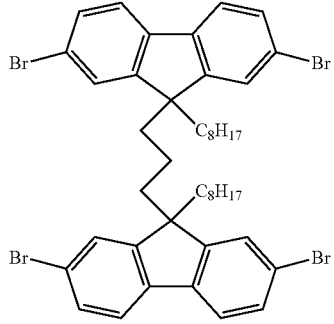

In certain embodiments, where Y is a linking group, the linking group may comprise additional monomeric moieties, $Z_n$. In such embodiments, Y may have a structure according to formula (A) below:

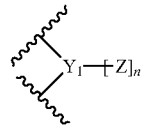
(A)

wherein $Y_1$ is a linking group as defined herein;
Z is a monomeric moiety and is as defined for $Z_1$ or $Z_2$ defined herein; and
n is 1 or more (e.g. 1 or 2).
In an embodiment, n is 1, and the cross-linker may have a structure according to formula (Ic) below:

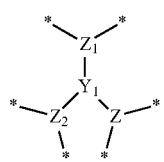
(Ic)

Where $Y_1$ is a π-conjugated linking group, exemplary cross-linkers of this type include, but are not limited to:

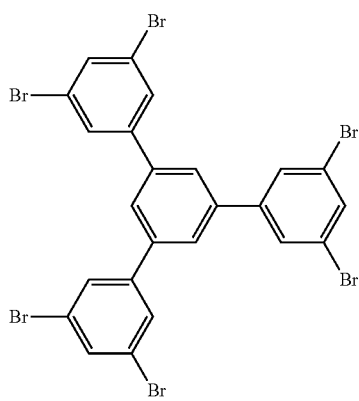 [SMILES: Brc1cc(Br)cc(-c2cc(-c3cc(Br)cc(Br)c3)cc(-c3cc(Br)cc(Br)c3)c2)c1]

Alternatively, where $Y_1$ is an atomic linking group, exemplary cross-linkers of this type include, but are not limited to:

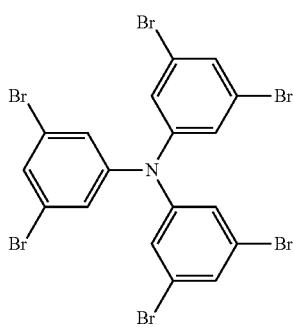

Alternatively, the cross-linker of formula (Ic) may have a different number of covalent attachment points (for attaching to the π-conjugated monomers). For example, the cross-linker may contain 5, 7, 8 or 9 covalent attachment points, as illustrated below:

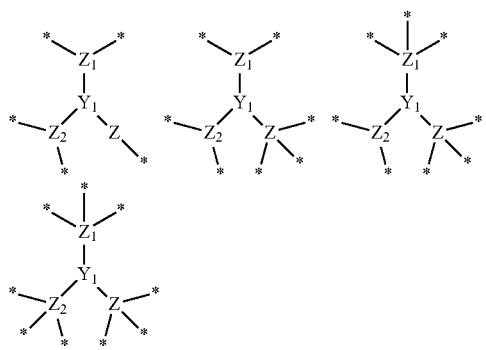

In another embodiment, each of monomeric moieties $Z_1$ and $Z_2$ may be bonded to Y by two separate bonds. Cross-linkers of this type may have a structure according to formula (Id) shown below:

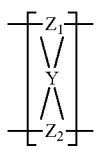

(Id)

In an embodiment, where Y is as defined in formula A, the cross-linker may have a structure according to formula (Id') below:

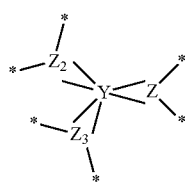

(Id')

wherein $Y_1$ is a linking group as defined herein; and Z is a monomeric moiety and is as defined for $Z_1$ or $Z_2$ defined herein.

Where $Y_1$ is an atomic linking group, exemplary cross-linkers of this type include, but are not limited to:

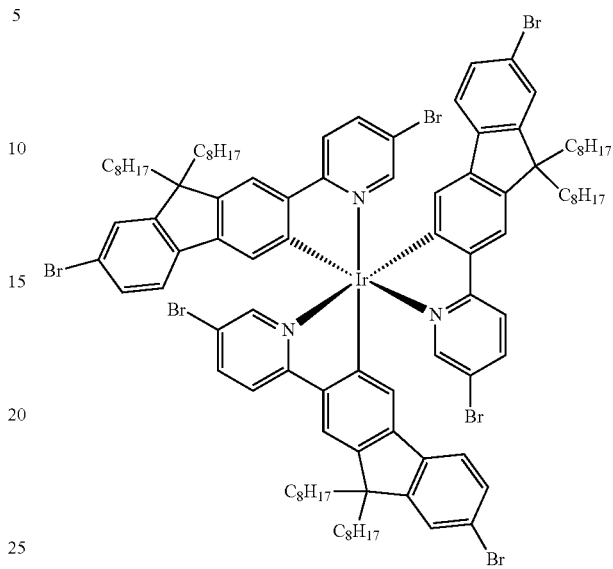

Alternatively, the cross-linker of formula (Id') may have a different number of covalent attachment points (for attaching to the π-conjugated monomers). For example, the cross-linker may contain 4 (wherein Z carries no covalent attachment points), 5, 7, 8 or 9 covalent attachment points.

In an embodiment, Y is as defined in formula (A) and n is 2. In such embodiments, the cross-linker may have a structure according to formula (Ie) below:

(Ie)

wherein $Y_1$ is a linking group as defined herein; and each Z is independently a monomeric moiety and is as defined for $Z_1$ or $Z_2$ defined herein.

Where $Y_1$ is a non-π-conjugated linking group, examples of such cross-linkers include, but are not limited to:

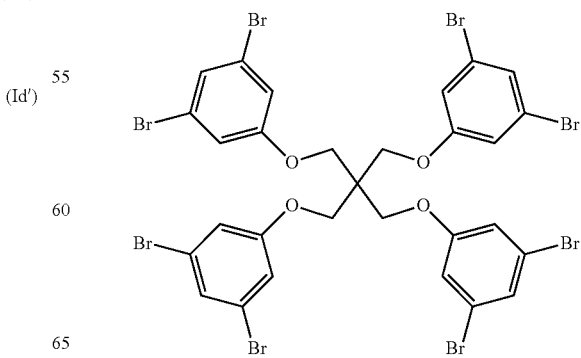

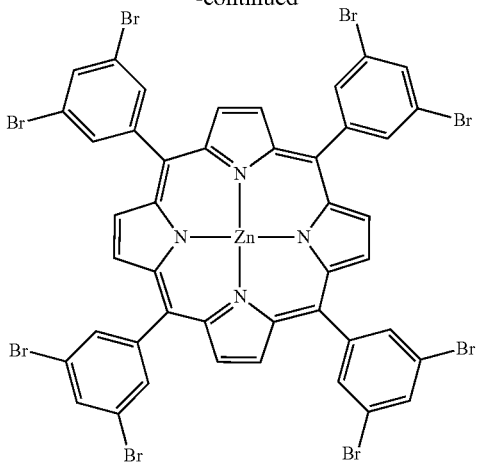

In an embodiment, the nanoparticles comprise identical cross-linkers, or a plurality of different cross-linkers.

In another embodiment, when Y is a linking group, said linking group does not comprise additional monomeric moieties Z. In such embodiments, $Z_1$ and $Z_2$ are the only monomeric moieties present within the cross-linker.

In another embodiment, the cross-linker has the formula II shown below:

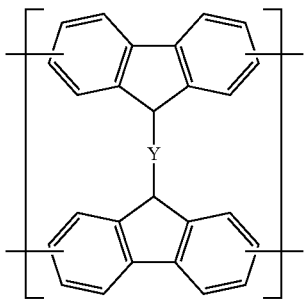

(II)

wherein

Y is absent, a bond, or a linking group.

In an embodiment, Y is absent, such that $Z_1$ is directly linked to $Z_2$, e.g. $Z_1$ is fused to $Z_2$ or is connected thereto by one or more common (shared) atoms (e.g. a spiro carbon atom). Suitably, $Z_1$ is connected to $Z_2$ by a common spiro carbon atom.

In another embodiment, the cross-linker has the formula III shown below:

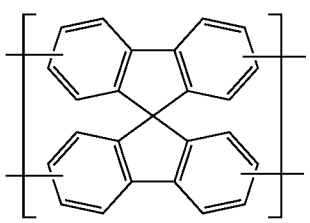

(III)

Suitably, the cross-linker has the following structure:

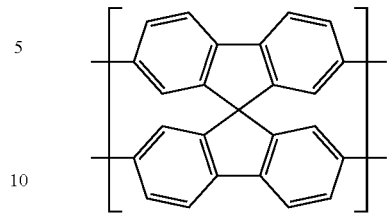

The nanoparticle composition comprises 80-99.9 mol. % of one or more π-conjugated monomers. Any suitable π-conjugated monomers capable of polymerising to form nanoparticles may be used.

In one embodiment, the π-conjugated polymers of the present invention do not comprise any carbon-carbon triple bonds. Thus, in one aspect, the present invention relates to π-conjugated cross-linked polymers that do not comprise any carbon-carbon triple bonds. The electrons in a carbon-carbon triple bond give rise to conformations in which the π-electrons are not fully delocalised.

It will be appreciated by those skilled in the art that the monomeric units used to form the cross-linked π-conjugated polymers may comprise a selection of different chemical moieties that either alone or in combination provide a monomer having a π-conjugated ring system.

It will also be appreciated by those skilled in the art that the π-conjugated polymer used to form the nanoparticles must further comprise one or more functional groups (e.g. amino, carboxy, hydroxyl, halogen, vinyl, alkenyl, alkynyl, carbonyl or thiol groups) that can be reacted with functional groups on the drug molecule, biological molecule or cell, or either a first moiety (e.g. streptavidin, biotin, antibody or a protein that can be bound by a second moiety antibody) capable of forming a non-covalent affinity pairing with a second moiety on the drug molecule, biological molecule or cell (e.g. biotin, streptavidin, antibody or protein capable of binding to a first moiety antibody) or a functional group capable of reaction to bind a first moiety once the polymer nanoparticle has been formed.

Examples of suitable π-conjugated ring systems that may be present in the monomer units, either alone or in any suitable combination, include mono-cyclic aryl groups (e.g. phenyl rings), polycyclic aryl ring systems (e.g. fluorene ring systems, naphthyl rings), mono-cyclic heteroaryl rings (e.g. thiophene rings) or polycyclic heteroaryl ring systems (e.g. benzothiazole, benzodiazathazole rings, thieno[3,2-b]thiophene, or pyrrolo[3,4-c]pyrrole) or other conjugated heterocyclic rings systems (e.g. pyrrolo-pyrrole-1,4-dione rings), and wherein each moiety is optionally substituted by one or more organic groups, e.g. hydrocarbyl substituent groups optionally comprising 1 to 30 carbon atoms and optionally comprising one or more heteroatoms (e.g. N, O, P, S, Si, Ge, As or Se), and, where two or more of such moieties are present, they may be linked together by a bond or via an atom linkage (e.g. such as in a bi-arylamine or tri-arylamine group), and with the proviso that at least one monomer has a substituent group which is, or which comprises, at least one functional group (e.g. amino, carboxy, hydroxyl, halogen, vinyl, alkenyl, alkynyl, carbonyl or thiol groups) or a first moiety (e.g. biotin, streptavidin, antibody or protein capable of binding to a second moiety antibody) as defined herein or a functional group capable of covalently binding to a first moiety (e.g. biotin or streptavidin) once the polymeric nanoparticle is formed.

Further examples of particular moieties that may form part or all of the π-conjugated monomers include any one of the following:
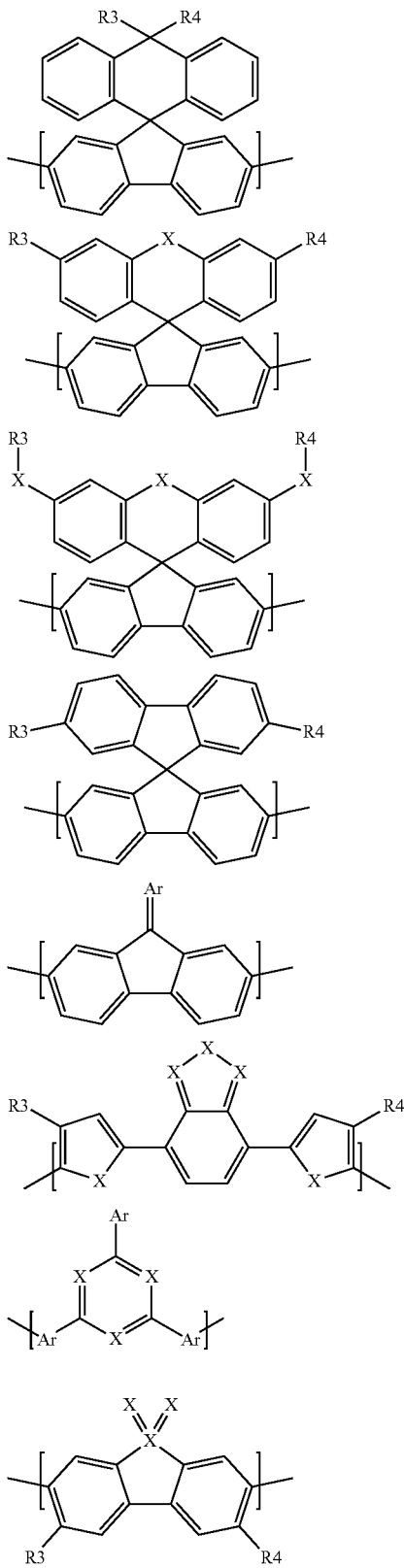
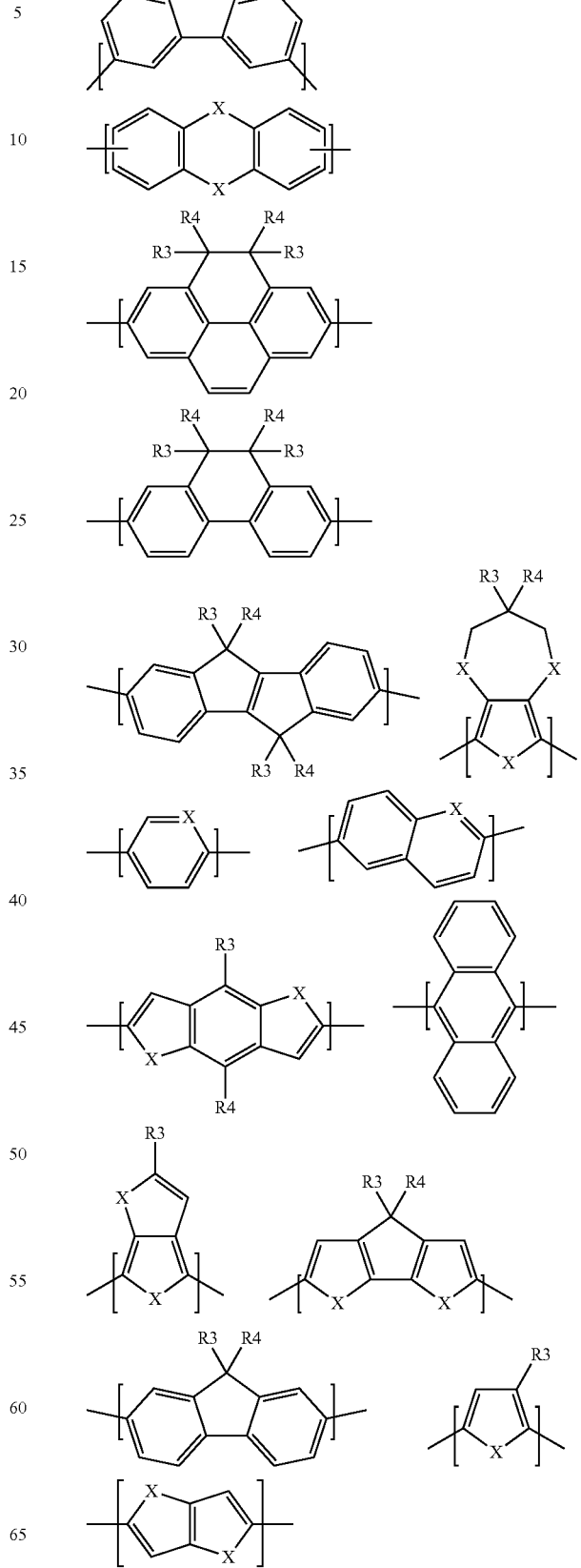

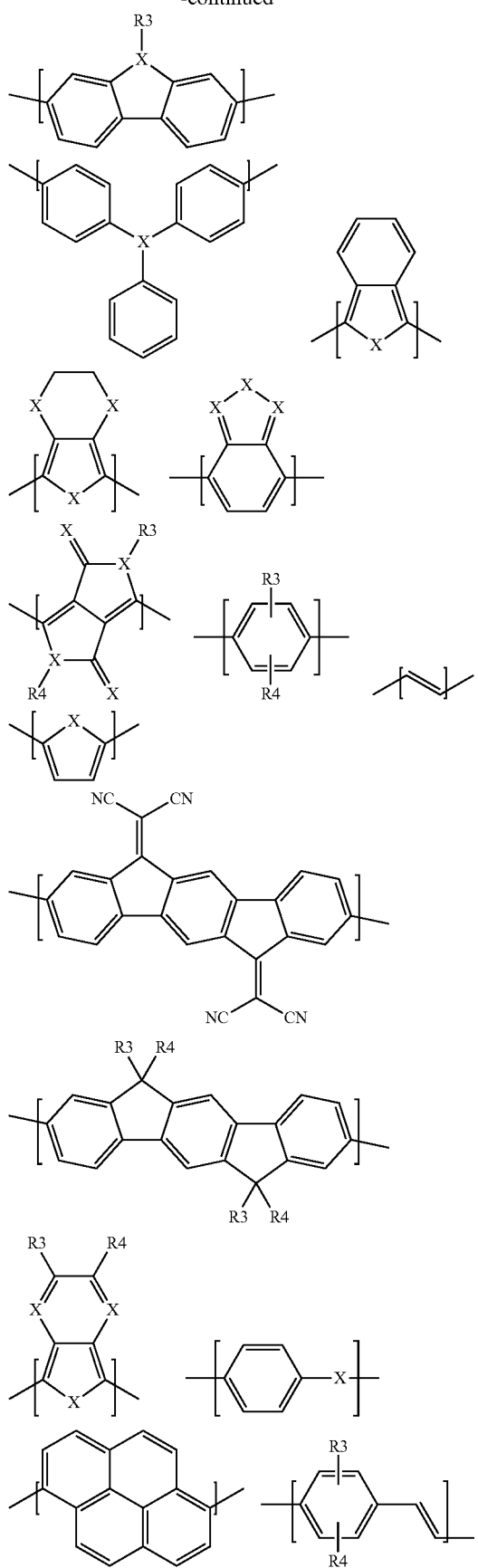
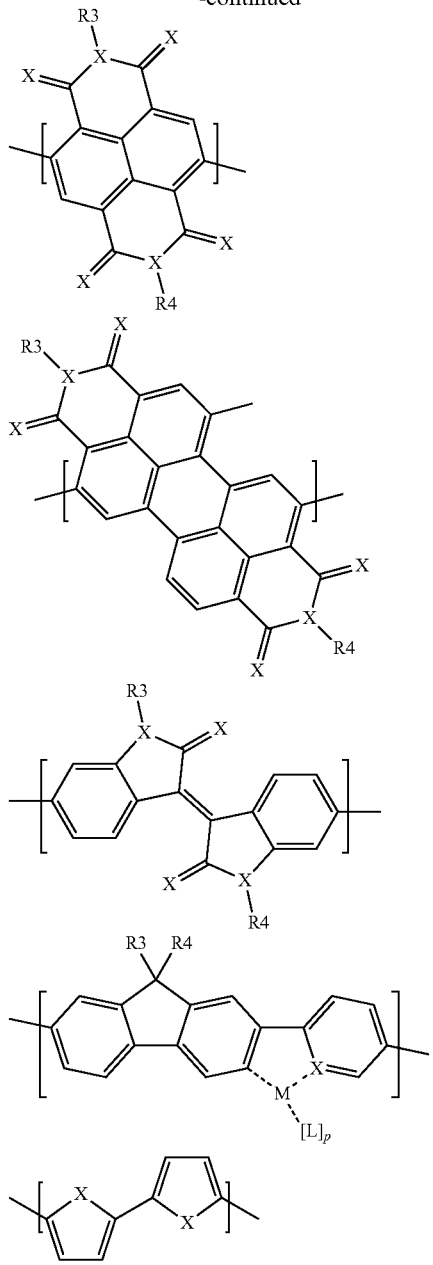

wherein

X is a heteroatom selected from N, O, P, S, Si, Ge, As or Se (especially N, O or S)

Ar is a cyclic or polycyclic group which is optionally a π-conjugated (e.g. fluorene);

$R_3$ and $R_4$ are each independently hydrogen or an organic substituent group (e.g. an optionally substituted hydrocarbyl substituent group optionally comprising 1 to 30 carbon atoms and optionally comprising one or more heteroatoms (e.g. N, O, P, S, Si, Ge, As or Se), or an optionally substituted aromatic or heteroaromatic group or a group $R_1$ or $R_2$ as defined herein);

M is a metal (e.g. Ir, Pt, Rh, Re, Ru, Os, Cr, Cu, Pd, or Au);

L is a ligand (e.g. a halide or a hydrocarbyl substituent group optionally comprising 1 to 30 carbon atoms and optionally comprising one or more heteroatoms (e.g. N, O, S, Si, or P) or an aromatic or hetroaromatic group);

and wherein each of the above structures is optionally further substituted with one or more organic substituent groups (e.g. a hydrocarbyl substituent groups optionally comprising 1 to 30 carbon atoms and optionally comprising one or more heteroatoms (e.g. N, O, P, S, Si, Ge, As or Se) or an aromatic or heteroaromatic group);

and with the proviso that at least one monomer has a substituent group which is, or which comprises, at least one functional group (e.g. amino, carboxy, hydroxyl, halogen, vinyl, alkenyl, alkynyl, carbonyl or thiol groups) or a first moiety (e.g. biotin or streptavidin) as defined herein or a functional group capable of covalently binding to a first moiety (e.g. biotin or streptavidin) once the polymeric nanoparticle is formed.

A particular example of the group >X(=X)$_2$ in the structures above is >SO$_2$.

In an embodiment, particular moieties that may form part or all of the π-conjugated monomers include any one of the following:

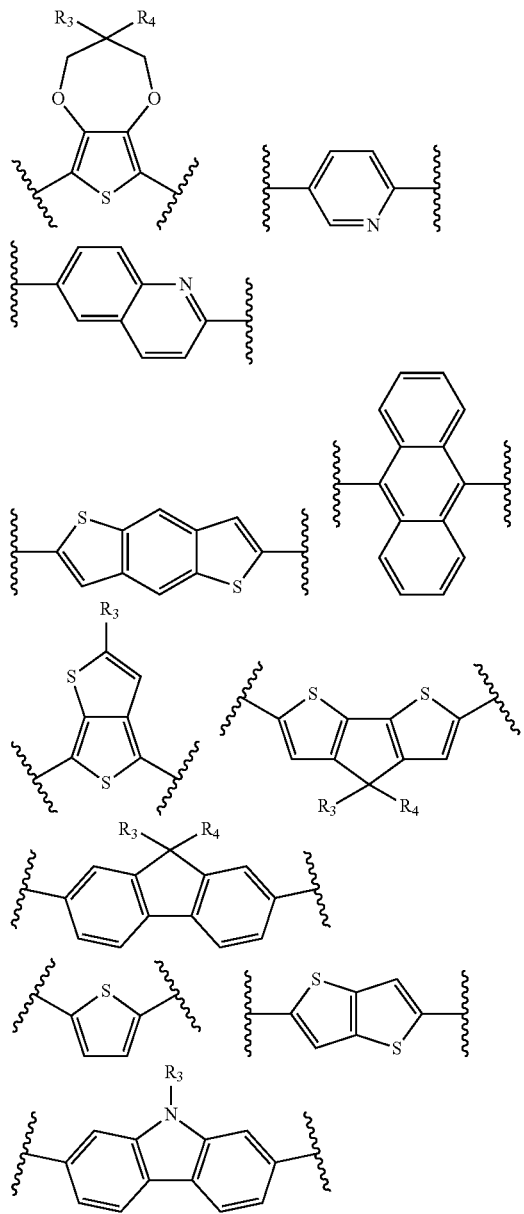
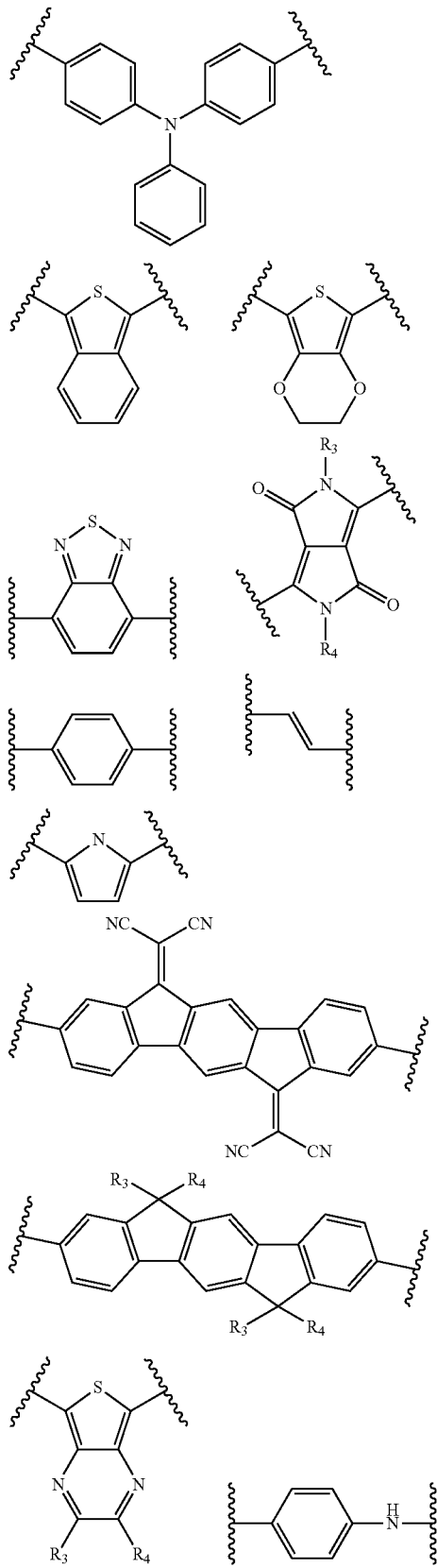

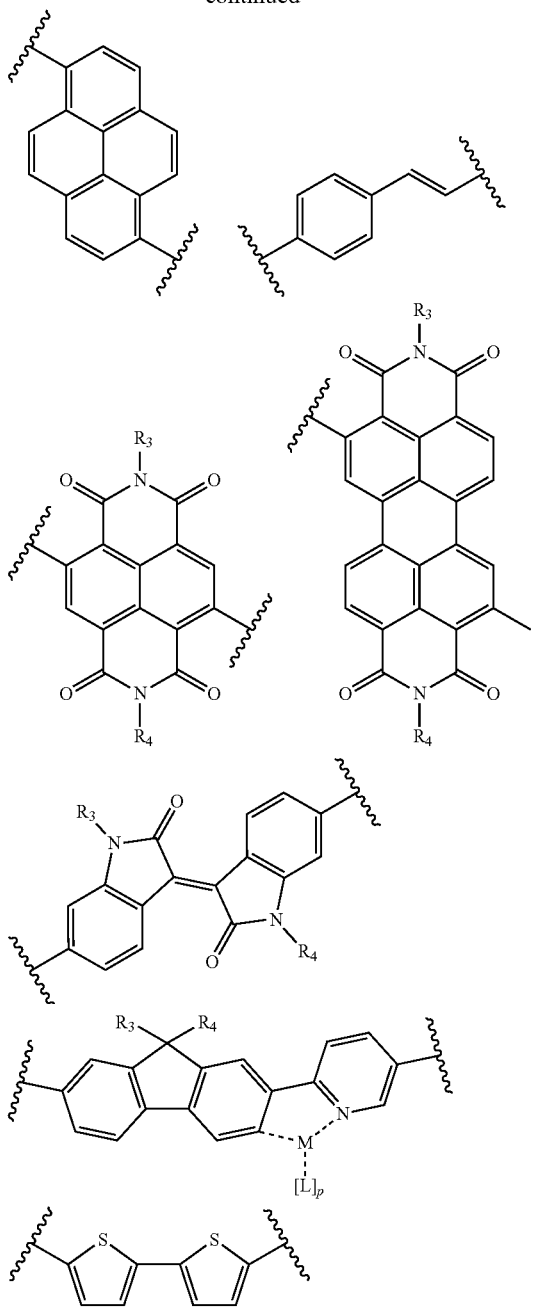

wherein M, L R₃ and R₄ are as defined above.

In an embodiment, the π-conjugated monomers each independently comprise a moiety having the formula IV shown below:
wherein

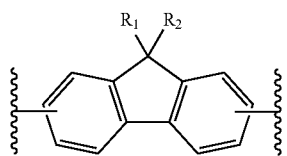

$R_1$ and $R_2$ are each independently hydrogen or a group:
—X-Q wherein
X is absent selected from the group consisting of (1-30C)alkylene, —O-(1-30C)alkylene, —S-(1-30C)alkylene, —NH-(1-30C)alkylene, (2-30C)alkenylene, (2-30C)alkynylene, —[(CH$_2$)$_2$—O]$_n$—, —[O—(CH$_2$)$_2$]$_n$—, —[O—CH$_2$MeCH$_2$]$_n$—, —[CH$_2$MeCH$_2$—O]$_n$— and —[O—Si(R$_z$)$_2$], (wherein R$_z$ is (1-4C)alkyl and n is 1 to 30), —[(CH$_2$)$_n$'—(CF$_2$)$_m$']— (wherein n' is 0-20 and m' is 1 to 30) and Q is a terminal group selected from hydrogen, halogen, methyl, hydroxyl, carboxy, (1-4C)alkoxycarbonyl, amino, —C═CH$_2$, —C≡CH, —SH, -biotin, -streptavidin, -antibody, —CF$_3$, OSO$_3$H, —SO$_3$H, —OPO$_2$OH and zwitterions (e.g. betaine) and a polymerisable group selected from silane, siloxane, acrylate, epoxy, styrene, or a salt thereof, or $R_1$ and $R_2$ are aryl or heteroaryl groups optionally substituted with a substituent group (e.g. one or more groups of formula —X-Q above);

or $R_1$ and $R_2$ are linked so that, together with the carbon atom to which they are attached, they form ring system (e.g. a phenyl or fluorene ring) optionally substituted with a substituent group (e.g. a group —X-Q defined above);

and with the proviso that, in at least one monomer of formula IV, Q is or comprises a group selected from amino, carboxy, hydroxyl, halogen, vinyl, alkenyl, alkynyl, carbonyl, thiol, -biotin, -streptavidin or an antibody.

In another embodiment, the π-conjugated monomers each independently have a structure defined by formula V shown below:
wherein

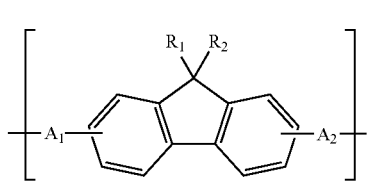

$R_1$ and $R_2$ are as defined hereinbefore;
$A_1$ and $A_2$ are absent or independently absent or selected from any one of the following moieties:

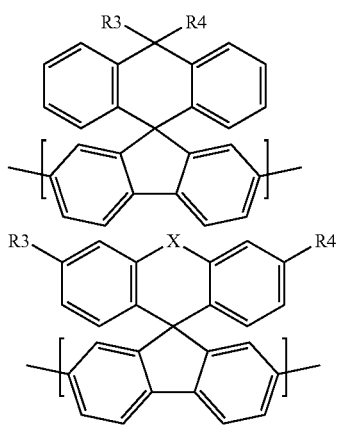

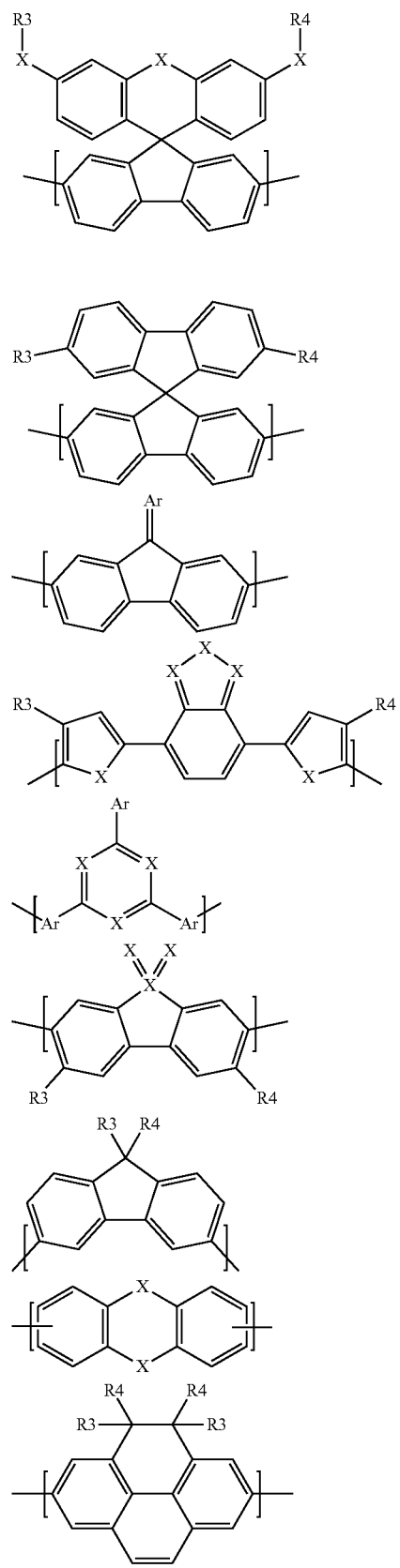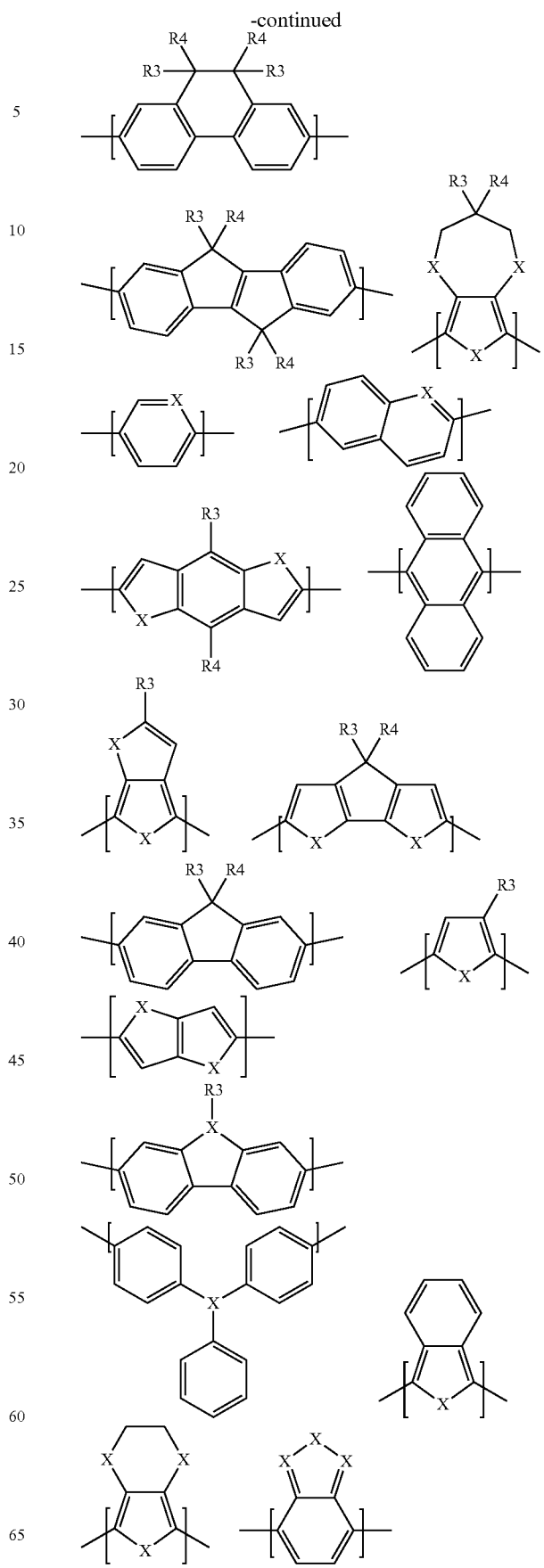

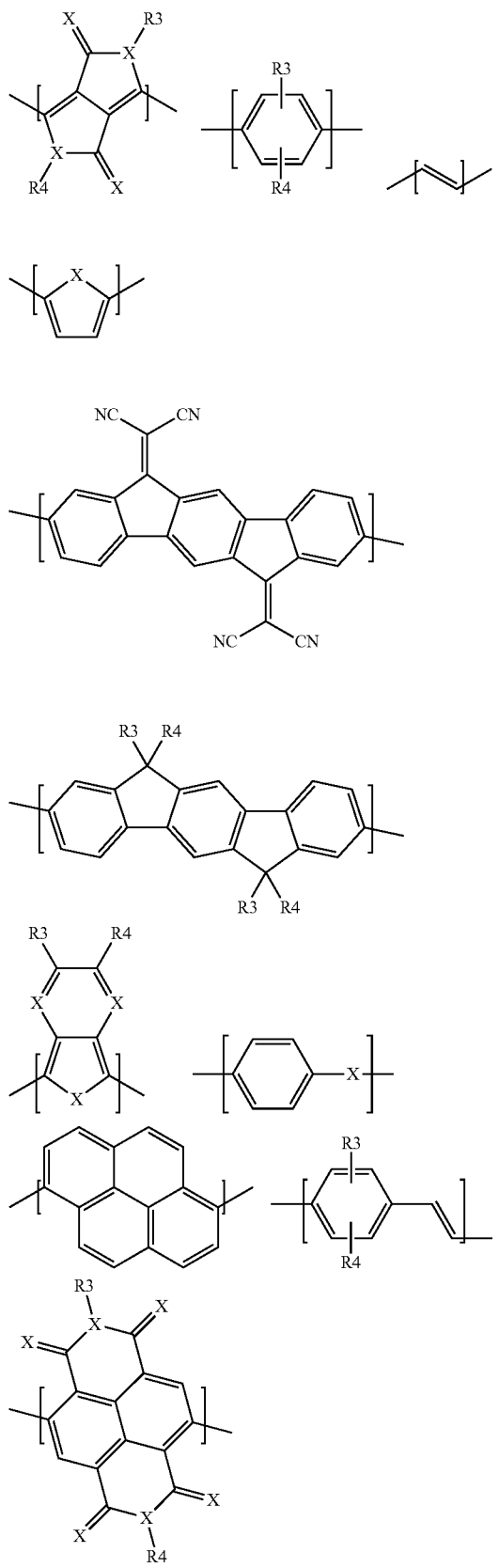
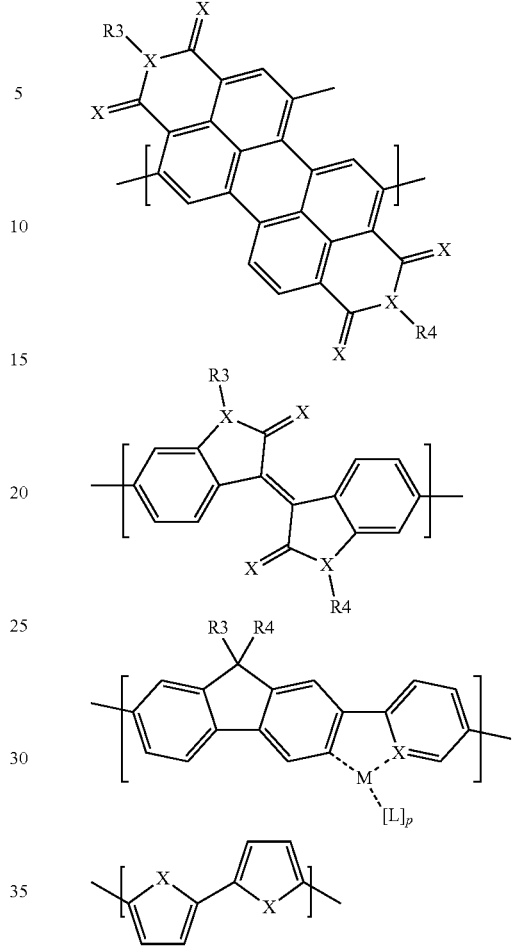

and wherein $R_3$ and $R_4$ are each as defined hereinbefore, or are groups $R_1$ and $R_2$ as defined above, or are each independently hydrogen or a group:

—$X^1$-$Q^1$ wherein
$X^1$ is selected from the group consisting of (1-30C) alkylene, (2-30C)alkenylene, (2-30C)alkynylene, —[(CH$_2$)$_2$—O]$_n$—, —[O—(CH$_2$)$_2$]$_n$—, —[O—CH$_2$MeCH$_2$]$_n$—, —[CH$_2$MeCH$_2$—O]$_n$— and —[O—Si(R$_z$)$_2$]$_n$— (wherein R$_z$ is (1-4C)alkyl and n is 1 to 30), —[(CH$_2$)$_{n'}$—(CF$_2$)$_{m'}$]— (wherein n' is 0-20 and m' is 1 to 30)

$Q^1$ is a terminal group selected from hydrogen, halogen, methyl, hydroxyl, carboxy, (1-4C)alkoxycarbonyl, amino, —C=CH$_2$, —C≡CH, —SH, -biotin, -streptavidin, —CF$_3$, OSO$_3$H, —SO$_3$H, —OPO$_2$OH and zwitterions (e.g. betaine) and a polymerisable group selected from silane, siloxane, acrylate, epoxy, styrene, or a salt thereof;

M is a metal selected from Ir, Pt, Rh, Re, Ru, Os, Cr, Cu, Pd and Au;

L is a ligand independently selected from the group consisting of halo, (1-30C)hydrocarbyl optionally comprising one or more heteroatoms selected from N, O, S, Si, Ge, As or P, or an aryl or heteroaryl group optionally substituted with one or more substituents selected from (1-4C)alkyl, halo, aryl or heteroaryl;

X is a heteroatom selected from N, O, P, S, Si, Ge, As or Se (especially N, O or S)

is a cyclic or polycyclic group which is optionally a π-conjugated (e.g. fluorene);

p is 1 to 4 and with the proviso that, in at least one monomer of formula V, $Q^1$ is or comprises a group selected from amino, carboxy, hydroxyl, halogen, vinyl, alkenyl, alkynyl, carbonyl, thiol, -biotin or -streptavidin.

In another embedment, $A_1$ and $A_2$ are absent or independently selected from any one of the following:

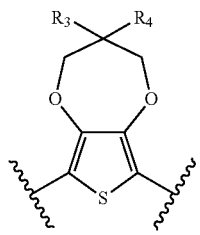
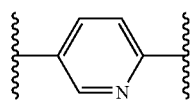
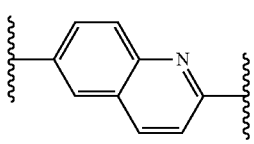
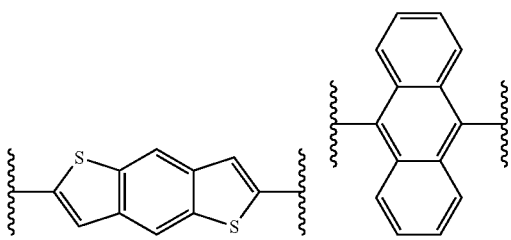
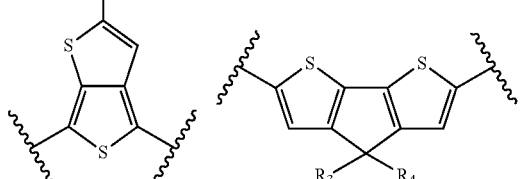
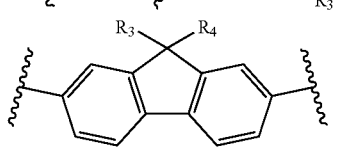
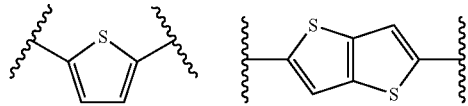
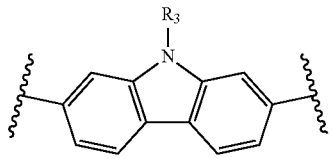

-continued

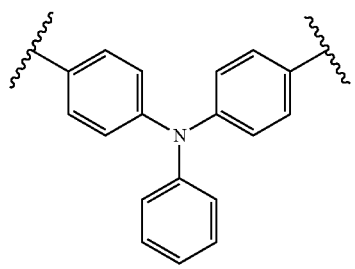
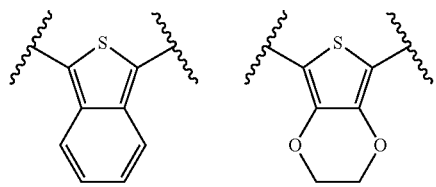
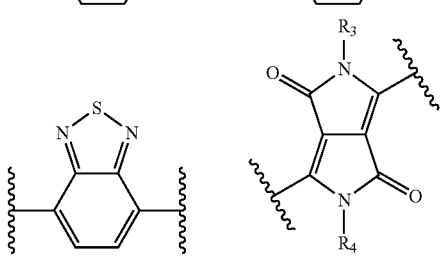
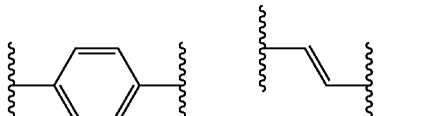
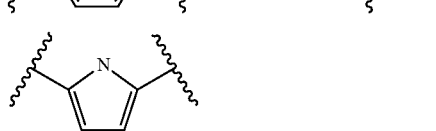
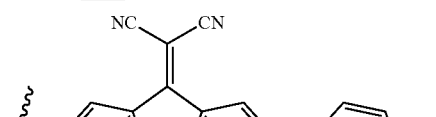
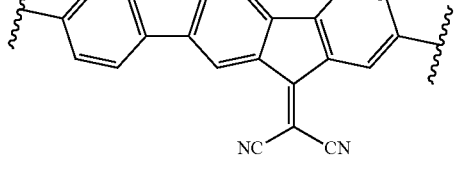
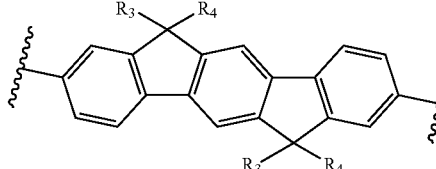
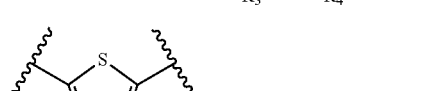
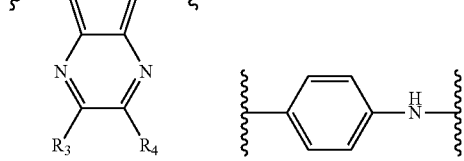

-continued

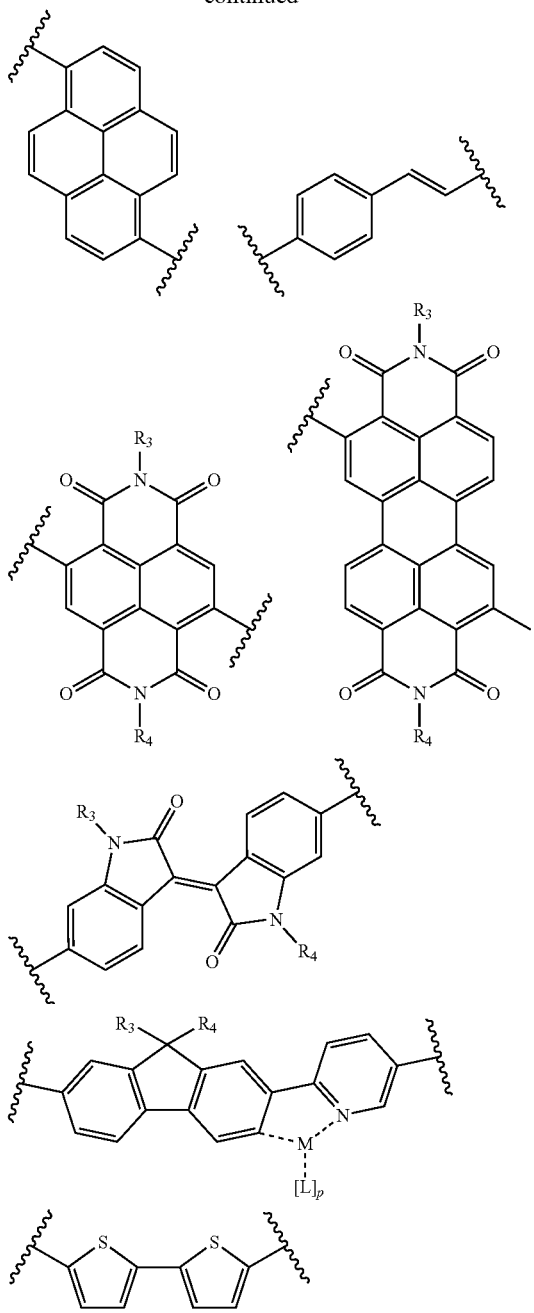

wherein M, L, p, R₃ and R₄ are each as defined hereinbefore.

In another embodiment, the π-conjugated monomers each independently have a structure defined by formula VI below:

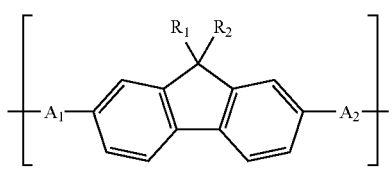

(VI)

$R_1$, $R_2$, $A_1$ and $A_2$ are as defined hereinbefore.

In another embodiment, $A_1$ and $A_2$ are independently absent or selected from any one of the following moieties:

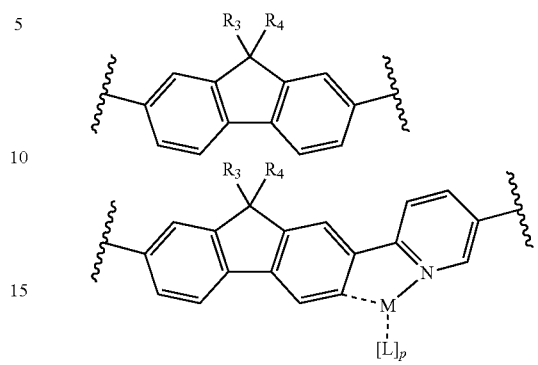

wherein $R_3$, $R_4$, M, L and p are as defined hereinbefore.

In another embodiment both $A_1$ and $A_2$ are absent.

In another embodiment, when present:

X and $X^1$ are independently selected from the group consisting of (1-30C)alkylene, (2-30C)alkenylene, (2-30C)alkynylene, —[(CH₂)₂—O]ₙ—, —[O—(CH₂)₂]ₙ—, —[O—CH₂MeCH₂]ₙ—, —[CH₂MeCH₂—O]ₙ— and —[O—Si(R_z)₂]ₙ— (wherein R_z is methyl and n is 1 to 30);

Q and $Q^1$ are independently a terminal group selected from hydrogen, halogen, methyl, hydroxyl, carboxy, (1-4C)alkoxycarbonyl, amino, —C═CH₂, —C≡CH, —SH, -biotin, -streptavidin, CF₃, OSO₃H, —SO₃H, —OPO₂OH and zwitterions (e.g. betaine) and a polymerisable group selected from silane, siloxane, acrylate, epoxy, styrene, or a salt thereof;

M is a metal selected from Ir, Pt, Rh, Re, Ru, Os, Cr, Cu, Pd and Au;

L is a ligand independently selected from the group consisting of halo, (1-30C)hydrocarbyl optionally comprising one or more heteroatoms selected from N, O, S, Si or P, or an aryl or heteroaryl group optionally substituted with one or more substituents selected from (1-4C)alkyl, halo, aryl or heteroaryl; and p is 1 to 4;

and with the proviso that at least one group Q and/or $Q^1$ is or comprises a group selected from amino, carboxy, hydroxyl, halogen, vinyl, alkenyl, alkynyl, carbonyl, thiol, -biotin or -streptavidin.

In another embodiment, when present:

X and $X^1$ are independently selected from the group consisting of (1-20C)alkylene, (2-20C)alkenylene, (2-20C)alkynylene, —[(CH₂)₂—O]ₙ— —[O—CH₂MeCH₂]ₙ—, —[CH₂MeCH₂—O]ₙ— and —[O—(CH₂)₂]ₙ— (wherein n is 1 to 20);

Q and $Q^1$ are independently a terminal group selected from hydrogen, halogen, —SH, —C═CH₂, —C≡CH, methyl, hydroxyl, carboxy, (1-4C)alkoxycarbonyl, amino, -biotin or -streptavidin, or a salt thereof;

M is a metal selected from Ir, Pt, Cr, Cu, Pd and Au;

L is a ligand independently selected from the group consisting of halo, (1-20C)hydrocarbyl optionally comprising one or more heteroatoms selected from N, O, or S, or an aryl or heteroaryl group optionally substituted with one or more substituents selected from (1-4C)alkyl, halo, aryl or heteroaryl; and p is 1 to 4;

and with the proviso that at least one group Q and/or $Q^1$ is or comprises a group selected from amino, carboxy, hydroxyl, halogen, vinyl, alkenyl, alkynyl, carbonyl, thiol, -biotin or -streptavidin.

In another embodiment, when present:
X and $X^1$ are independently selected from the group consisting of (1-20C)alkylene, —[(CH$_2$)$_2$—O]$_n$— and —[O—(CH$_2$)$_2$]$_n$—, —[O—CH$_2$MeCH$_2$]$_n$—, —[CH$_2$MeCH$_2$—O]$_n$— (wherein n is 1 to 20);
Q and $Q^1$ are independently a terminal group selected from hydrogen, halogen, —SH, —C=CH$_2$, —C≡CH, methyl, hydroxyl, carboxy, (1-4C)alkoxycarbonyl, amino, -biotin or -streptavidin, or a salt thereof;
M is a metal selected from Ir, Pt, Cr, Cu, Pd and Au;
L is a ligand independently selected from the group consisting of aryl or heteroaryl, optionally substituted with one or more substituents selected from (1-4C)alkyl, halo, aryl or heteroaryl; and
p is 1 to 4;
and with the proviso that at least one group Q and/or $Q^1$ is or comprises a group selected from amino, carboxy, hydroxyl, halogen, vinyl, alkenyl, alkynyl, carbonyl, thiol, -biotin or -streptavidin.

In another embodiment, when present:
X and $X^1$ are independently selected from the group consisting of (1-20C)alkylene, —[(CH$_2$)$_2$—O]$_n$— and —[O—(CH$_2$)$_2$]$_n$— (wherein n is 1 to 20);
Q and $Q^1$ are independently a terminal group selected from hydrogen, halogen, —SH, —C=CH$_2$, —C≡CH, (1-4C)alkoxycarbonyl, methyl, hydroxyl, carboxy, amino, -biotin or -streptavidin, or a salt thereof;
M is Ir;
L is a ligand independently selected from the group consisting of aryl or heteroaryl, optionally substituted with one or more substituents selected from aryl or heteroaryl; and
p is 1 to 2;
and with the proviso that at least one group Q and/or $Q^1$ is or comprises a group selected from amino, carboxy, hydroxyl, halogen, vinyl, alkenyl, alkynyl, carbonyl, thiol, -biotin or -streptavidin.

In another embodiment, when present:
X and $X^1$ are independently selected from the group consisting of (4-12C)alkylene, —[(CH$_2$)$_2$—O]$_n$— and —[O—(CH$_2$)$_2$]$_n$— (wherein n is 1 to 15);
Q and $Q^1$ are independently a terminal group selected from hydrogen, halogen, —SH, —C=CH$_2$, —C≡CH, (1-4C)alkoxycarbonyl, methyl, hydroxyl, carboxy, amino, -biotin or -streptavidin, or a salt thereof;
M is Ir;
L is a ligand independently selected from the group consisting of phenyl or 6-membered heteroaryl, optionally substituted with one or more substituents selected from phenyl or 6-membered heteroaryl; and
p is 1 to 2;
and with the proviso that at least one group Q and/or $Q^1$ is or comprises a group selected from amino, carboxy, hydroxyl, halogen, vinyl, alkenyl, alkynyl, carbonyl, thiol, -biotin or -streptavidin.

In another embodiment, when present:
X and $X^1$ are independently selected from the group consisting of (4-12C)alkylene and —[(CH$_2$)$_2$—O]$_n$— (wherein n is 1 to 15);
Q and $Q^1$ are independently a terminal group selected from hydrogen, halogen, —SH, —C=CH$_2$, —C≡CH, (1-4C)alkoxycarbonyl, methyl, hydroxyl, carboxy, amino, -biotin or -streptavidin, or a salt thereof;
M is Ir;
L is a ligand independently selected from the group consisting of phenyl or 6-membered heteroaryl, optionally substituted with one or more substituents selected from phenyl or 6-membered heteroaryl; and
p is 1 to 2;
and with the proviso that at least one group Q and/or $Q^1$ is or comprises a group selected from amino, carboxy, hydroxyl, halogen, vinyl, alkenyl, alkynyl, carbonyl, -biotin or -streptavidin.

In any of the embodiments mentioned hereinbefore, X and/or $X^1$ may also be —(CH$_2$)$_m$(CF$_2$)$_n$— (wherein m is 0 to 30 and n is 1 to 30) and Q and/or $Q^1$ may also be —CF$_3$.

In another embodiment, the π-conjugated monomers are each independently selected from any of the following structures:

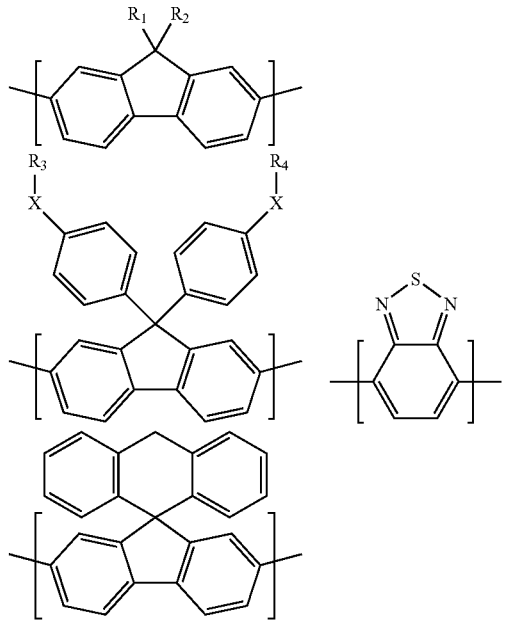

wherein R$_1$, R$_2$, R$_3$ and R$_4$ are each independently selected from: —(CH$_2$)$_n$R$_{50}$ and —(CH$_2$CH$_2$O)$_n$R$_{50}$;
wherein n is 1 to 15 and R$_{50}$ is selected from H, (1-15C)alkyl, —CO$_2$H, —CO$_2$(1-6C)alkyl, —CO$_2$Na, —CH=CH$_2$, —OC(O)-biotin and —OSO$_3$Na;
and X is O.

In another embodiment, R$_1$ and R$_2$ are both selected from —(CH$_2$)$_7$CH$_3$, —(CH$_2$)$_5$CO$_2$Et, —(CH$_2$)$_{10}$CO$_2$H, —(CH$_2$)$_4$CH=CH$_2$, —(CH$_2$)$_{11}$OSO$_3$Na, —(CH$_2$)$_5$CO$_2$Et, —(CH$_2$)$_{10}$CO$_2$Na, —(CH$_2$CH$_2$O)$_3$CH$_3$, —(CH$_2$)$_{11}$OC(O)-biotin and —(CH$_2$CH$_2$O)$_{12}$CH$_3$; R$_3$ and R$_4$ are selected from 2-ethylhexyl, —(CH$_2$)$_{11}$OSO$_3$Na, —(CH$_2$CH$_2$O)$_n$CH$_3$ and —(CH$_2$)$_{10}$CO$_2$Na.

In an embodiment, the π-conjugated monomers are each independently selected from any of the following structures:

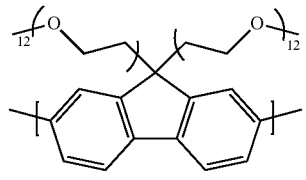

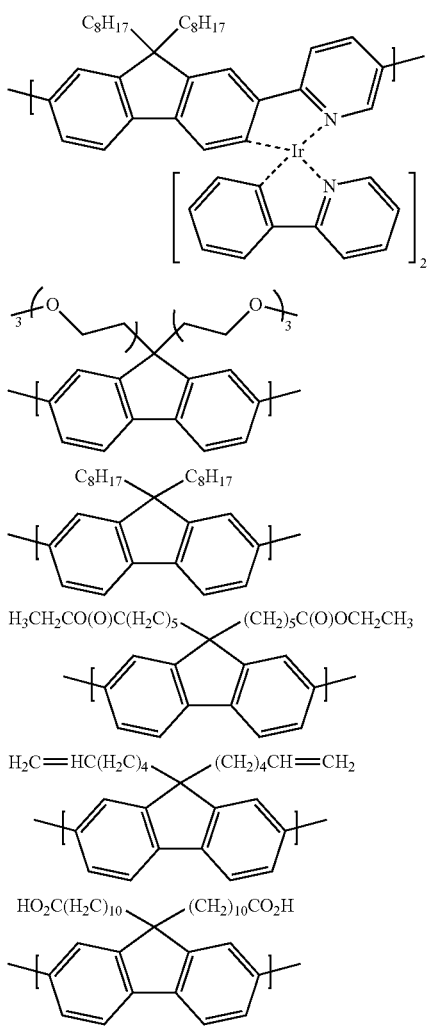

In another embodiment, the π-conjugated monomers are each independently selected from any of the following structures:

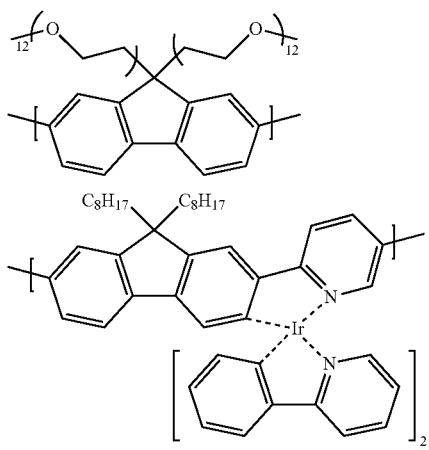

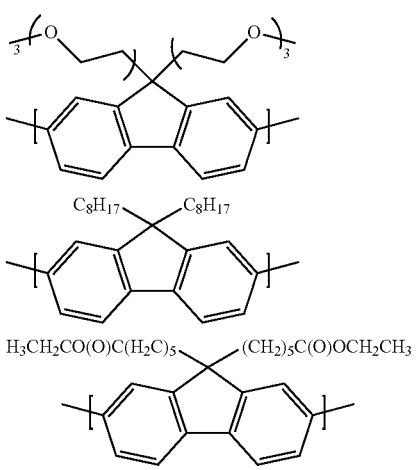

with the proviso that at least one monomer component comprises a amino, carboxy, hydroxyl, halogen, vinyl, alkenyl, alkynyl, carbonyl, thiol, streptavidin and/or biotin group, or a functional group capable of binding a streptavidin or biotin group in a subsequent reaction, or a salt thereof.

In another embodiment, the π-conjugated monomers are each independently selected from any of the following structures:

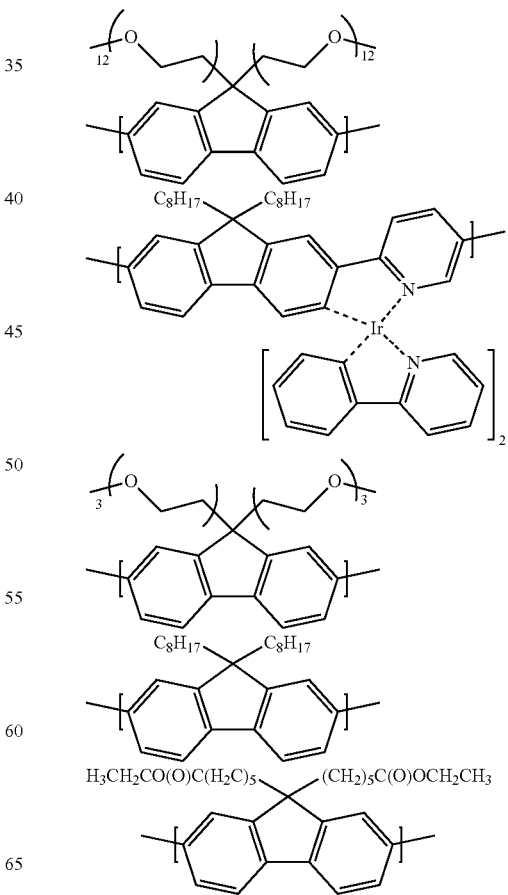

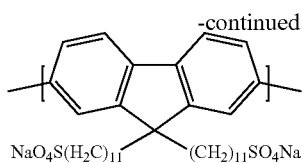

with the proviso that at least one monomer component comprises a amino, carboxy, hydroxyl, halogen, vinyl, alkenyl, alkynyl, carbonyl, thiol, streptavidin and/or biotin group, or a functional group capable of binding a streptavidin or biotin group in a subsequent reaction, or a salt thereof.

In another embodiment, the nanoparticle has a particle size (Z-average, measured by DLS) of 20-400 nm. Suitably, the nanoparticle has a particle size of 30-400 nm. More suitably, the nanoparticle has a particle size of less than 30-300 nm. Even more suitably, the nanoparticle has a particle size of less than 30-250 nm. Even more suitably, the nanoparticle has a particle size of less than 30-200 nm. Most suitably, the nanoparticle has a particle size of less than 30-100 nm.

In another embodiment, the nanoparticle has a particle size of 20-400 nm. More suitably, the nanoparticle has a particle size of less than 20-300 nm. Even more suitably, the nanoparticle has a particle size of less than 20-250 nm. Even more suitably, the nanoparticle has a particle size of less than 20-200 nm. Most suitably, the nanoparticle has a particle size of less than 20-100 nm.

In another embodiment, the nanoparticle has a particle size of 10-400 nm. More suitably, the nanoparticle has a particle size of less than 10-300 nm. Even more suitably, the nanoparticle has a particle size of less than 10-250 nm. Even more suitably, the nanoparticle has a particle size of less than 10-200 nm. Most suitably, the nanoparticle has a particle size of less than 10-100 nm.

In another embodiment, the polymers forming the nanoparticles of the present invention have a degree of polymerisation of 10 to 800, more suitably 20 to 600.

In another embodiment, the nanoparticle comprises 1-10 mol % of the cross linker. Suitably, the nanoparticle comprises 2-8 mol % of the cross linker. More suitably, the nanoparticle comprises 3-7 mol % of the cross linker. Most suitably, the nanoparticle comprises 4.5-5.5 mol % of the cross linker.

The Drug or Biological Molecule

In an embodiment, the conjugate comprises a drug molecule. Any suitable drug molecule may be used. In order to be coupled to the nanoparticle, the drug molecule must comprise a functional group capable of reacting with a functional group present on the nanoparticle (e.g. to form an ester, amide, disulphide bond) or a second moiety (e.g. streptavidin or biotin) capable affinity pairing to a first moiety (e.g. biotin or streptavidin) present on the nanoparticle.

Suitably, the conjugate comprises a biological molecule. Examples of suitable biological molecules include, but are not limited to, cells, proteins (e.g. antibodies, enzymes etc.), peptides, amino acids, oligonucleotides (DNA or RNA) or peptide nucleic acids.

In an embodiment, the biological molecule is a protein (e.g. antibody, enzyme etc.), peptide, amino acid, oligonucleotide (DNA or RNA) or a peptide nucleic acid.

In a further embodiment, the biological molecule is a protein (e.g. antibody, enzyme etc.), an oligonucleotide (e.g. DNA or RNA) or a peptide nucleic acid.

In a further embodiment, the biological molecule is an antibody, an enzyme, an oligonucleotide (e.g. DNA or RNA) or a peptide nucleic acid.

In a further embodiment, the biological molecule is an antibody.

Aqueous Compositions

In a further aspect, the present invention provides an aqueous composition comprising a plurality of conjugates as defined herein dispersed within an aqueous medium.

The aqueous medium provides a water-based vehicle in which the nanoparticles are dispersed. The medium may comprise additional components, such as dissolved materials (salts, buffers etc.). Suitably, the aqueous medium is water. More suitably, the aqueous medium is purified water.

In another embodiment, the aqueous composition of the invention may further comprise a stabiliser to maintain the conjugates in suspension. Any suitable stabiliser may be used such as, for example, non-ionic, cationic or anionic stabilisers known in the art. Particular examples of suitable stabilisers include non-ionic stabilisers, for example: Triton X series octylphenol ethoxylates, Tergitol series nonylphenol ethoxylates (Dow Chemical Company); Brij series poly (oxyethylene) glycol alkyl ethers, Superonic series, Tween series polysorbate surfactants (Croda); Pluronic series of block copolymers based on ethylene oxide and propylene oxide (BASF); Tetronic series tetra functional block copolymers based on ethylene oxide and propylene oxide, Lutensol series (BASF); Igepal series Rhodasurf series, Antarox series (Rhodia); and Merpol series (Stepan Co.) and high molecular weight PEG In another embodiment, the aqueous composition further comprises an anionic stabiliser, for example sodium dodecylsulphate (SDS), and/or a cationic stabiliser, for example cetyl trimethylammonium bromide (CTAB).

The loading of the conjugate in the aqueous composition may be high. For example, the concentration of the conjugate in the aqueous medium may be greater than or equal to 15 mM. In an embodiment, the concentration of the conjugate in the aqueous medium is greater than or equal to 20 mM. In an alternative embodiment, the concentration of the conjugate in the aqueous medium is greater than or equal to 25 mM.

Alternatively, depending on the application of interest, the aqueous composition may be more dilute. In an embodiment, the concentration of the conjugate in the aqueous medium (e.g. water) is less than or equal to 15 mg/ml.

In an alternative embodiment, the concentration of the conjugate in the aqueous medium is less than or equal to 5 wt %. Suitably, the concentration of the conjugate in the aqueous medium is less than or equal to 3 wt %. More suitably, the concentration of the conjugate in the aqueous medium is less than or equal to 1 wt %.

Methods of the Invention

According to a third aspect of the present invention, there is provided a method of forming a conjugate as defined herein, the method comprising the steps of:
 (i) forming the nanoparticles by emulsion polymerisation, mini-emulsion polymerisation or dispersion polymerisation techniques to provide an aqueous suspension of nanoparticles;
 (ii) reacting the nanoparticles with the drug or biological molecule so as to form an aqueous suspension of the conjugate.

In step (i), the nanoparticles are formed by emulsion polymerisation, mini-emulsion polymerisation or dispersion polymerisation techniques to provide a suspension of nanoparticles. Suitably, the polymerisation reaction is carried out in an aqueous medium to yield a suspension of nanoparticles in an aqueous medium.

Emulsion polymerisation, miniemulsion polymerisation and dispersion polymerisation techniques will be known to one of skill in the art.

In the case of mini emulsion polymerisation, the monomeric components are dissolved in a suitable organic solvent (e.g. chlorobenzene, toluene or xylenes) along with the catalyst (e.g. $Pd(PPh_3)_4$, $IPr*PdTEACl_2$ or $Pd_2(dba)_3/P(o\text{-}tol)_3$). This solution is then added to an aqueous medium of water, a suitable base (e.g. tetraethylammonium hydroxide solution (40% in water), NaOH) and optionally with a suitable emulsifier. Any suitable emulsifier may be used, such as, for example, SDS, Triton X102/X405/X705, Brij L23, and/or Tween 20. The resultant emulsion may be stirred and/or ultrasonicated to form an emulsion, suitably a miniemulsion. The emulsion mixture may then be gently heated to a temperature of between 30 and 100° C. (for $Pd(PPh_3)_4$, $Pd_2(dba)_3/P(o\text{-}tol)_3$ suitably between 50 and 95° C., and more suitably between 50 and 80° C.; and for $IPr*PdTEACl_2$ ideally 30° C.) for period of time (e.g. from 1 hour to 2 days) to form the polymeric nanoparticles. A person skilled in the art will appreciate that the temperature of heating depends on catalyst system employed.

In an embodiment, the nanoparticles are formed by Suzuki coupling or Stille coupling reactions. Such coupling reactions are known in the art.

In another embodiment, the nanoparticles are formed by reacting π-monomeric moieties as defined herein with a pre-made cross-linking moiety as defined herein.

In another embodiment, the method further comprises the step of purifying the aqueous suspension of nanoparticles. Suitably, the aqueous suspension of nanoparticles is purified by contacting the aqueous suspension of nanoparticles with at least one organic solvent or solvent (usually buffer or water) exchange using tangential flow filtration In another embodiment, contacting the aqueous suspension of nanoparticles with at least one suitable organic solvent causes precipitation of the nanoparticles. The precipitated nanoparticles may then be centrifuged, with the supernatant then decanted to leave the purified nanoparticles. Optionally, the purified nanoparticle may be re-suspended in water, and the purification process then repeated.

In another embodiment, when the nanoparticles are lipophilic, the at least one organic solvent is a polar solvent that is miscible with water (e.g. methanol, propanol, acetone).

In another embodiment, when the nanoparticles are hydrophilic, the at least one organic solvent is a non-polar solvent.

To form the conjugate of the invention, in step (ii), the nanoparticles are reacted with the drug or biological molecule. In this context, the term "react" encompasses mixing the nanoparticles with the drug or biological molecule and facilitating the binding of the nanoparticle to the drug or biological molecule. In embodiments where one of the drug/biological molecule or the nanoparticle bears a biotin moiety and the other bears a streptavidin moiety, the binding is facilitated by simply mixing the drug/biological molecule with the nanoparticle in a suitable medium, e.g. an aqueous medium. In embodiments, where the amide, ester or disulphide bond formation is required in order to bind the drug/biological molecule to the nanoparticle, then suitable solvents/buffer and reaction conditions to facilitate such bond formation are employed. A person skilled in the art will appreciate how to form such bonds by the selection of appropriate reaction conditions, solvents etc.

Suitably, the reaction in step (ii) is carried out in an aqueous medium.

According to a further aspect of the present invention, there is provided a conjugate or an aqueous composition obtainable, obtained, or directly obtained, by a method defined herein.

Uses of the Nanoparticle Compositions

The conjugates of the present invention are particularly suited to biological applications. They can be conveniently prepared in aqueous media and administered as aqueous compositions. Furthermore, the nanoparticles of the present invention are highly photoluminescent enabling small quantities of the conjugate to be used for biological imaging.

Thus, in a further aspect, the invention provides the use of a conjugate as defined herein for biological imaging or sensing.

In an embodiment, the nanoparticle composition is used in in vivo or in vitro imaging or sensing applications.

EXAMPLES

Examples of the invention will now be described, for the purpose of reference and illustration only, with reference to the accompanying figures, in which.

EXAMPLE 1—PREPARATION OF CROSS-LINKED PFO NANOPARTICLES

1.1—Cross-Linked PFO Nanoparticles

Synthesis

Referring to Scheme 1 and Table 1 shown below, sodium dodecyl sulphate (SDS) (50.0 mg) and deionised water (10 mL) were transferred to a Schlenk tube and the resultant solution was degassed by bubbling with argon for 20 minutes. Monomer A (see Table 1), crosslinker B (see Table 1) and monomer C (58.6 mg, 9.12×10$^{-2}$ mmol) were dissolved in toluene (1 mL), to which hexadecane (78 µL) was also added, and this solution was degassed for 5 minutes in the same manner. Tetrakis(triphenylphosphine)palladium(0) (2.2 mg, 9.13×10$^{-3}$ mmol) was added to the monomer solution, which was then transferred to the reaction vessel. The reaction mixture was emulsified by ultrasonication (Cole Parmer 750W ultasonicator, fitted with microtip, on 22% power) for 2 minutes while cooling with an ice bath. The Schlenk tube was resealed and the miniemulsion was heated to 72° C., followed by addition of 1M aqueous sodium hydroxide solution (365 µL), and the reaction mixture was stirred for 16 hours. After cooling to room temperature, the cap of the reaction vessel was removed and the emulsion was stirred for 5 hours to remove the residual toluene.

TABLE 1

| Reaction variables for synthesis of cross-linked PFO nanoparticles | | |
|---|---|---|
| Sample Name | Monomer A (mass, moles) | Crosslinker B (mass, moles) |
| NP-X2.5 | 45.0 mg<br>8.21 × 10$^{-2}$ mmol | 2.9 mg<br>4.6 × 10$^{-3}$ mmol |
| NP-X5 | 40.0 mg<br>7.29 × 10$^{-2}$ mmol | 5.8 mg<br>9.1 × 10$^{-3}$ mmol |
| NP-X10 | 30.0 mg<br>5.47 × 10$^{-2}$ mmol | 11.6 mg<br>1.82 × 10$^{-2}$ mmol |

Surfactant Removal and DLS Analysis (Nanoparticles in Water)

Figure 1:
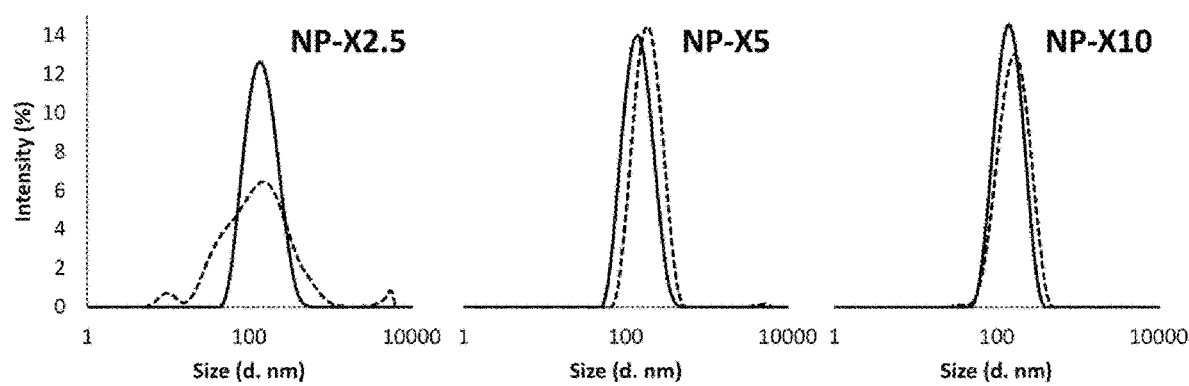
FIG. 1 shows DLS particle size histograms of the cross-linked nanoparticles of Example 1.1 in water (solid line) or THF (broken line).

A 400 µL aliquot of the crude nanoparticle suspension was diluted with 1.6 mL of deionised water, to which Amberlite XAD-2 resin (20 mg, pre-washed with 2×2 mL of water) was added. The suspension was shaken at room temperature for 15 minutes before decanting off the nanoparticle suspension. This Amberlite XAD-2 purification step was repeated, after which time the suspension no longer foamed upon shaking and was filtered through glass wool prior to dynamic light scattering (DLS) analysis of particle size using a Malvern Zetasizer Nano ZS. Results are shown in Table 2 and FIG. 1.

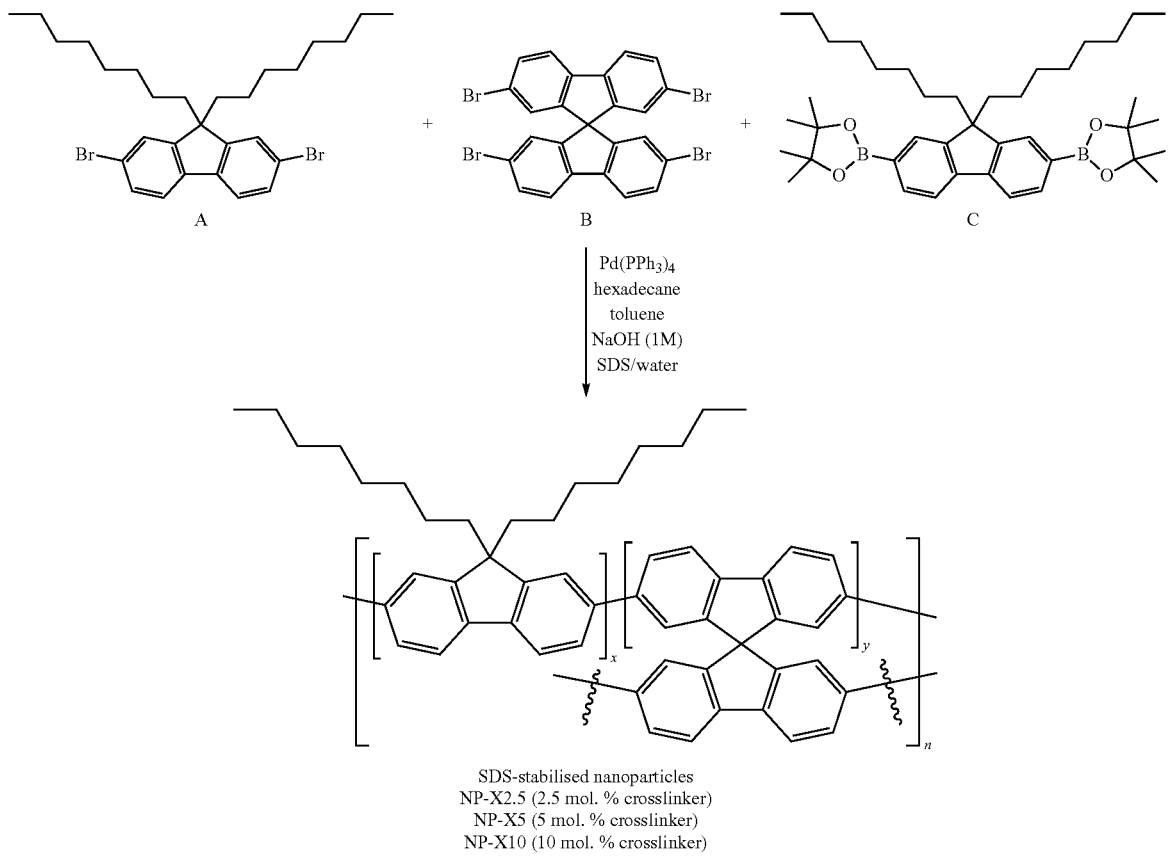

Scheme 1

SDS-stabilised nanoparticles
NP-X2.5 (2.5 mol. % crosslinker)
NP-X5 (5 mol. % crosslinker)
NP-X10 (10 mol. % crosslinker)

TABLE 2

DLS analysis of cross-linked PFO nanoparticles in water

| Sample Name | Z-Average (d · nm) | Size by Intensity (d · nm) | St. Dev. (nm) | Pdl |
|---|---|---|---|---|
| NP-X2.5 | 128 | 154 | 69 | 0.16 |
| NP-X5 | 130 | 151 | 60 | 0.14 |
| NP-X10 | 129 | 150 | 56 | 0.13 |

DLS Analysis (Nanoparticles in THF)

A 200 μL aliquot of the crude nanoparticle suspension was flocculated through addition of 1.3 mL toluene and the polymer was isolated by centrifugation (14,000 rpm, 1 minute) and decantation of the supernatant. The polymer was dried in air to remove residual methanol before dispersing in tetrahydrofuran (THF, 1 mL). The resultant suspension was measured directly using a Malvern Zetasizer Nano ZS. Results are shown in Table 3 and FIG. 1.

TABLE 3

DLS analysis of cross-linked PFO nanoparticles in THF

| Sample name | Z-Average (d. nm) | Size by Intensity (d. nm) | St. Dev. (nm) | Pdl |
|---|---|---|---|---|
| NP-X2.5 | — | — | — | n/a[a] |
| NP-X5 | 174 | 198 (99.6%) 4827 (0.4%)[b] | 74 (99.6%) 711 (0.4%)[a] | 0.13 |
| NP-X10 | 147 | 175 | 73 | 0.15 |

[a]secondary peak likely to result from a small proportion of aggregated nanoparticles UV/Vis Analysis (Nanoparticles in Water or THF)

Figure 2:
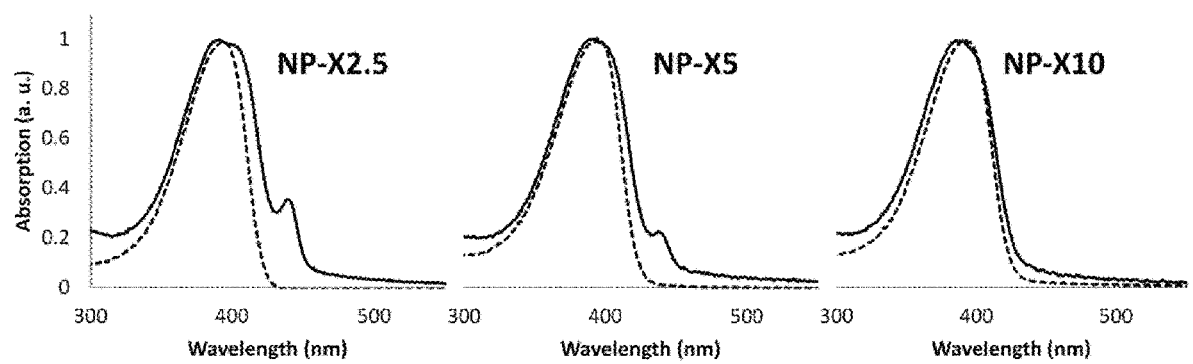
FIG. 2 shows UV/Vis spectra of the cross-linked nanoparticles of Example 1.1 in water (solid line) or THF (broken line).
Figure 3:
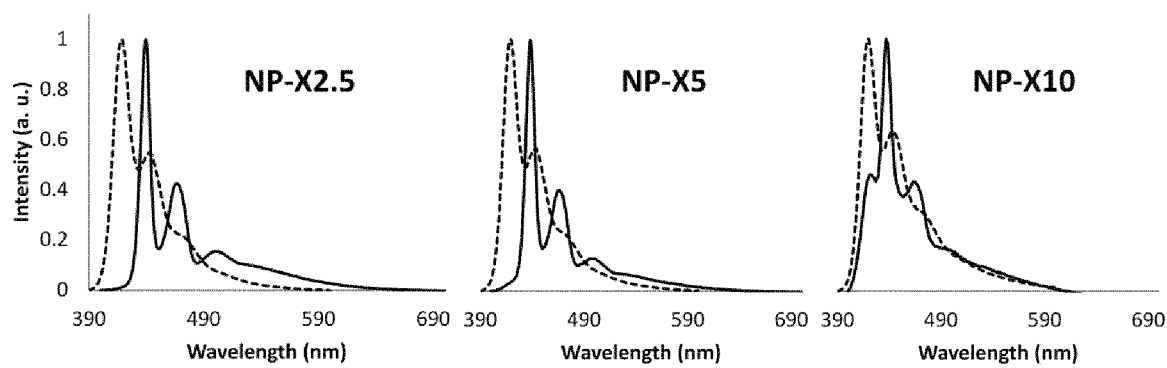
FIG. 3 shows PL spectra of the cross-linked nanoparticles of Example 1.1 in water (solid line) or THF (broken line).

Following surfactant removal via treatment with Amberlite XAD-2, 40 μL of the nanoparticle suspension was diluted with 3 mL of water. UV-Vis absorption spectra of the nanoparticles at this concentration were recorded on a Varian Cary 55 5000UV-Vis-NIR spectrophotometer at room temperature. FIG. 2 shows UV/Vis spectra of the cross-linked PFO nanoparticles.

Photoluminescence (PL) Analysis (Nanoparticles in Water or THF)

Following surfactant removal via treatment with amberlite XAD-2, 40 μL of the nanoparticle suspension was diluted with 3 mL of water. PL spectra were recorded on a Varian Cary Eclipse fluorimeter. FIG. 2 shows PL spectra of the cross-linked PFO nanoparticles Photoluminescence (PL) Analysis (Nanoparticles in Water)

Photoluminescence measurements were obtained using a Fluoromax-4 spectrofluorometer. Measurements were carried out on dilute dispersions of the nanoparticles in water (800 μL, abs>1), using the same volume of water for background measurements. The results are provided in Table 4.

TABLE 4

Optical properties of PFO nanoparticles in water

| Sample Name | $\lambda_{max}$ | $\lambda_{em}$[a] |
|---|---|---|
| NP-X2.5 | 390 | 440 |
| NP-X5 | 390 | 438 |
| NP-X10 | 390 | 437 |

[a]$\lambda_{ex}$ = 380 nm

1.2—Ethyl Ester-Functionalised Cross-Linked PFO Nanoparticles

Synthesis

Referring to Scheme 2 shown below, sodium dodecyl sulfate (50.0 mg) and deionised water (10 mL) were transferred to a Schlenk tube and the resultant solution was degassed by bubbling with argon for 20 minutes. Crosslinker A (5.8 mg, 9.12×10$^{-3}$ mmol), monomer B (44.4 mg, 7.30× 10$^{-2}$ mmol) and monomer C (58.6 mg, 9.12×10$^{-2}$ mmol) were dissolved in toluene (1 mL), to which hexadecane (78 μL) was also added, and this solution was degassed for 5 minutes in the same manner. Tetrakis(triphenylphosphine)palladium(0) (2.2 mg, 9.13×10$^{-3}$ mmol) was added to the monomer solution, which was then transferred to the reaction vessel. The reaction mixture was emulsified by ultrasonication (Cole Parmer 750W ultasonicator, fitted with microtip, on 22% power) for 2 minutes while cooling with an ice bath. The Schlenk tube was resealed and the miniemulsion was heated to 72° C., followed by addition of 1M aqueous sodium hydroxide solution (365 μL), and the reaction mixture was stirred for 16 hours. After cooling to room temperature, the cap of the reaction vessel was removed and the emulsion was stirred for 5 hours to remove the residual toluene.

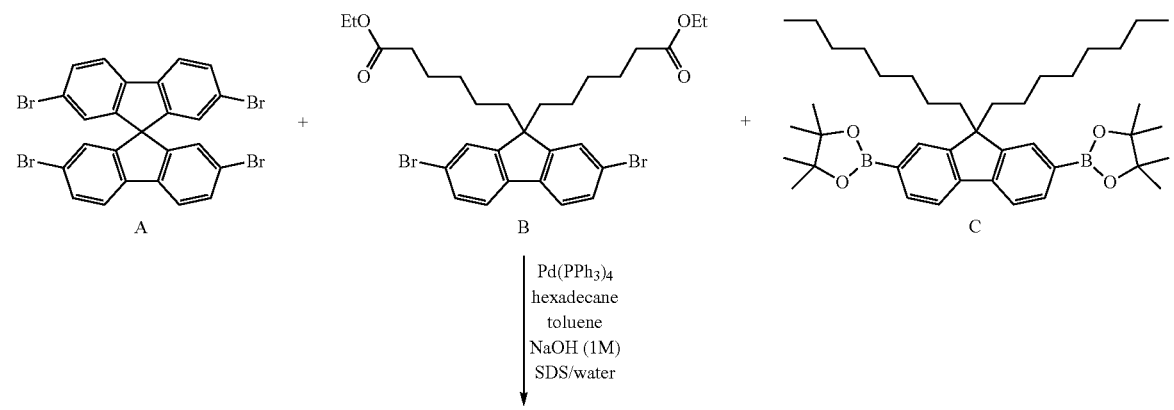

Scheme 2

-continued

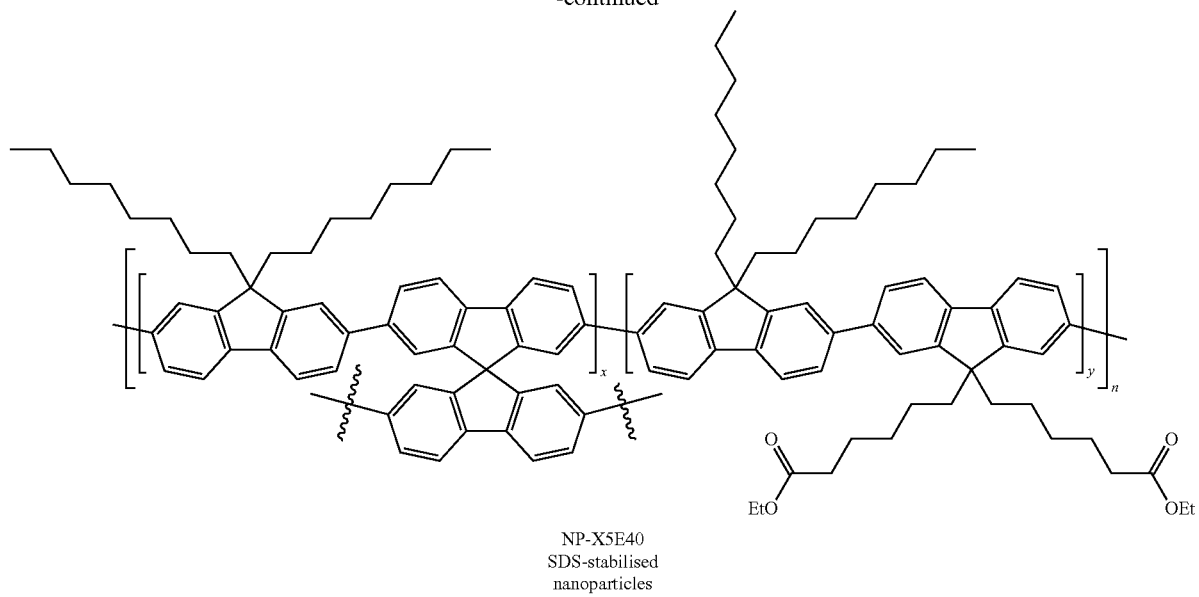

NP-X5E40
SDS-stabilised
nanoparticles

DLS Analysis (Nanoparticles in Water or THF)

Figure 4:
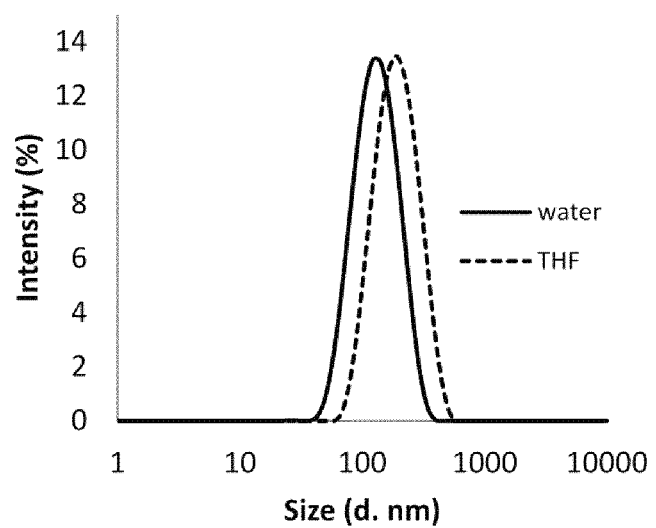
FIG. 4 shows DLS particle size histograms of the cross-linked nanoparticles of Example 1.2 in water (solid line) and THF (broken line) dispersants.

Surfactant removal was carried out using the general procedure described in Example 1. Flocculation and resuspension in THF were carried out using the general procedure described in Example 1. DLS analysis was carried out as in Example 1, using either water or THF as the dispersant. The results are provided in Table 5 and FIG. 4.

TABLE 5

DLS analysis of ethyl ester-functionalised nanoparticles in water or THF

| Sample Name | Dispersant | Z-Average (d. nm) | Size by Intensity (d. nm) | St. Dev (nm) | Pdl |
|---|---|---|---|---|---|
| NP-X5E40 | Water | 118 | 139 | 56 | 0.14 |
| NP-X5E40 | THF | 170 | 204 | 82 | 0.16 |

UV/Vis and PL Analysis (Nanoparticles in Water)

Figure 5:
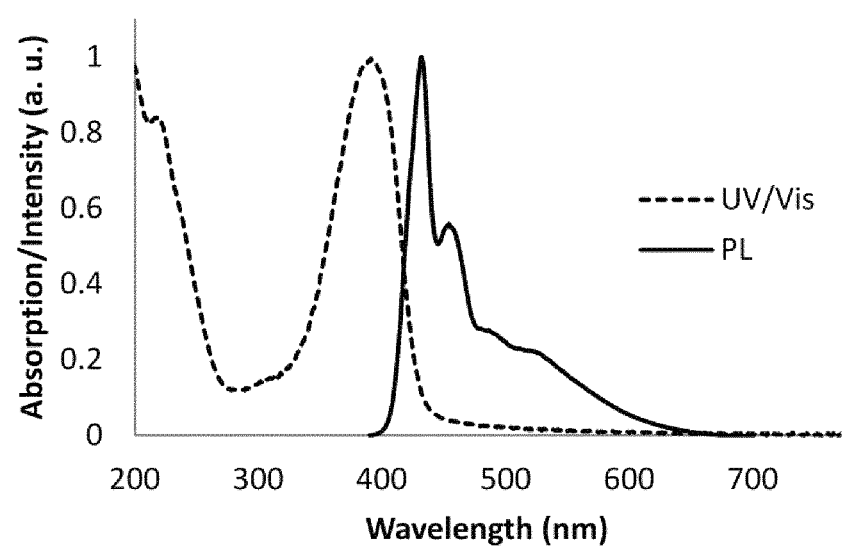
FIG. 5 shows UV/Vis (broken line) and PL (solid line) spectra of the cross-linked nanoparticles of Example 1.2.

The general UV/Vis and PL analytical procedures described in Example 1 were used to record the UV/Vis and PL spectra of the nanoparticles in dilute aqueous dispersion. The results are provided in FIG. 5.

PL Analysis (Nanoparticles in Water)

PL measurements were obtained using the general method described in Example 1. The results are provided in Table 6.

TABLE 6

Optical properties of ethyl ester-functionalised nanoparticles in water

| Sample Name | $\lambda_{max}$ | $\lambda_{em}$[a] |
|---|---|---|
| NP-X5E40 | 391 | 432 |

[a]$\lambda_{ex}$ = 380 nm 1.3—Cross-Linked Phosphorescent Nanoparticles

Method

Referring to Scheme 3 and Table 7 shown below, sodium dodecyl sulfate (50.0 mg) and deionised water (10 mL) were transferred to a Schlenk tube and the resultant solution was degassed by bubbling with argon for 20 minutes. Monomers A (see Table 7), C (20.5 mg, 1.82×10$^{-2}$ mmol) and D (58.6 mg, 9.12×10$^{-2}$ mmol) and crosslinker B (5.8 mg, 9.12×10$^{-3}$ mmol) were dissolved in toluene (1 mL), to which hexadecane (78 µL) was also added, and this solution was degassed for 5 minutes in the same manner. Tetrakis(triphenylphosphine)palladium(0) (2.2 mg, 9.13×10$^{-3}$ mmol) was added to the monomer solution, which was then transferred to the reaction vessel. The reaction mixture was emulsified by ultrasonication (Cole Parmer 750W ultasonicator, fitted with microtip, on 22% power) for 2 minutes while cooling with an ice bath. The Schlenk tube was resealed and the miniemulsion was heated to 72° C., followed by addition of 1M aqueous sodium hydroxide solution (365 µL), and the reaction mixture was stirred for 16 hours. After cooling to room temperature, the cap of the reaction vessel was removed and the emulsion was stirred for 5 hours to remove the residual toluene.

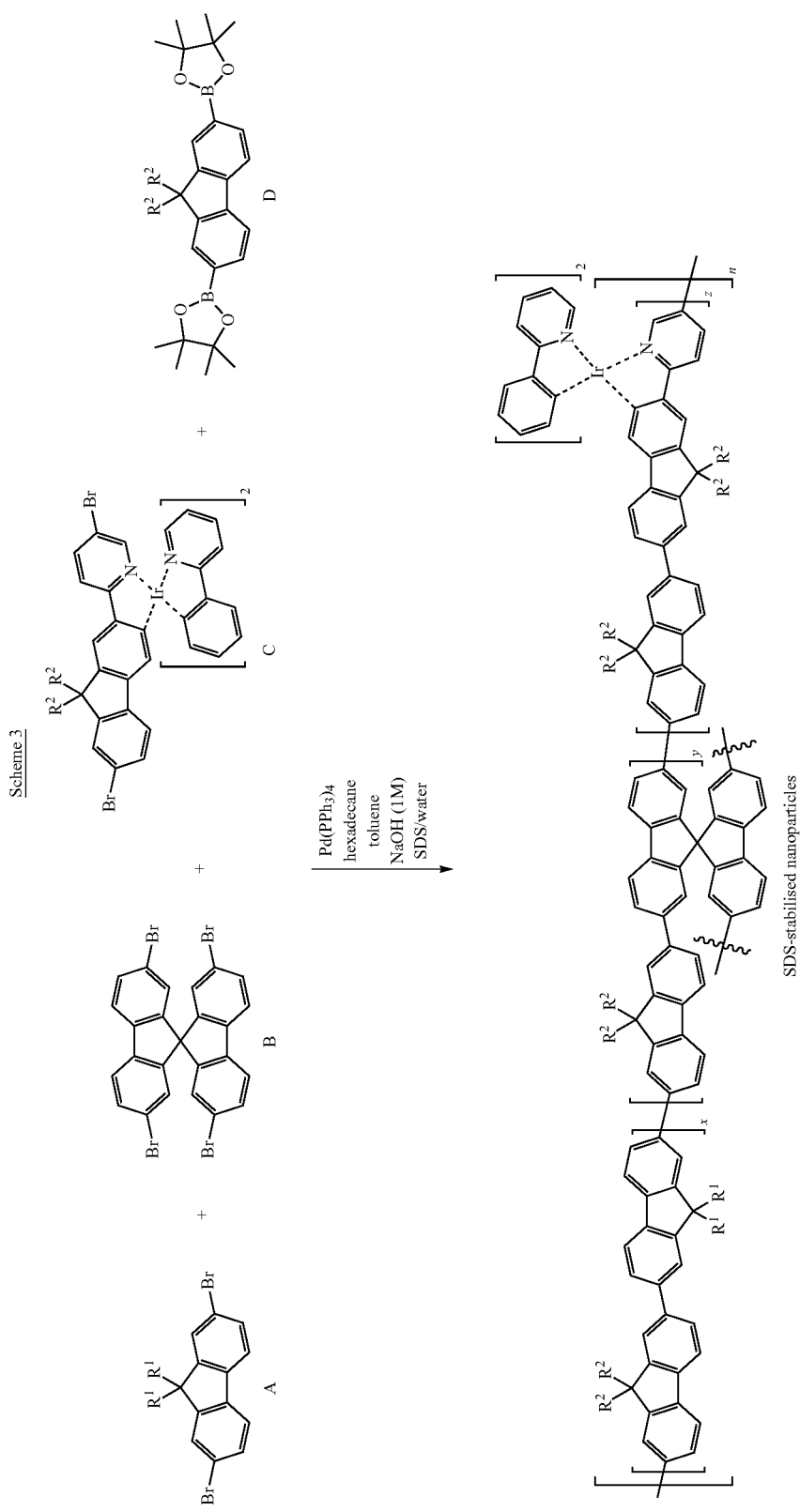

TABLE 7

Reaction variables for synthesis of cross-linked phosphorescent nanoparticles

| Sample Name | Monomer A Side Chain ($R^1$) | Monomer A (mass, moles) |
|---|---|---|
| NP-XIr1 | Octyl | 30.0 mg<br>5.47 × $10^{-2}$ mmol |
| NP-XIr2 | MeO-PEG3 | 33.7 mg<br>5.57 × $10^{-2}$ mmol |

DLS Analysis (Nanoparticles in Water or THF)

Figure 6:
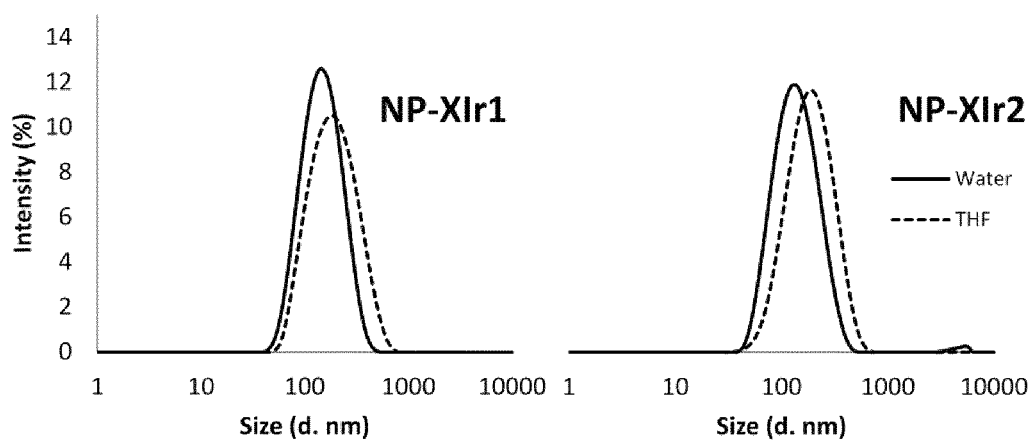
FIG. 6 shows DLS sizing histograms of cross-linked phosphorescent nanoparticles in water (solid line) or THF (broken line) of the cross-linked nanoparticles of Example 1.3.

Surfactant removal was carried out using the general procedure described in Example 1. Flocculation and resuspension in THF were carried out using the general procedure described in Example 1. DLS analysis was carried out as in Example 1, using either water or THF as the dispersant. The results are provided in Table 8 and FIG. 6.

TABLE 8

DLS analysis of cross-linked phosphorescent nanoparticles in water or THF

| Sample Name | Dispersant | Z-Average (d. nm) | Size by Intensity (d. nm) | St. Dev (nm) | PdI |
|---|---|---|---|---|---|
| NP-XIr1 | Water | 131 | 158 | 69 | 0.15 |
| NP-XIr1 | THF | 167 | 210 | 109 | 0.18 |
| NP-XIr2 | Water | 126 | 150 (99.3%)<br>4709 (0.7%)[a] | 70 (99.3%)<br>774 (0.7%)[a] | 0.19 |
| NP-XIr2 | THF | 165 | 205 | 98 | 0.18 |

[a]Secondary peak likely to result from a small proportion of aggregated nanoparticles UV/Vis and PL Analysis (Nanoparticles in Water or THF)

Figure 7:
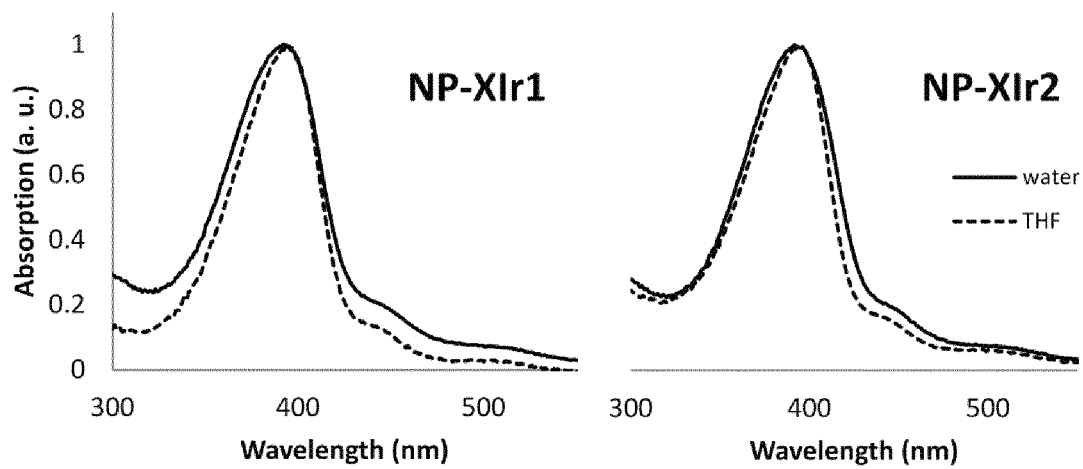
FIG. 7 shows UV/Vis spectra of the cross-linked nanoparticles of Example 1.3 in water (solid line) or THF (broken line).
Figure 8:
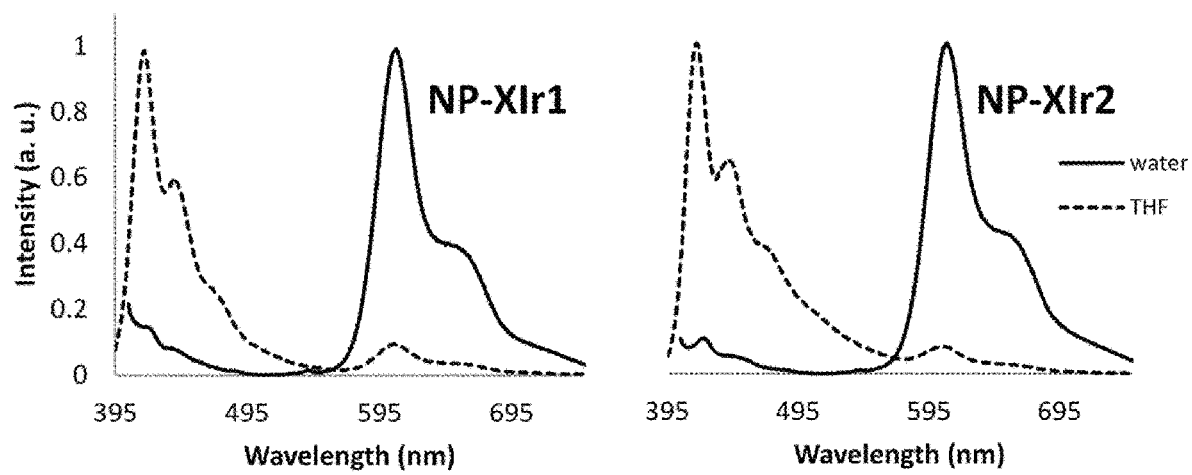
FIG. 8 shows PL spectra of the cross-linked nanoparticles of Example 1.3 in water (solid line) or THF (broken line).

The general UV/Vis and PL analytical_procedures described in Example 1 were used to record the UV/Vis (FIG. 7) and PL (FIG. 8) spectra of the nanoparticles in dilute aqueous dispersion or THF.

PL Analysis (Nanoparticles in Water)

PL measurements were obtained using the general method described in Example 1. The results are provided in Table 9.

TABLE 9

Optical properties of cross-linked phosphorescent nanoparticles in water

| Sample Name | $\lambda_{max}$ | $\lambda_{em}$[a] |
|---|---|---|
| NP-Ir1 | 392 | 609 |
| NP-Ir2 | 392 | 609 |

[a]$\lambda_{ex}$ = 390 nm

1.4—PEG3 Functionalised 10% Cross-Linked PFO Nanoparticles

Synthesis

Referring to Scheme 4 shown below, tetraethylammonium hydroxide solution (40% in water) (0.1567 g, 0.4 mmol), was added to an aqueous solution (50 ml) of non-ionic surfactant, Triton x-102 (2.5 g, 5 wt % in de-ionised water) in a 100 ml three necked round bottom flask. Then contents were then degassed for 30 mins by bubbling nitrogen gas through the stirred solution. Then a separate 10 ml two necked round bottom flask was used to mix together the monomers in the organic solvent prior to addition to the reaction flask. 9,9-dioctylfluorene-2,7-di-boronic acid-bis(1,3-propanediol)ester (0.1151 g, 0.2 mmol), 2,7-dibromo-9,9-bis(2-(2-(2-methoxyethoxy)ethoxy)ethyl)fluorene (0.0967 g, 0.16 mmol) and 2,2',7,7'-tetrabromo-9,9'-spirobifluorene (0.0126 g, 0.02 mmol) were dissolved in xylene (2 ml). The monomer solution was degassed and then the catalyst IPr*PdTEACl$_2$ (0.0095 g, 0.008 mmol) was added, followed by further degassing of the resultant solution. A syringe was used to transfer the monomer/catalyst into the stirred surfactant/base solution in the main reaction flask now maintained at 30° C. with stirring and maintaining under nitrogen gas for 24 h.

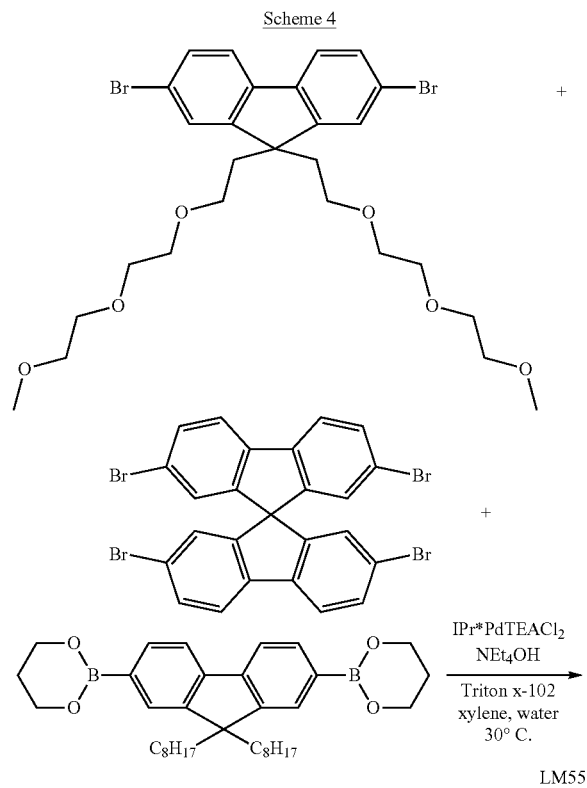

Scheme 4

DLS Analysis (Nanoparticles in Water or THF)

Figure 9:
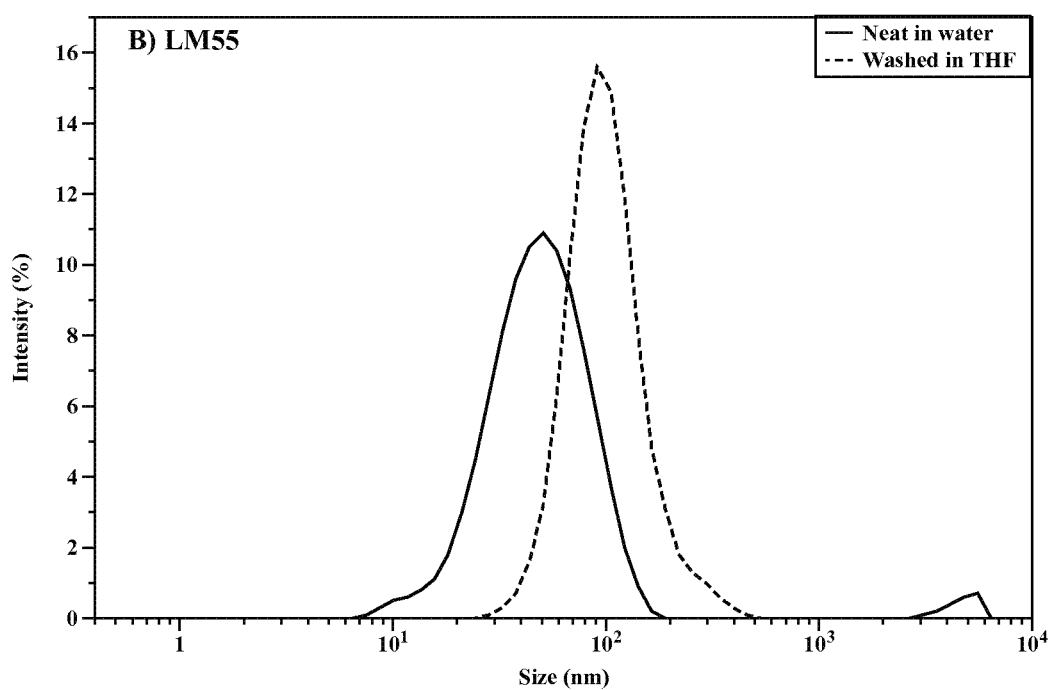
FIG. 9 shows DLS sizing histograms of the cross-linked nanoparticles of Example 1.4 in water (solid line) and THF (broken line).

500 μl of sample was transferred to centrifuge vial the 1.5 ml of methanol was added. The sample vial was centrifuged at 14,000 rpm for 5 min then the liquid was decanted. Crude sample was washed with methanol 3 times and re-dispersed in THF in order to measure the size of particles. Neat products without further purification were also investigated. The results are shown in FIG. 9 and Table 10. Concentrations of polymer in water was 23 μg/ml.

TABLE 10

Particle sizes of CPNs in water and THF at 25° C.

| Sample | Size (nm) | Dz (nm) | STD (nm) | PdI |
|---|---|---|---|---|
| LM55 Neat | 50 | 44 | 26.81 | 0.244 |
| LM55 in THF | 108 | 218 | 51.80 | 0.217 |

Optical Properties

Figure 12:
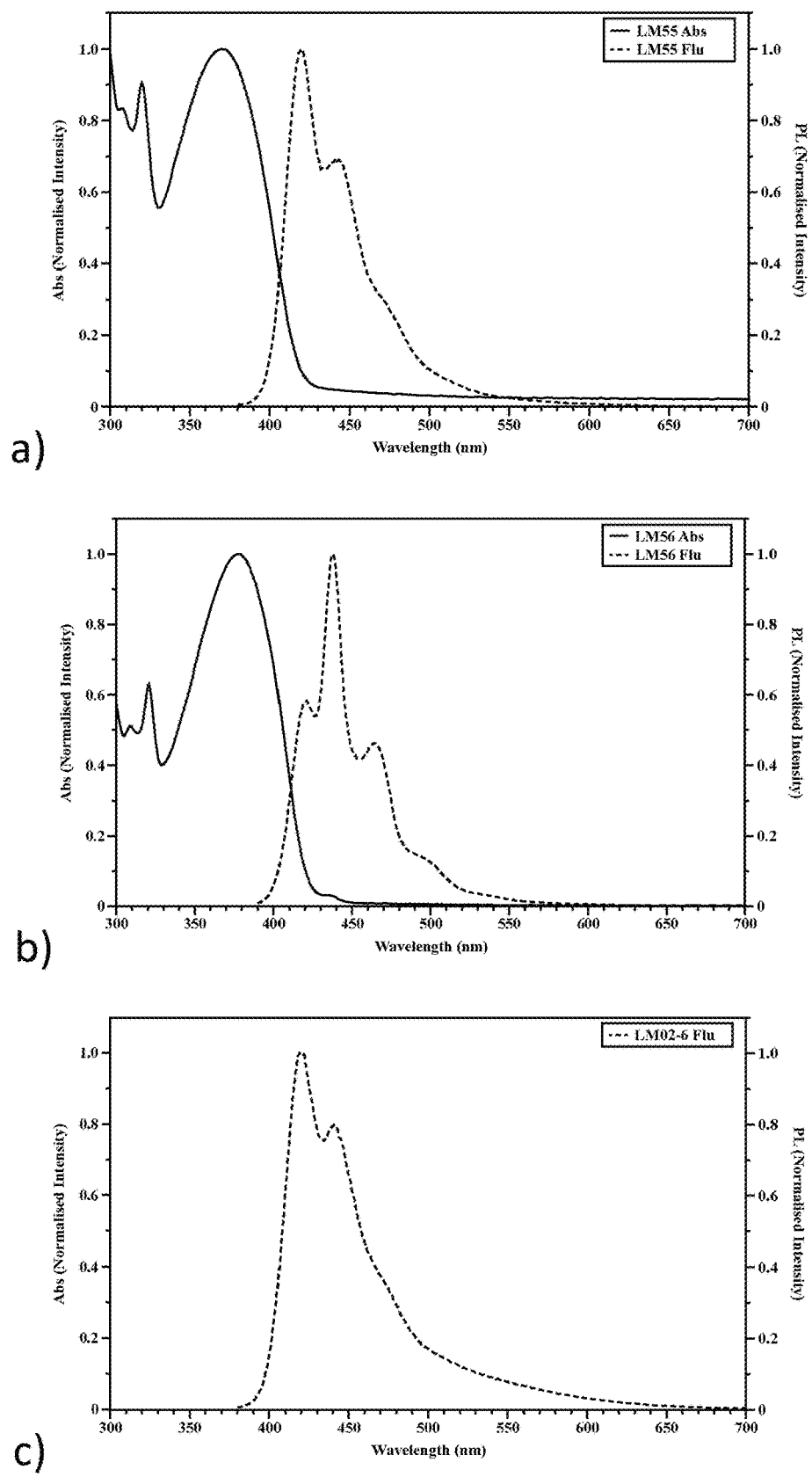
FIG. 12 shows absorption and emission spectra of the cross-linked nanoparticles of Examples 1.4 (FIG. 12a), 1.5 (FIG. 12b) and 1.6 (FIG. 12c).

Referring to Table 11 and FIG. 12, LM55 exhibited maxima band at 370 nm but no β-phase was observed.

TABLE 11

Summarized optical properties of cross-linked polymer in water

| Sample | Final polymer conc. (mg/ml) | Size (nm) | $\lambda_{abs}$ (nm) | $\lambda_{em}$ (nm) | $E_g^*$ |
|---|---|---|---|---|---|
| LM55 | 2.5 | 50 | 370 | 420, 441 | 2.91 |

1.5—PEG3 Functionalised 5% Cross-Linked PFO Nanoparticles

Synthesis

Referring to Scheme 5 shown below, tetraethylammonium hydroxide solution (40% in water) (0.1567 g, 0.4 mmol), was added to an aqueous solution (50 ml) of non-ionic surfactant, Triton x-102 (2.5 g, 5 wt % in de-ionised water) in a 100 ml three necked round bottom flask. Then contents were then through degassed for 30 mins by bubbling nitrogen gas through the stirred solution. Then a separate 10 ml two necked round bottom flask was used to mix together the monomers in the organic solvent prior to addition to the reaction flask. 9,9-dioctylfluorene-2,7-di-boronic acid-bis(1,3-propanediol)ester (0.1151 g, 0.2 mmol), 2,7-dibromo-9,9-dioctylfluorene (0.0768 g, 0.14 mmol), 2,7-dibromo-9,9-bis(2-(2-(2-methoxyethoxy)ethoxy)ethyl)fluorene (0.0242 g, 0.04 mmol) and 2,2',7,7'-tetrabromo-9,9'-spirobifluorene (0.0063 g, 0.01 mmol) were dissolved in xylene (2 ml). The monomer solution was degassed and then the catalyst IPr*PdTEACl$_2$ (0.0095 g, 0.008 mmol) was added, followed by further degassing of the resultant solution. A syringe was used to transfer the monomer/catalyst into the stirred surfactant/base solution in the main reaction flask now maintained at 30° C. with stirring and maintaining under nitrogen gas for 24 h.

Scheme 5

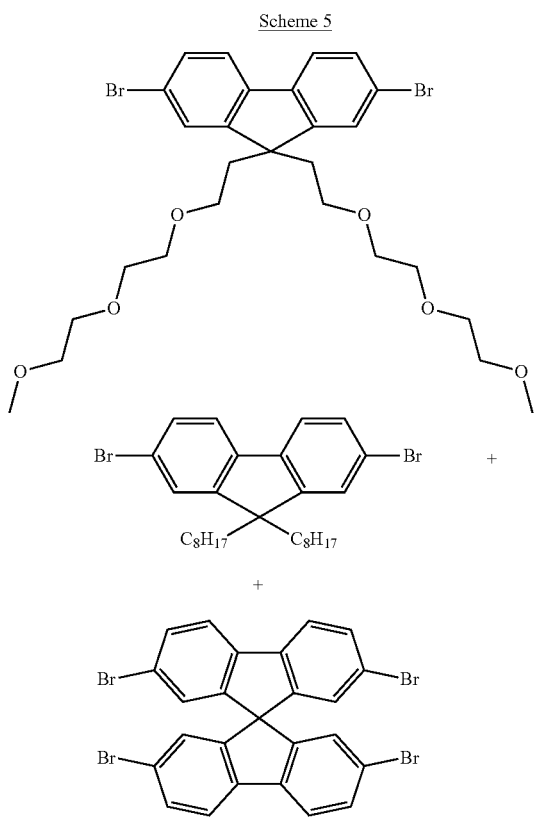

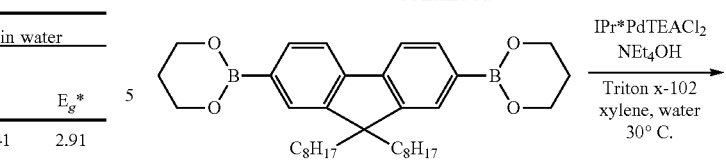

LM56

DLS Analysis (Nanoparticles in Water or THF)

Figure 10:
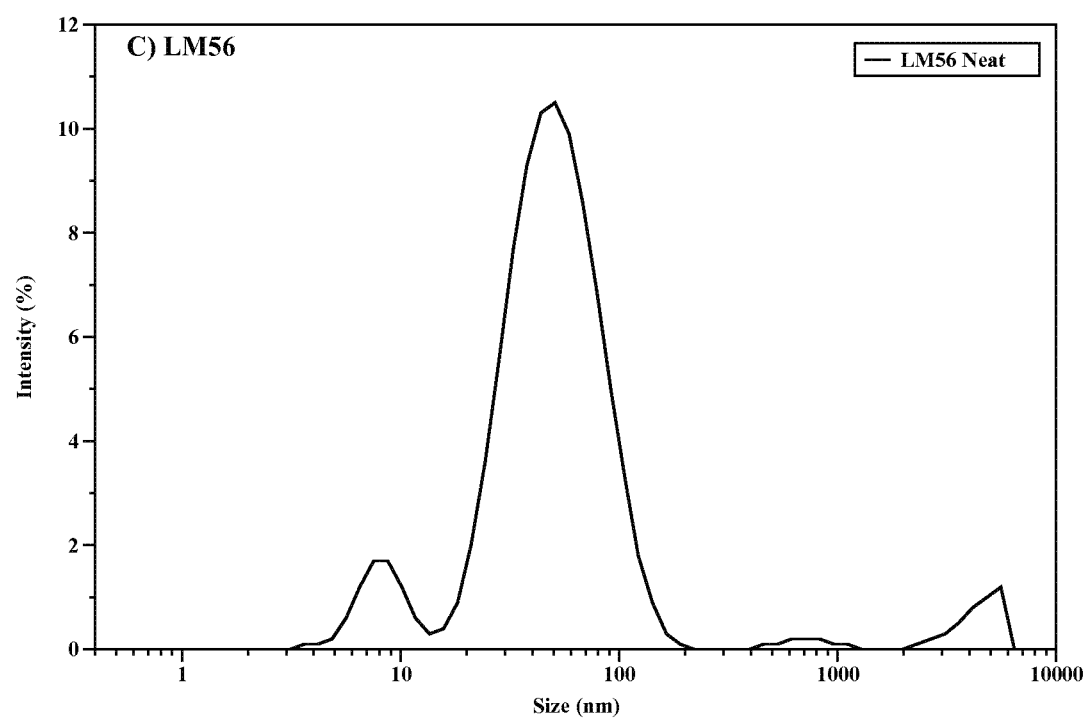
FIG. 10 shows DLS sizing histograms of the cross-linked nanoparticles of Example 1.5 in water.

500 µl of sample was transferred to centrifuge vial the 1.5 ml of methanol was added. The sample vial was centrifuged at 14,000 rpm for 5 min then the liquid was decanted. Crude sample was washed with methanol 3 times and re-dispersed in THF in order to measure the size of particles. Neat products without further purification were also investigated. The results are shown in FIG. 10 and Table 12. Concentrations of polymer in water was 23 µg/ml.

TABLE 12

Particle sizes of CPNs in water at 25° C.

| Sample | Size (nm) | Dz (nm) | STD (nm) | PdI |
|---|---|---|---|---|
| LM56 Neat | 55 | 41 | 26.23 | 0.381 |

Optical Properties

Referring to Table 13 and FIG. 12, LM56 showed absorption peak at 378 nm.

TABLE 13

Summarized optical properties of cross-linked polymer in water

| Sample | Final polymer conc. (mg/ml) | Size (nm) | $\lambda_{abs}$ (nm) | $\lambda_{em}$ (nm) | $E_g^*$ |
|---|---|---|---|---|---|
| LM56 | 2.5 | 55 | 378, 435 | 421, 436, 453 | 2.78 |

1.6—PEG12 Functionalised 10% Cross-Linked PFO Nanoparticles

Synthesis

Referring to Scheme 6 below, tetraethylammonium hydroxide solution (40% in water) (0.1567 g, 0.4 mmol), was added to an aqueous solution (50 ml) of non-ionic surfactant, Triton x-102 (2.5 g, 5 wt % in de-ionised water) in a 100 ml three necked round bottom flask. Then contents were then through degassed for 30 mins by bubbling nitrogen gas through the stirred solution. Then a separate 10 ml two necked round bottom flask was used to mix together the monomers in the organic solvent prior to addition to the reaction flask. 9,9-dioctylfluorene-2,7-di-boronic acid-bis(1,3-propanediol)ester (0.1151 g, 0.2 mmol), 2,7-dibromo-9,9-bis(polyethylene glycol monoether)fluorene (0.2255 g, 0.16 mmol) and 2,2',7,7'-tetrabromo-9,9'-spirobifluorene (0.0126 g, 0.02 mmol) were dissolved in xylene (2 ml). The monomer solution was degassed and then the catalyst IPr*PdTEACl₂ (0.0095 g, 0.008 mmol) was added, followed by further degassing of the resultant solution. A syringe was used to transfer the monomer/catalyst into the stirred surfactant/base solution in the main reaction flask now maintained at 30° C. with stirring and maintaining under nitrogen gas for 24 h.

DLS Analysis (Nanoparticles in Water or THF)

Figure 11:
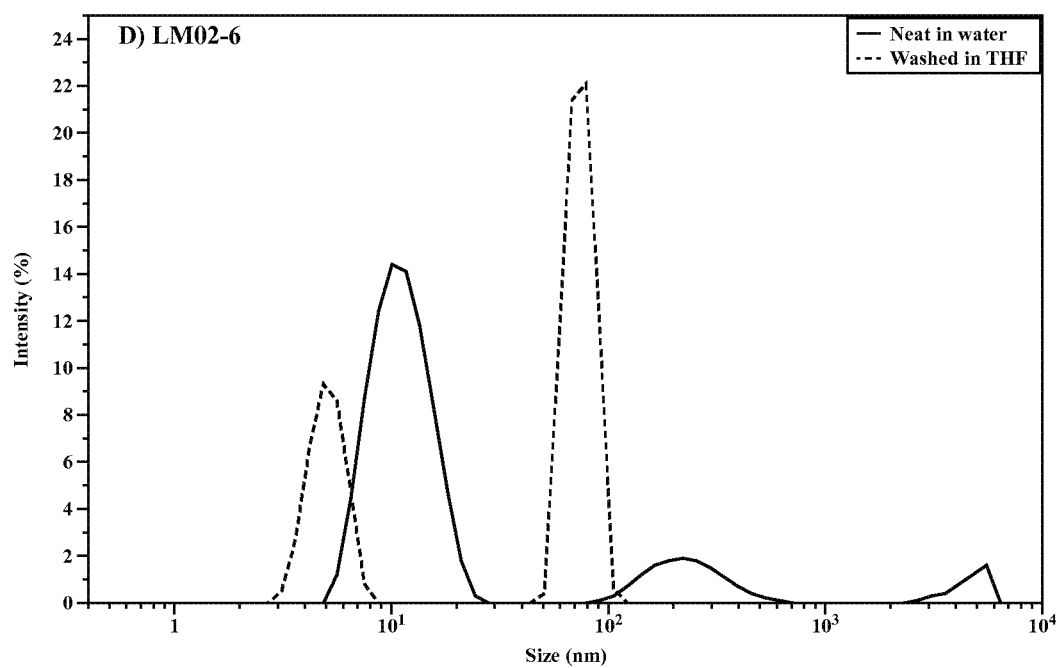
FIG. 11 shows DLS sizing histograms of the cross-linked nanoparticles of Example 1.6 in water (broken line) and THF (solid line).

500 μl of sample was transferred to centrifuge vial the 1.5 ml of methanol was added. The sample vial was centrifuged at 14,000 rpm for 5 min then the liquid was decanted. Crude sample was washed with methanol 3 times and re-dispersed in THF in order to measure the size of particles. Neat products without further purification were also investigated. The results are shown in FIG. 11 and Table 14. Concentrations of polymer in water was 23 μg/ml.

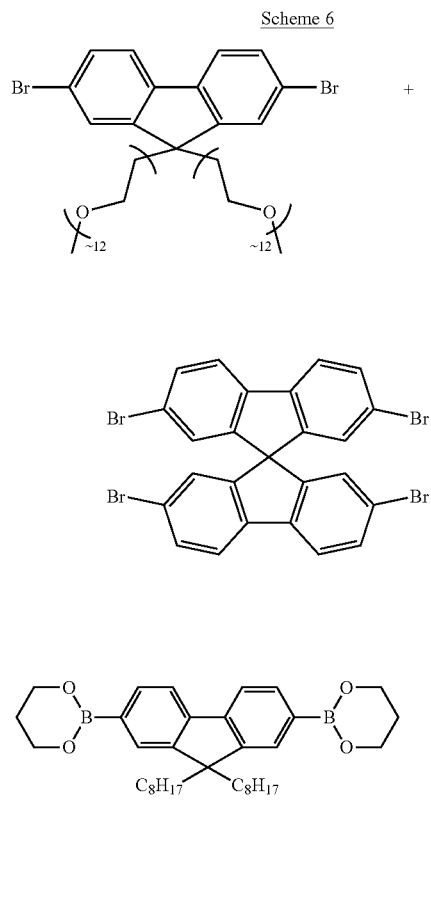

Scheme 6

LM02-6

TABLE 14

Particle sizes of CPNs in water and THF at 25° C.

| Sample | Size (nm) | Dz (nm) | STD (nm) | PdI |
|---|---|---|---|---|
| LM02-6 Neat | 244 | 13 | 103.2 | 0.359 |
| LM02-6 in THF | 74 | 847 | 10.97 | 0.489 |

Optical Properties

Table 15 and FIG. 12 show summarized optical properties for LM02-6 in water.

TABLE 15

Summarized optical properties of cross-linked polymer in water

| Sample | Final polymer conc. (mg/ml) | Size (nm) | $\lambda_{abs}$ (nm) | $\lambda_{em}$ (nm) | $E_g^*$ |
|---|---|---|---|---|---|
| LM02-6 | 2.5 | 244 | N/A | 419, 441 | N/A |

1.7-5% 2,1,3-Benzothiadiazole, 35% 9,9-Di(undecanoic acid)fluorene and 5% 9,9'-Spirobifluorene Cross-Linked Polyfluorene Nanoparticles Synthesis

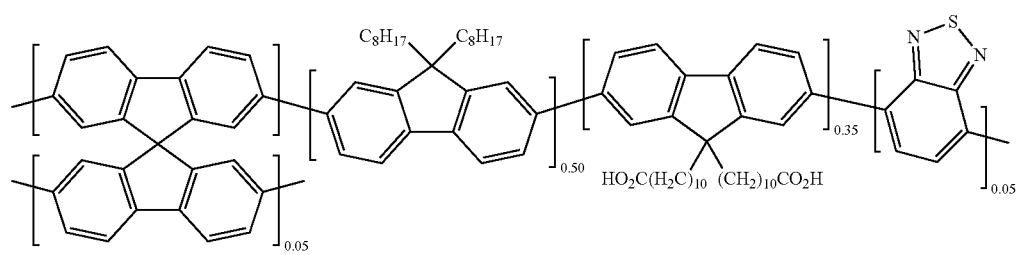

In a Schlenk tube was added water (22.0 mL), sodium dodecyl sulfate (110 mg, 382 µmol) and 1M aqueous sodium hydroxide (1080 µL, 1080 µmol). The solution was purged with argon for 2 hours. In a vial was weighed 9,9-dioctylfluorene-2,7-diboronic acid bis(1,3-propanediol) ester (111.7 mg, 200 µmol), 2,7-dibromo-9,9-di(undecanoic acid) fluorene (96.9 mg, 140 µmol), 2,2',7,7'-tetrabromo-9,9'-spirobifluorene (12.6 mg, 20 µmol), 4,7-dibromobenzo[c]-1,2,5-thiadiazole (5.9 mg, 20 µmol) tris(dibenzylideneacetone)dipalladium(0) (4.6 mg, 5 µmol), tri(o-tolyl)phosphine (9.1 mg, 30 µmol) and hexadecane (171 µL, 585 µmol). The vial was transferred to an argon filled glovebox, sealed with a rubber septum and removed. Toluene (2.19 mL) was added to the vial and the suspension sonicated until a homogenous solution was achieved. The initial aqueous solution was cooled to 0° C. in an ice bath, the ultrasonic probe inserted and the toluene solution injected rapidly into the water. The solution was ultrasonicated for 1 minute, stirred for 30 seconds and ultrasonicated for 1 further minute. The Schlenk tube was sealed, placed in a preheated oil bath at 50° C. and stirred for 20 hours. The Schlenk was opened and a stream of nitrogen gas passed over the emulsion at 50° C., with stirring. The emulsion was cooled to room temperature, the volume increased to 23.0 mL with deionised water and filtered through a glass wool plug. The emulsion was obtained as a milky dark green solution. DLS (water): Z-average=79.0 nm, PdI=0.117, $D_n$=52.4 nm and SD=15.3 nm. UV-Vis Abs. (water): $\lambda_{max}$=380 nm, $\lambda_{sec.}$=450 nm, $\lambda_{onset}$=520 nm. UV-Vis PL (water): $\lambda_{max}$=535 nm, $\lambda_{sec.}$=424 nm.

1.8-40% Di(t-butyl hexanoate)fluorene and 5% 9,9'-Spirobifluorene Cross-Linked Polyfluorene Nanoparticles Synthesis

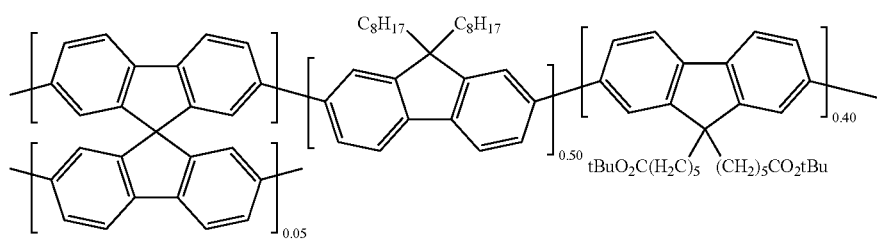

In a Schlenk tube was added water (22.0 mL), sodium dodecyl sulfate (110 mg, 382 µmol) and 1M aqueous sodium hydroxide (800 µL, 800 µmol). The solution was purged with argon for 2 hours. In a vial was weighed 9,9-dioctyl-9H-fluorene-2,7-diboronic acid bis(pinacol) ester (128.5 mg, 200 µmol), 2,7-dibromo-9,9-di(t-butyl hexanoate)fluorene (106.3 mg, 160 µmol), 2,2',7,7'-tetrabromo-9,9'-spirobifluorene (12.6 mg, 20 µmol), tetrakis (triphenylphosphine) palladium(0) (5.8 mg, 5 µmol) and hexadecane (171 µL, 585 µmol). The vial was transferred to an argon filled glovebox, sealed with a rubber septum and removed. Toluene (2.19 mL) was added to the vial and the suspension sonicated until a homogenous solution was achieved. The initial aqueous solution was cooled to 0° C. in an ice bath, the ultrasonic probe inserted and the toluene solution injected rapidly into the water. The solution was ultrasonicated for 1 minute, stirred for 30 seconds and ultrasonicated for 1 further minute. The Schlenk tube was sealed, placed in a preheated oil bath at 72° C. and stirred for 20 hours. The Schlenk was opened and a stream of nitrogen gas passed over the emulsion at 50° C., with stirring. The emulsion was cooled to room temperature, the volume increased to 23.0 mL with deionised water and filtered through a glass wool plug. The emulsion was obtained as a milky light green solution. DLS (water): Z-average=129 nm, PdI=0.226, $D_n$=64 nm and SD=23.4 nm. UV-Vis Abs. (water): $\lambda_{max}$=384 nm, $\lambda_{onset}$=441 nm. UV-Vis PL (water): $\lambda_{max}$=430 nm, $\lambda_{sec.}$=453 nm, $\lambda_{sec.}$=484 nm.

1.9-2% 9,9-Di(undecanoic acid)fluorene, 5% 2,1,3-Benzothiadiazole, 33% Di(hex-5-en-1-yl)fluorene and 5% 9,9'-Spirobifluorene Cross-Linked Polyfluorene Nanoparticles Synthesis

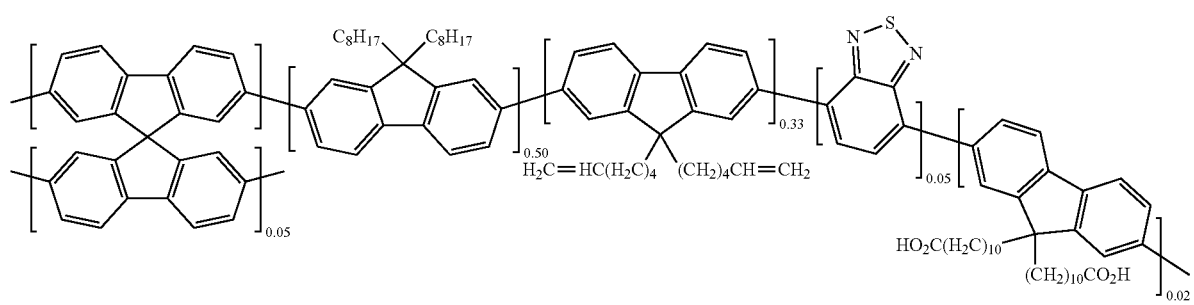

In a Schlenk tube was added water (22.0 mL), sodium dodecyl sulfate (110 mg, 382 µmol) and 1M aqueous sodium hydroxide (816 µL, 816 µmol). The solution was purged with argon for 2 hours. In a vial was weighed 9,9-dioctylfluorene-2,7-diboronic acid bis(1,3-propanediol) ester (111.7 mg, 200 µmol), 2,7-dibromo-9,9-di(undecanoic acid) fluorene (5.5 mg, 8 µmol), 2,2',7,7'-tetrabromo-9,9'-spirobifluorene (12.6 mg, 20 µmol), 4,7-dibromobenzo[c]-1,2,5-thiadiazole (5.9 mg, 20 µmol), 2,7-dibromo-9,9-di(hex-5-en-1-yl)fluorene (64.5 mg, 132 µmol), tris(dibenzylideneacetone)dipalladium(0) (4.6 mg, 5 µmol), tri(o-tolyl)phosphine (9.1 mg, 30 µmol) and hexadecane (171 µL, 585 µmol). The vial was transferred to an argon filled glovebox, sealed with a rubber septum and removed. Toluene (2.19 mL) was added to the vial and the suspension sonicated until a homogeneous solution was achieved. The initial aqueous solution was cooled to 0° C. in an ice bath, the ultrasonic probe inserted and the toluene solution injected rapidly into the water. The solution was ultrasonicated for 1 minute, stirred for 30 seconds and ultrasonicated for 1 further minute. The Schlenk tube was sealed, placed in a preheated oil bath at 50° C. and stirred for 20 hours. The Schlenk was opened and a stream of nitrogen gas passed over the emulsion at 50° C., with stirring. The emulsion was cooled to room temperature, the volume increased to 23.0 mL with deionised water and filtered through a glass wool plug. The emulsion was obtained as a milky dark green solution. DLS (water): Z-average=101 nm, PdI=0.166, $D_n$=55.1 nm and SD=18.1 nm. UV-Vis Abs. (water): $\lambda_{max}$=381 nm, $\lambda_{sec.}$=453 nm, $\lambda_{onset}$=522 nm. UV-Vis PL (water): $\lambda_{max}$=530 nm.

1.10. Synthesis of 5% Benzo[c]-1,2,5-thiadiazole, 45% 9,9-Di(sodium undecanyl sulfate)fluorene and 50% 9,9-Dioctyl(fluorene) Nanoparticles

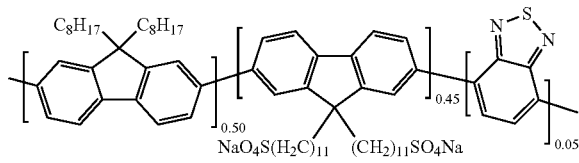

In a Schlenk tube was added water (22.0 mL), sodium dodecyl sulfate (110 mg, 382 µmol) and 1M aqueous sodium hydroxide (1080 µL, 1080 µmol). The solution was purged with argon for 2 hours. In a vial was weighed 9,9-dioctylfluorene-2,7-diboronic acid bis(1,3-propanediol) ester (111.7 mg, 200 µmol), 2,7-dibromo-9,9-di(sodium undecanyl sulfate)fluorene (156.4 mg, 180 µmol), 4,7-dibromobenzo[c]-1,2,5-thiadiazole (5.9 mg, 20 µmol) tris(dibenzylideneacetone)dipalladium(0) (4.6 mg, 5 µmol), tri(o-tolyl)phosphine (9.1 mg, 30 µmol) and hexadecane (171 µL, 585 µmol). The vial was transferred to an argon filled glovebox, sealed with a rubber septum and removed. Toluene (2.19 mL) was added to the vial and the suspension sonicated until a homogenous solution was achieved. The initial aqueous solution was cooled to 0° C. in an ice bath, the ultrasonic probe inserted and the toluene solution injected rapidly into the water. The solution was ultrasonicated for 1 minute, stirred for 30 seconds and ultrasonicated for 1 further minute. The Schlenk tube was sealed, placed in a preheated oil bath at 50° C. and stirred for 16 hours. The Schlenk tube was opened and a stream of nitrogen gas passed over the emulsion at 50° C., with stirring. The emulsion was cooled to room temperature, the volume increased to 23.0 mL with deionised water and filtered through a glass wool plug. The emulsion was obtained as a milky dark green solution.

1.11 -5% Benzo[c]-1,2,5-thiadiazole, 35% 9,9-Di(undecanoic acid)fluorene and 5% 9,9'-Spirobifluorene Cross-Linked Polyfluorene Nanoparticles Synthesis

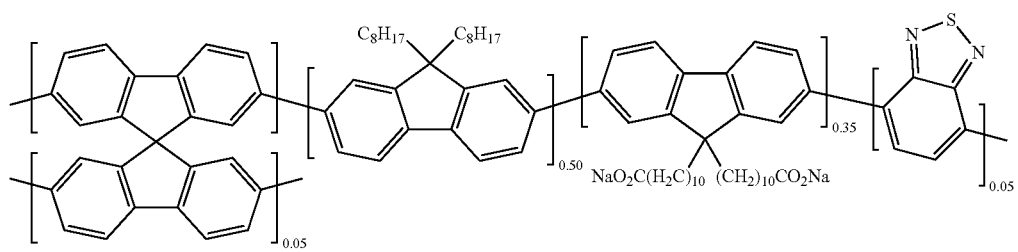

In a Schlenk tube was added water (22.0 mL), sodium dodecyl sulfate (110 mg, 382 µmol) and 1M aqueous sodium hydroxide (1080 µL, 1080 µmol). The solution was purged with argon for 2 hours. In a vial was weighed 9,9-dioctylfluorene-2,7-diboronic acid bis(1,3-propanediol) ester (111.7 mg, 200 µmol), 2,7-dibromo-9,9-di(undecanoic acid)fluorene (96.9 mg, 140 µmol), 2,2',7,7'-tetrabromo-9,9'-spirobifluorene (12.6 mg, 20 µmol), 4,7-dibromobenzo[c]-1,2,5-thiadiazole (5.9 mg, 20 µmol) tris(dibenzylideneacetone)dipalladium(0) (4.6 mg, 5 µmol), tri(o-tolyl)phosphine (9.1 mg, 30 µmol) and hexadecane (171 µL, 585 µmol). The vial was transferred to an argon filled glovebox, sealed with a rubber septum and removed. Toluene (2.19 mL) was added to the vial and the suspension sonicated until a homogenous solution was achieved. The initial aqueous solution was cooled to 0° C. in an ice bath, the ultrasonic probe inserted and the toluene solution injected rapidly into the water. The solution was ultrasonicated for 1 minute, stirred for 30 seconds and ultrasonicated for 1 further minute. The Schlenk tube was sealed, placed in a preheated oil bath at 50° C. and stirred for 20 hours. The Schlenk tube was opened and a stream of nitrogen gas passed over the emulsion at 50° C., with stirring. The emulsion was cooled to room temperature, the volume increased to 23.0 mL with deionised water and filtered through a glass wool plug. The emulsion was obtained as a milky dark green solution (CPN1). DLS (water): Z-average=79.0 nm, PdI=0.117, $D_n$=52.4 nm and SD=15.3 nm. UV-Vis Abs. (water): $\lambda_{max}$=380 nm, $\lambda_{sec.}$=450 nm, $\lambda_{onset}$=520 nm. UV-Vis PL (water): $\lambda_{max}$=535 nm, $\lambda_{sec.}$=424 nm.

1.12 -5% 9,9'-Spirobifluorene, 90% Di((4-((2-ethylhexyl)oxy)phenyl)) fluorene Nanoparticles

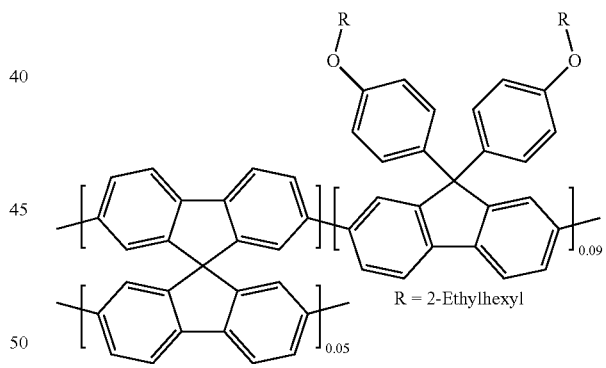

R = 2-Ethylhexyl

In a 250 mL round bottom flask, fitted with an argon inlet, was added water (100 mL), sodium hydroxide (160 mg, 4.00 mmol) and sodium dodecyl sulfate (551 mg) and the solution purged with argon for 1 hour. Toluene was degassed with argon for 2 hours. In a Schlenk tube was weighed 9,9-di((4-((2-ethylhexyl)oxy)phenyl))fluorene-2,7-diboronic acid bis(pinacol) ester (827 mg, 1.00 mmol), 2,7-dibromo-9,9-di((4-((2-ethylhexyl)oxy)phenyl))fluorene (513 mg, 700 µmol), 2,2',7,7'-tetrabromo-9,9'-spirobifluorene (63.2 mg, 100 µmol), hexadecane (855 µL), 4,7-dibromobenzo[c]-1,2,5-thiadiazole (29.4 mg, 100 µmol), tris(dibenzylideneacetone) dipalladium(0) (22.4 mg, 25 µmol) and tri(o-tolyl)phosphine (45.6 mg, 150 µmol). The Schlenk tube was subjected to four vacuum-argon cycles. Toluene (10 mL) was added and the suspension sonicated in an ultrasonic bath until a homogenous solution was achieved. The initial aqueous solution was cooled to 0° C. in an ice bath and the toluene solution was added rapidly into the aqueous phase under a stream of argon. A stirrer bar was added and the ultrasonic probe inserted (½" extender tip) to a depth of 2 cm. The solution was ultrasonicated for 2 minutes at 40% amplitude, stirred for 30 seconds then sonicated for 2 further minutes. The flask was sealed, placed in a preheated oil bath at 70° C. and stirred for 16 hours. The flask was cooled to 50° C. and air passed over the emulsion for 5 hours, with stirring. The emulsion was cooled to room temperature, left to stand for 16 hours and filtered through a glass wool plug. The emulsion was obtained as a bright green cloudy dispersion. DLS: z-Average: 115.9 nm, Pdl: 0.153. UV-Vis Abs. (water): $\lambda_{max}$=391 nm. UV-Vis PL (water): $\lambda_{max}$=422 nm.

1.13-5% 9,9'-Spirobifluorene, 10% Di((4-(sodium undecanoyl sulfate)phenyl))fluorene, 80% Di((4-((2-ethylhexyl)oxy)phenyl))fluorene Nanoparticles 1.14-5% Benzo[c]-1,2,5-thiadiazole, 5% 9,9'-Spirobifluorene, 85% Di((4-((2-ethylhexyl)oxy)phenyl)) fluorene Nanoparticles

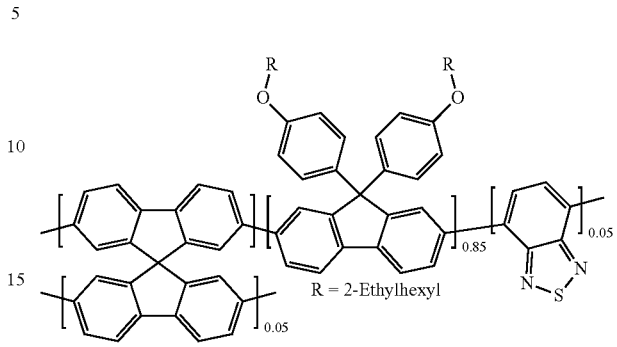

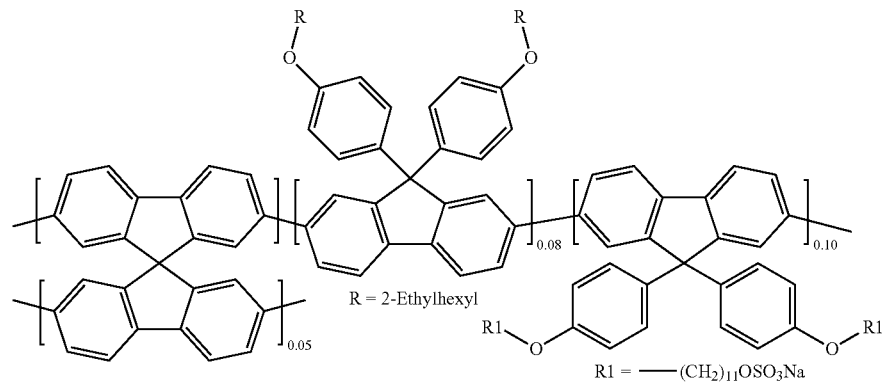

In a 250 mL round bottom flask, fitted with an argon inlet, was added water (100 mL), sodium hydroxide (160 mg, 4.00 mmol) and 2,7-dibromo-9,9-di((4-(sodium undecanoyl sulfate)phenyl))fluorene (211 mg, 200 μmol) and the solution purged with argon for 2 hours. Toluene was degassed with argon for 2 hours. In a Schlenk tube was weighed 9,9-di ((4-((2-ethylhexyl)oxy)phenyl))fluorene-2,7-diboronic acid bis(pinacol) ester (827 mg, 1.00 mmol), 2,7-dibromo-9,9-di ((4-((2-ethylhexyl)oxy)phenyl))fluorene (440 mg, 600 μmol), 2,2',7,7'-tetrabromo-9,9'-spirobifluorene (63.2 mg, 100 μmol), hexadecane (855 μL), tris(dibenzylideneacetone) dipalladium(0) (22.4 mg, 25 μmol) and tri(o-tolyl)phosphine (45.6 mg, 150 μmol). The Schlenk tube was subjected to four vacuum-argon cycles. Toluene (10 mL) was added and the suspension sonicated in an ultrasonic bath until a homogenous solution was achieved. A stirrer bar was added and the ultrasonic probe inserted (½" extender tip) to a depth of 2 cm. The solution was ultrasonicated for 2 minutes at 40% amplitude, stirred for 30 seconds then sonicated for 2 further minutes. The flask was sealed, placed in a preheated oil bath at 60° C. and stirred for 16 hours. The flask was cooled to 50° C. and air passed over the emulsion for 5 hours, with stirring. The emulsion was cooled to room temperature, left to stand for 16 hours and filtered through a glass wool plug. The emulsion was obtained as a dark green/grey cloudy dispersion. DLS: z-Average: 171.2 nm, Pdl: 0.047. UV-Vis Abs. (water): $\lambda_{max}$=398 nm. UV-Vis PL (water): $\lambda_{max}$=422 nm.

In a 250 mL round bottom flask, fitted with an argon inlet, was added water (100 mL), sodium hydroxide (160 mg, 4.00 mmol) and sodium dodecyl sulfate (551 mg) and the solution purged with argon for 1 hour. Toluene was degassed with argon for 2 hours. In a Schlenk tube was weighed 9,9-di((4-((2-ethylhexyl)oxy)phenyl))fluorene-2,7-diboronic acid bis(pinacol) ester (827 mg, 1.00 mmol), 2,7-dibromo-9,9-di((4-((2-ethylhexyl)oxy)phenyl))fluorene (513 mg, 700 μmol), 2,2',7,7'-tetrabromo-9,9'-spirobifluorene (63.2 mg, 100 μmol), hexadecane (855 μL), 4,7-dibromobenzo[c]-1,2,5-thiadiazole (29.4 mg, 100 μmol), tris(dibenzylideneacetone) dipalladium(0) (22.4 mg, 25 μmol) and tri(o-tolyl)phosphine (45.6 mg, 150 μmol). The Schlenk tube was subjected to four vacuum-argon cycles. Toluene (10 mL) was added and the suspension sonicated in an ultrasonic bath until a homogenous solution was achieved. The initial aqueous solution was cooled to 0° C. in an ice bath and the toluene solution was added rapidly into the aqueous phase under a stream of argon. A stirrer bar was added and the ultrasonic probe inserted (½" extender tip) to a depth of 2 cm. The solution was ultrasonicated for 2 minutes at 40% amplitude, stirred for 30 seconds then sonicated for 2 further minutes. The flask was sealed, placed in a preheated oil bath at 70° C. and stirred for 16 hours. The flask was cooled to 50° C. and air passed over the emulsion for 5 hours, with stirring. The emulsion was cooled to room temperature, left to stand for 16 hours and filtered through a glass wool plug. The emulsion was obtained as a bright green cloudy dispersion. DLS: z-Average: 115.1 nm, Pdl: 0.160. UV-Vis Abs. (water): $\lambda_{max}$=387 nm. UV-Vis PL (water): $\lambda_{max}$=526 nm.

1.15-5% Benzo[c]-1,2,5-thiadiazole, 5% 9,9'-Spiro-bifluorene, 10% Di((4-(sodium undecanoyl sulfate)phenyl))fluorene, 75% Di((4-((2-ethylhexyl)oxy)phenyl))fluorene Nanoparticles

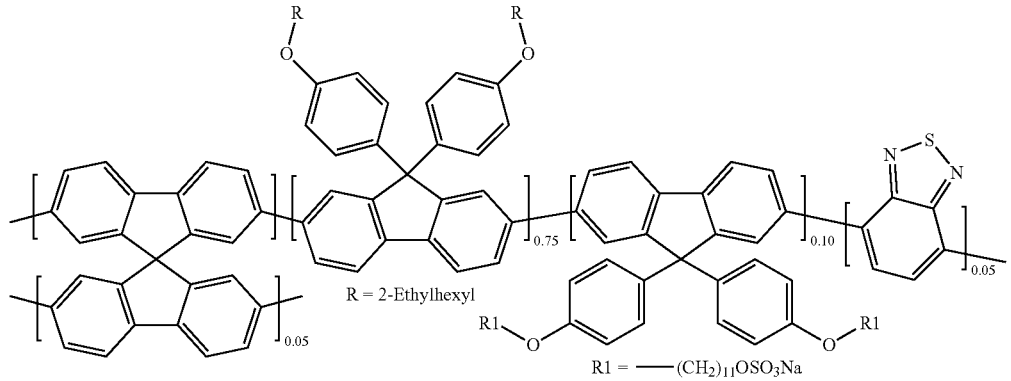

In a 250 mL round bottom flask, fitted with an argon inlet, was added water (100 mL), sodium hydroxide (160 mg, 4.00 mmol) and 2,7-dibromo-9,9-di((4-(sodium undecanoyl sulfate)phenyl))fluorene (211 mg, 200 µmol) and the solution purged with argon for 1 hour. Toluene was degassed with argon for 1 hours. In a Schlenk tube was weighed 9,9-di((4-((2-ethylhexyl)oxy)phenyl))fluorene-2,7-diboronic acid bis(pinacol) ester (827 mg, 1.00 mmol), 2,7-dibromo-9,9-di((4-((2-ethylhexyl)oxy)phenyl))fluorene (366 mg, 500 µmol), 2,2',7,7'-tetrabromo-9,9'-spirobifluorene (63.2 mg, 100 µmol), hexadecane (855 µL), 4,7-dibromobenzo[c]-1,2,5-thiadiazole (29.4 mg, 100 µmol), tris(dibenzylideneacetone) dipalladium(0) (22.4 mg, 25 µmol) and tri(o-tolyl)phosphine (45.6 mg, 150 µmol). The Schlenk tube was subjected to four vacuum-argon cycles. Toluene (10 mL) was added and the suspension sonicated in an ultrasonic bath until a homogenous solution was achieved. The initial aqueous solution was cooled to 0° C. in an ice bath and the toluene solution was added rapidly into the aqueous phase under a stream of argon. A stirrer bar was added and the ultrasonic probe inserted (½" extender tip) to a depth of 2 cm. The solution was ultrasonicated for 2 minutes at 40% amplitude, stirred for 30 seconds then sonicated for 2 further minutes. The flask was sealed, placed in a preheated oil bath at 70° C. and stirred for 16 hours. The flask was cooled to 50° C. and air passed over the emulsion for 5 hours, with stirring. The emulsion was cooled to room temperature, left to stand for 16 hours and filtered through a glass wool plug. The emulsion was obtained as a bright green cloudy dispersion. DLS: z-Average: 184.5 nm, PdI: 0.031. UV-Vis Abs. (water): $\lambda_{max}$=393 nm. UV-Vis PL (water): $\lambda_{max}$=527 nm.

1.16-5% Benzo[c]-1,2,5-thiadiazole, 5% 9,9'-Spiro-bifluorene, 75% 9,9-Dioctyl(fluorene), 10% 9,9-Di(poly(ethylene glycol) monomethyl ether$_{(Mn\ 900)}$)(fluorene)

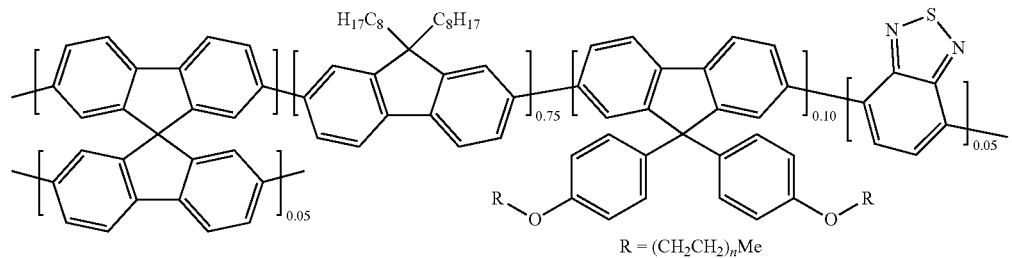

In a Schlenk tube was added water (20 mL) and sodium hydroxide (32.0 mg, 800 µmol) and the solution purged with argon for 2 hours. Toluene was degassed with argon for 2 hours. In a vial was weighed 9,9-di-n-octylfluorene-2,7-diboronic acid bis(propanediol) ester (111.7 mg, 200 µmol), 9,9-di-n-octyl-2,7-dibromofluorene (54.8 mg, 100 µmol), 2,2',7,7'-tetrabromo-9,9'-spirobifluorene (12.6 mg, 20 µmol), 2,7-dibromo-9,9-di((poly(ethylene glycol) monomethyl ether$_{(Mn\ 900)}$)phenyl))fluorene (86.3 mg, 40 µmol), 4,7-dibromobenzo[c]-1,2,5-thiadiazole (5.9 mg, 20 µmol), hexadecane (150 µL), tris(dibenzylideneacetone) dipalladium(0) (4.6 mg, 5 µmol) and tri(o-tolyl)phosphine (9.1 mg, 30 µmol). The vial was purged with argon for 30 minutes. Toluene (2.00 mL) was added and the suspension sonicated in an ultrasonic bath until a homogenous solution was achieved. The initial aqueous solution and cooled to 0° C. in an ice bath. The toluene solution was added rapidly into the aqueous phase under a stream of argon. A stirrer bar was added and the ultrasonic probe inserted (6 mm microtip) to a depth of 2 cm. The solution was ultrasonicated for 1 minute at 30% amplitude, stirred for 30 seconds and sonicated for 1 further minute. The flask was sealed, placed in a preheated oil bath at 40° C. and stirred for 20 hours. The flask was heated to 50° C. and air passed over the emulsion for 5 hours, with stirring. The emulsion was cooled to room temperature, left to stand for 16 hours and filtered through cotton mesh. The emulsion was obtained as a bright green cloudy dispersion.

1.17-5% Benzo[c]-1,2,5-thiadiazole, 5% 9,9'-Spirobifluorene, 74% 9,9-Dioctyl(fluorene), 10% 9,9-Di(sodium undecanoyl sulfate)(fluorene), 1% 9,9-Di(sodium undecanoyl carboxylate)(fluorene)

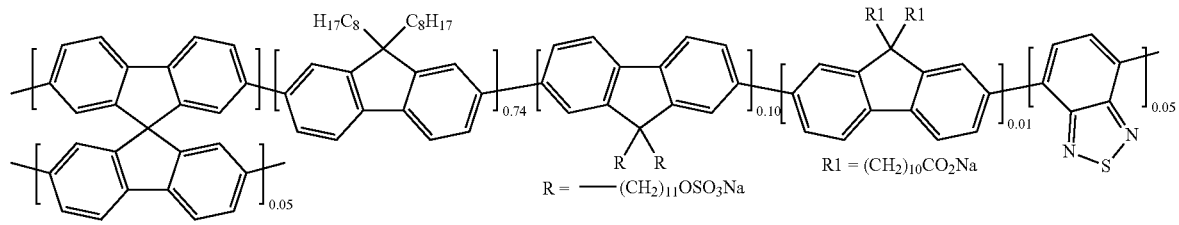

In a Schlenk tube was added water (20 mL) and sodium hydroxide (32.0 mg, 800 µmol) and the solution purged with argon for 2 hours. Toluene was degassed with argon for 2 hours. In a vial was weighed 9,9-di-n-octylfluorene-2,7-diboronic acid bis(propanediol) ester (111.7 mg, 200 µmol), 9,9-di-n-octyl-2,7-dibromofluorene (41.7 mg, 76 µmol), 2,2',7,7'-tetrabromo-9,9'-spirobifluorene (12.6 mg, 20 µmol), 2,7-dibromo-9,9-di(undecanoic acid)fluorene (2.8 mg, 4.0 µmol), 4,7-dibromobenzo[c]-1,2,5-thiadiazole (5.9 mg, 20 µmol), tris(dibenzylideneacetone) dipalladium(0) (4.6 mg, 5 µmol) and tri(o-tolyl)phosphine (9.1 mg, 30 µmol). The vial was purged with argon for 30 minutes. Toluene (2.00 mL) was added and the suspension sonicated in an ultrasonic bath until a homogenous solution was achieved. 9,9-Di(sodium undecanoyl sulfate)2,7-dibromofluorene (34.7 mg, 40 µmol) was added to the initial aqueous solution and cooled to 0° C. in an ice bath. The toluene solution was added rapidly into the aqueous phase under a stream of argon. A stirrer bar was added and the ultrasonic probe inserted (6 mm microtip) to a depth of 2 cm. The solution was ultrasonicated for 2 minutes at 30% amplitude, stirred for 30 seconds and this sequence repeated four further times. The flask was sealed, placed in a preheated oil bath at 40° C. and stirred for 20 hours. The flask was heated to 50° C. and air passed over the emulsion for 7 hours, with stirring. The emulsion was cooled to room temperature and filtered through a glass wool plug. The emulsion was obtained as a bright green cloudy dispersion.

1.18-5% Benzo[c]-1,2,5-thiadiazole, 5% 9,9'-Spirobifluorene, 70% 9,9-Dioctyl(fluorene), 10% 9,9-Di(sodium undecanoyl sulfate)(fluorene), 5% 9,9-Di(sodium undecanoyl carboxylate)(fluorene)

In a Schlenk tube was added water (20 mL) and sodium hydroxide (33.6 mg, 840 µmol) and the solution purged with argon for 2 hours. Toluene was degassed with argon for 2 hours. In a vial was weighed 9,9-di-n-octylfluorene-2,7-diboronic acid bis(propanediol) ester (111.7 mg, 200 µmol), 9,9-di-n-octyl-2,7-dibromofluorene (43.9 mg, 80 µmol), 2,7-dibromo-9,9-di(undecanoic acid)fluorene (13.9 mg, 20.0 µmol), 2,2',7,7'-tetrabromo-9,9'-spirobifluorene (12.6 mg, 20 µmol), 4,7-dibromobenzo[c]-1,2,5-thiadiazole (5.9 mg, 20 µmol), hexadecane (150 µL), tris(dibenzylideneacetone) dipalladium(0) (4.6 mg, 5 µmol) and tri(o-tolyl)phosphine (9.1 mg, 30 µmol). The vial was purged with argon for 30 minutes. Toluene (2.00 mL) was added and the suspension sonicated in an ultrasonic bath until a homogenous solution was achieved. 9,9-Di(sodium undecanoyl sulfate)2,7-dibromofluorene (34.7 mg, 40 µmol) was added to the initial aqueous solution and cooled to 0° C. in an ice bath. The toluene solution was added rapidly into the aqueous phase under a stream of argon. A stirrer bar was added and the ultrasonic probe inserted (6 mm microtip) to a depth of 2 cm. The solution was ultrasonicated for 2 minutes at 30% amplitude, stirred for 30 seconds and this sequence repeated four further times. The flask was sealed, placed in a preheated oil bath at 40° C. and stirred for 20 hours. The flask was heated to 50° C. and air passed over the emulsion for 5 hours, with stirring. The emulsion was cooled to room temperature and filtered through a glass wool plug. The emulsion was obtained as a bright green slightly cloudy dispersion. DLS: z-Average: 77.1 nm, PdI: 0.211.

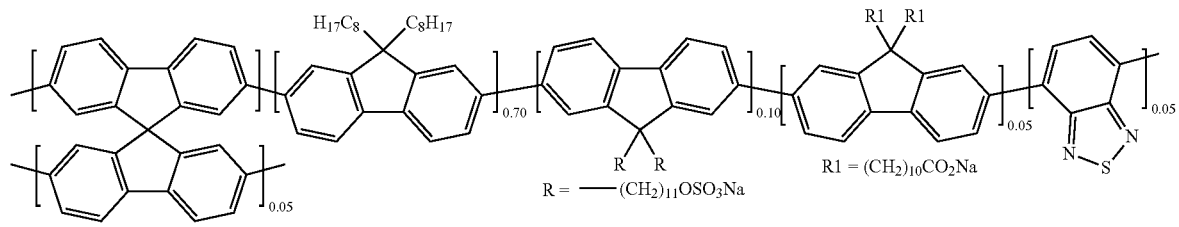

1.19—5% Benzo[c]-1,2,5-thiadiazole, 5% 9,9'-Spirobifluorene, 70% 9,9-Dioctyl(fluorene), 10% 9,9-Di(sodium undecanoyl sulfate)(fluorene), 5% 9,9-Di(sodium undecanoyl carboxylate)(fluorene)

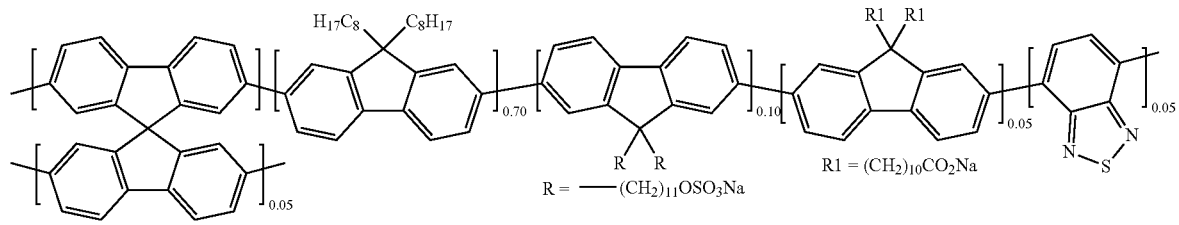

In a Schlenk tube was added water (20 mL) and sodium hydroxide (33.6 mg, 840 µmol) and the solution purged with argon for 2 hours. Toluene was degassed with argon for 2 hours. In a vial was weighed 9,9-di-n-octylfluorene-2,7-diboronic acid bis(propanediol) ester (111.7 mg, 200 µmol), 9,9-di-n-octyl-2,7-dibromofluorene (43.9 mg, 80 µmol), 2,7-dibromo-9,9-di(undecanoic acid)fluorene (13.9 mg, 20.0 µmol), 2,2',7,7'-tetrabromo-9,9'-spirobifluorene (12.6 mg, 20 µmol), 4,7-dibromobenzo[c]-1,2,5-thiadiazole (5.9 mg, 20 µmol), tris(dibenzylideneacetone) dipalladium(0) (4.6 mg, 5 µmol) and tri(o-tolyl)phosphine (9.1 mg, 30 µmol). The vial was purged with argon for 30 minutes. Toluene (2.00 mL) was added and the suspension sonicated in an ultrasonic bath until a homogenous solution was achieved. 9,9-Di(sodium undecanoyl sulfate)2,7-dibromofluorene (34.7 mg, 40 µmol) was added to the initial aqueous solution and cooled to 0° C. in an ice bath. The toluene solution was added rapidly into the aqueous phase under a stream of argon. A stirrer bar was added and the ultrasonic probe inserted (6 mm microtip) to a depth of 2 cm. The solution was ultrasonicated for 2 minutes at 30% amplitude, stirred for 30 seconds and this sequence repeated four further times. The flask was sealed, placed in a preheated oil bath at 40° C. and stirred for 20 hours. The flask was heated to 50° C. and air passed over the emulsion for 5 hours, with stirring. The emulsion was cooled to room temperature and filtered through a glass wool plug. The emulsion was obtained as a bright green clear dispersion. DLS: z-Average: 67.6 nm, Pdl: 0.237. UV-Vis Abs. (water): $\lambda_{max}$=375 nm. UV-Vis PL (water): $\lambda_{max}$=536 nm.

EXAMPLE 2—PREPARATION OF CONJUGATES

2.1—Transfer of Nanoparticle Solution CNP1 to MES Buffer (pH 6.1, 50 mM)

To nanoparticle solution CNP1 (Example 1.11) (2.00 mL) was added MES buffer (8.00 mL (pH 6.1, 50 mM)). The solution was transferred to a 'Vivapore 10/20 static concentrator' and the volume reduced to 1.0 mL. MES buffer (9.00 mL (pH 6.1, 50 mM)) was added and the solution transferred to a 'second vivapore 10/20 static concentrator' and the volume reduced to 1 mL. The volume was increased to 10.0 mL with MES buffer (9.00 mL (pH 6.1, 50 mM)) to give nanoparticle solution CNP2 (1.16 mg mL$^{-1}$, 61 µM, 2.0 µmol mL$^{-1}$ CO$_2$H).

2.2—Nanoparticle Activation with N-(3-Dimethylaminopropyl)-N'-ethylcarbodiimide hydrochloride and N-hydroxysulfosuccinimide To nanoparticle solution CPN1 (Example 1.11) (5.00 mL, 1.16 mg mL$^{-1}$, 61 µM, 2.0 µmol mL$^{-1}$ CO$_2$H) was added N-(3-Dimethylaminopropyl)-N'-ethylcarbodiimide hydrochloride (1.9 mg, 10 µmol) and N-hydroxysulfosuccinimide (4.3 mg, 20 µmol). The solution was stirred for 30 mins then MES buffer (5.00 mL (pH 6.1, 50 mM)) was added. The solution was transferred to a 'Vivapore 10/20 static concentrator' and the volume reduced to 0.5 mL. MES buffer (9.50 mL (pH 6.1, 50 mM)) was added and transferred to a second 'vivapore 10/20 static concentrator' and the volume reduced to 0.5 mL. MES buffer (4.50 mL (pH 6.1, 50 mM)) was added to give the EDC/NHS activated nanoparticles (CPN2) (1.08 mg mL$^{-1}$, 57 µM and (1.9 µmol mL$^{-1}$ CO$_2$H)).

2.3—Bioconjugation of Nanoparticles to Streptavidin

Figure 13:
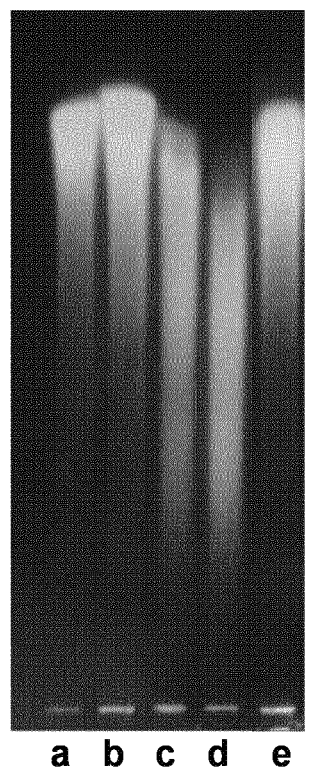
FIG. 13 shows electrophoresis gel of Nanoparticles conjugated to Streptavidin.

FIG. 13 shows the following nanoparticle samples:
Sample a: Nanoparticle solution CPN 1.
Sample b: Nanoparticle solution CPN2, mixed for 18 hours.
Sample c: Nanoparticle solution CPN 2 (400 µL, 22.8 µmol) was mixed for 16 hours, then quenched with glycine (3.8 µL of 200 µM solution, 0.76 µmol) and mixed for a further 2 hours.
Sample d: To nanoparticle solution CPN2 (332 µL, 18.9 µmol) was added streptavidin (10 µL, 189 µmol (18.9 µM solution in PBS buffer pH 7.2, 12 mM)) and mixed for 16 hours at RT. Glycine (3.2 µL of 200 µM solution, 0.63 µmol) was added and the solution mixed for a further 2 hours.
Sample e: Nanoparticle solution CPN1 (310 µL, 18.9 µmol) was mixed with streptavidin (10 µL, 189 µmol (18.9 µM solution in PBS buffer pH 7.2, 12 mM)) and mixed for 18 hours.

Figure 14:
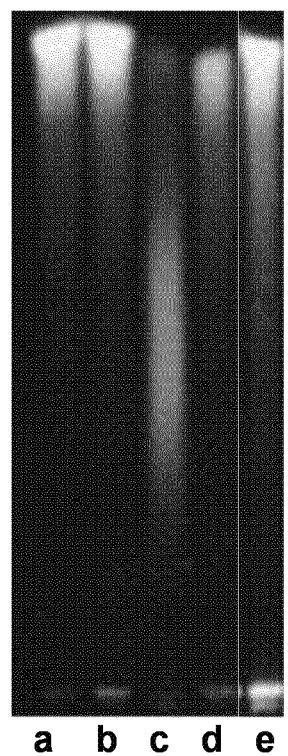
FIG. 14 shows electrophoresis gel of Nanoparticles conjugated to donkey anti-mouse IgG (H+L) secondary antibody.

2.4—Bioconjugation of Nanoparticles to Donkey Anti-Mouse IgG (H+L) Secondary Antibody FIG. 14 shows the following nanoparticle samples:
Sample a: Nanoparticle solution CPN1.
Sample b: Nanoparticle solution CPN2, mixed for 18 hours.
Sample c: Nanoparticle solution CPN2 (400 µL, 22.8 µmol) was mixed for 16 hours, then quenched with glycine (3.8 µL of 200 µM solution, 0.76 µmol) and stirred for a further 2 hours.
Sample d: To nanoparticle solution CPN2 (233 µL, 13.3 µmol) was added the secondary antibody (10 µL, 133 µmol (13.3 μM solution in PBS buffer pH 7.4, 12 mM)) and mixed for 16 hours at RT. Glycine (2.2 μL of 200 μM solution, 0.44 μmol) was added and the solution mixed for a further 2 hours.

Sample e: Nanoparticle solution CPN1 (218 μL, 13.3 μmol) was mixed with the secondary antibody (10 μL, 133 μmol (13.3 μM solution in PBS buffer pH 7.4, 12 mM)) and mixed for 18 hours.

2.5—Nanoparticle Activation with N-(3-Dimethyl-aminopropyl)-N'-ethylcarbodiimide hydrochloride (EDC)/N-hydroxysulfosuccinimide (NHS) and Subsequent Coupling Step 1. EDC/NHS Activation of Nanoparticles

| Component | Activated-Nanoparticles | Control |
|---|---|---|
| Nanoparticles (7 mg/ml, $CO_2H$ 1.8 umol/mL, size = 76 nm, Abs = 375 nm, Em = 536 nm, | 72 | 72 |
| 4 mM Stock EDC | 100 | — |
| 10 mM Stock NHS | 100 | — |
| MES buffer (50 mM pH 6.1) | 228 | 428 |
| Total Volume | 500 | 500 |

The above volumes were mixed and incubated for 15 mins.

The above reactions were then desalted using PD10 columns (desalting Sephadex G-25) pre-equilibrated in HEPES buffer (10 mM HEPES, 150 mM NaCl, pH7.4) and the fluorescent (green) fractions were collected (~1.0 ml). The flow-through and other fractions were non-fluorescent.

The proteins were desalted in PD10 columns equilibrated in HEPES buffer (10 mM HEPES, 150 mM NaCl, pH7.4):
(i) Streptavidin-Cy5 stock (16 uM) (Cy5-SA) was ×4 diluted in HEPES (100 uL+300 uL HEPES) and also desalted in a PD10 column in HEPES. Final concentration 3 uM.
(ii) Anti-Goat-IgG-HRP (IgG1) 250 uL+250 uL HEPES
(iii) Anti-biotin-IgG-AKP (IgG2) 100 uL+400 uL HEPES
(iii) PerCP in 500 uL (2 mg/mL).
(iv) A stock 5 mg/mL Biotin-Cadaverine (Bt-Cad) 1 mg/200 uL HEPES (11 mM)

Final volumes of fluorescent fractions were collected (~600 uL).

Step 2. Coupling Reactions with EDC-NHS Activated Nanoparticles

The desalted samples were coupled as follows:

| Coupling Reaction | Activated Luminspheres ™ (uL) | Stock Protein/NH$_2$ (uL) |
|---|---|---|
| Luminspheres ™ with Cy5-SA | Activated Rxn-Luminspheres ™ 200 | Cy5-SA 200 |
| Luminspheres ™ with Bt-Cad | Activated Rxn-Luminspheres ™ 200 | Bt-Cad 200 |
| Luminspheres ™ with IgG1 | Activated Rxn-Luminspheres ™ 200 | IgG1 200 |
| Luminspheres ™ with IgG2 | Activated Rxn-Luminspheres ™ 200 | IgG2 200 |
| PerCP | Activated Rxn-Luminspheres ™ 200 | PerCP 200 |

Each 400 uL reaction was incubated for 2 hours at room temperature before addition of 10 uL of 1M ethanolamine. The reaction was then stored at 4° C. overnight.

Step 3. EDC-NHS Activated Nanoparticles Coupling Reaction Evaluation.

Streptavidin-HP SpinTrap columns (highly cross-linked Agarose, 6%) were pre-equilibrated in HEPES (10 mM HEPES, 150 mM NaCl, pH7.4)
(i) Diluted ×10 Biotinylated-Nanoparticles in HEPES (50 uL=450 uL HEPES)-loaded 400 uL on to spin column.
(ii) Used a ×60 dilution of Nanoparticles-control (Nanoparticles only 50 uL=450 uL HEPES)-loaded 400 uL on to spin column.
(iii) Incubated at room temperature for 1 hour.
(iv) Measured fluorescence of supernatant after incubation: Biotinylated-Nanoparticles=100 RFU, Luminspheres™-control=240 RFU. Indicating that more of Biotinylated-Luminspheres™ bound specifically to the streptavidin-conjugated agarose beads.
(v) Washed both spin columns with HEPES (0.5 mL) the flow through and washes were not fluorescent.

2.6—Synthesis of 5% Benzo[c]-1,2,5-thiadiazole, 5% 9,9'-Spirobifluorene, 70% 9,9-Dioctyl(fluorene), 10% 9,9-Di(sodium undecanoyl sulfate)(fluorene), 5% 9,9-Di(biotin-undecanoate)(fluorene)

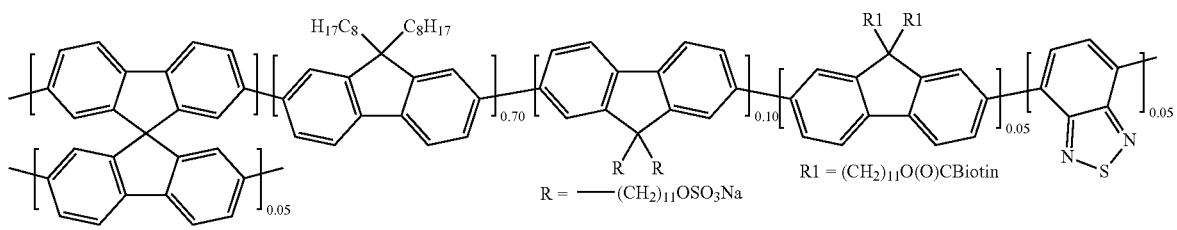

In a Schlenk tube was added water (20 mL) and sodium hydroxide (32.0 mg, 800 μmol) and the solution purged with argon for 2 hours. Toluene was degassed with argon for 2 hours. In a vial was weighed 9,9-di-n-octylfluorene-2,7-diboronic acid bis(propanediol) ester (111.7 mg, 200 μmol), 9,9-di-n-octyl-2,7-dibromofluorene (43.9 mg, 80 μmol), 9,9-di(biotin-undecanoate)dibromofluorene (22.3 mg, 20.0 μmol), 2,2',7,7'-tetrabromo-9,9'-spirobifluorene (12.6 mg, 20 μmol), 4,7-dibromobenzo[c]-1,2,5-thiadiazole (5.9 mg, 20 μmol), tris(dibenzylideneacetone) dipalladium(0) (4.6 mg, 5.0 μmol) and tri(o-tolyl)phosphine (9.1 mg, 30 μmol). The vial was purged with argon for 30 minutes. Toluene (2.00 mL) was added and the suspension sonicated in an ultrasonic bath until a homogenous solution was achieved. 9,9-Di(sodium undecanoyl sulfate)2,7-dibromofluorene (34.7 mg, 40 μmol) was added to the initial aqueous solution and cooled to 0° C. in an ice bath. The toluene solution was added rapidly into the aqueous phase under a stream of argon and the ultrasonic probe inserted (6 mm microtip) to a depth of 2 cm. The solution was ultrasonicated for 2 minutes at 30% amplitude, stirred for 30 seconds and this sequence repeated four further times. A stirrer bar was added, the flask was sealed, placed in a preheated oil bath at 40° C. and stirred for 20 hours. The flask was heated to 50° C. and air passed over the emulsion for 5 hours, with stirring. The emulsion was cooled to room temperature, centrifuged at 4,000 rpm for 5 minutes and filtered through a glass wool plug to provide a bright green dispersion (measured mass of emulsion: 23.00 g. Expected concentration: 7.18 mg/mL).

2.7—Nanoparticle-Cell Flow and Imaging Cytometry

Cell Culture and Incubation of Nanoparticles

HEK293 cells were plated into a 6 well plate and allowed to grow to full confluency. A log dilution of nanoparticle (7 mg/ml, $CO_2H$ 1.8 umol/mL, size=76 nm, Abs=375 nm, Em=536 nm) suspension was made in cell culture media (supplemented DMEM) from $1:10^2$ to $1:10^6$. Media was aspirated from the cells and replaced with media containing the nanoparticle suspension. One well had growth media without nanoparticles to act as the control well. Cells were incubated for 55 minutes at 37° C./5% $CO_2$ to allow potential binding/uptake of the nanoparticles. Nanoparticles were aspirated from the cells and they were washed twice in PBS. Cells were recovered from the plate by incubation with 0.2 mL Trypsin-EDTA for 5 minutes, 0.3 mL PBS+5% BSA was added to the cells and they were detached with gentle pipetting in 0.5 mL final volume.

Flow Cytometry Analysis

Cells were filtered through a 50 um mesh to remove aggregates into a 5 mL polypropylene round bottom tube. To identify dead cells the viability marker TOPRO-3 was added at a dilution of 1-500. Cells were run on a BD Influx cell sorter with 355, 488, 405, 561 and 647 nm laser line excitation using settings determined by running unlabelled cells. Live cells were identifies from cell debris and dead cell, and 20,000 cells were recorded. Following flow cytometry the sample with the optimal positive signal was chosen to analyse on the Amnis ImageStream imaging cytometer.

Figure 15:
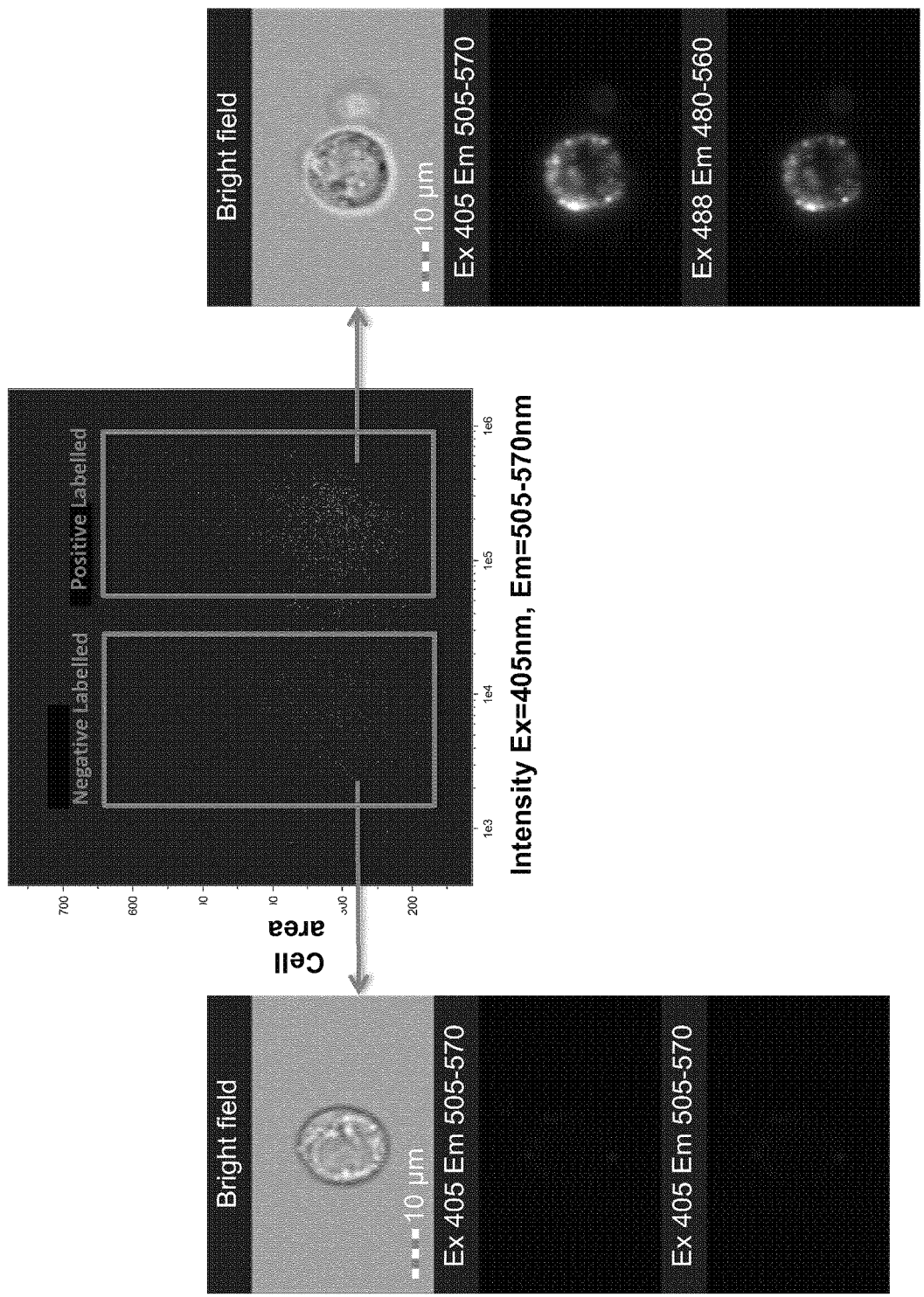
FIG. 15 shows images obtained by imaging cytometry (example 2.7)

Imaging Cytometry 100 ul of cell suspension was placed in a 1.5 mL eppendorff tube and loaded onto the ISX imaging cytometer. Using 488 (100 mW power setting) and 405 nm (20 mW power setting) excitation cells were identified above beads and 1000 cells were recorded in the bright field, side scatter and two fluorescence emission channels selected to be optimal to the nanoparticles emission, with 40× magnification. Data was analysed using IDEAS v6 software (see FIG. 15).

While specific embodiments of the invention have been described herein for the purpose of reference and illustration, various modifications will be apparent to a person skilled in the art without departing from the scope of the invention as defined by the appended claims.

The invention claimed is:

1. A conjugate comprising a drug molecule, biological molecule or cell bound to a photoluminescent polymer nanoparticle,
   wherein the drug molecule, biological molecule or cell is bound to the photoluminescent polymer nanoparticle by
   a covalent bond formed by the reaction of functional groups present on the photoluminescent polymer nanoparticle with functional groups present on the drug molecule, biological molecule or cell;
   and wherein the photoluminescent polymer nanoparticle is formed from a π-conjugated cross-linked polymer or a salt thereof, the π-conjugated cross-linked polymer comprising
   a) 80-99.9 mol. % of π-conjugated monomers, and
   b) 0.1-10 mol. % of a cross-linker having the formula III shown below:

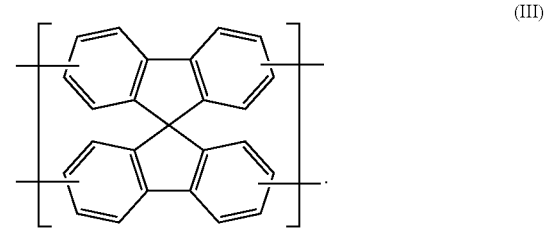

(III)

and
   c) one or more functional groups capable of reacting with functional groups on the drug molecule, biological molecule or cell to form a covalent bond linking the nanoparticle to the drug molecule, biological molecule or cell or a first moiety capable of affinity pairing with a second moiety present on the drug molecule, biological molecule or cell;
   wherein the π-conjugated monomers each independently have a structure according to formula IV shown below:

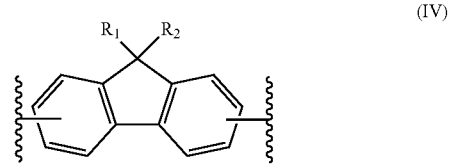

(IV)

wherein $R_1$ and $R_2$ are each independently hydrogen or a group:
   —X-Q
   wherein
   X is absent or selected from the group consisting of (1-30C)alkylene, —O-(1-30C)alkylene, —S-(1-30C)alkylene, —NH-(1-30C)alkylene, (2-30C)alkenylene, (2-30C)alkynylene, —[$(CH_2)_2$—O]$_n$—, —[O—(CH$_2$)$_2$]$_n$—, —[O—CH$_2$MeCH$_2$]$_n$—, —[CH$_2$MeCH$_2$—O]$_n$— and —[O—Si(R$_z$)$_2$]$_n$, wherein R$_z$ is (1-4C)alkyl and n is 1 to 30, —[(CH$_2$)$_{n'}$—(CF$_2$)$_{m'}$]—, wherein n' is 0-20 and m' is 1 to 30; and Q is a terminal group selected from the following substituents, or a salt thereof: hydrogen, halogen, methyl, hydroxyl, carboxy, (1-4C)alkoxycarbonyl, amino, —CH=CH$_2$, —C≡CH, —SH, biotin, streptavidin, antibody, —CF$_3$, —OSO$_3$H, —SO$_3$H, —OPO$_2$OH and zwitterions and a polymerisable group selected from silane, siloxane, acrylate, epoxy, styrene;

or R$_1$ and R$_2$ are aryl or heteroaryl groups optionally substituted with a substituent group;

or R$_1$ and R$_2$ are linked so that, together with the carbon atom to which they are attached, they form ring system optionally substituted with a substituent group;

and with the proviso that, in at least one monomer of formula IV, Q is or comprises a group selected from the following substituents, or a salt thereof: amino, carboxy, hydroxyl, halogen, vinyl, alkenyl, alkynyl, carbonyl, thiol, biotin, streptavidin, an antibody or a polymerisable group selected from acrylate, epoxy, and styrene.

2. The conjugate of claim 1, wherein the covalent bond is selected from an amide, disulphide, ether, thioether, amine, imine, enamine or ester linkage.

3. The conjugate of claim 1, wherein the photoluminescent polymer nanoparticle comprises:

(i) one or more hydroxyl groups that are capable of reacting with carboxy groups present on the drug molecule, biological molecule or cell to form ester bonds that couple the polymeric nanoparticle to the drug molecule, biological molecule or cell;

(ii) one or more amino groups that can react with carboxy groups present on the drug molecule, biological molecule or cell to form amide bonds that couple the polymeric nanoparticle to the drug molecule, biological molecule or cell;

(iii) one or more carboxy groups that can react with amino groups present on the drug molecule, biological molecule or cell to form amide bonds that couple the polymeric nanoparticle to the drug molecule, biological molecule or cell;

(iv) one or more thiol groups that can react with thiol groups present on the drug molecule, biological molecule or cell to form disulphide bonds that couple the polymeric nanoparticle to the drug molecule, biological molecule or cell;

(v) one or more vinyl groups that can react with thiol groups present on the drug molecule, biological molecule or cell to form sulphide bonds that couple the polymeric nanoparticle to the drug molecule, biological molecule or cell; and/or (vi) one or more carbonyl groups that can react with amine groups present on the drug molecule, biological molecule or cell to form imine or enamine bonds that couple the polymeric nanoparticle to the drug molecule, biological molecule or cell.

4. The conjugate of claim 1, wherein the π-conjugated monomers each independently have a structure according to formula V or VI shown below:

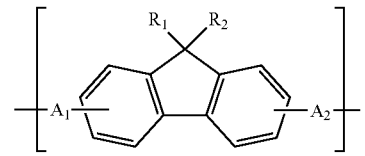

(V)

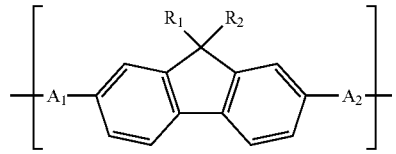

(VI)

wherein

R$_1$ and R$_2$ are as defined in claim 1; and

—X-Q

A$_1$ and A$_2$ are independently absent or selected from any one of the following moieties:

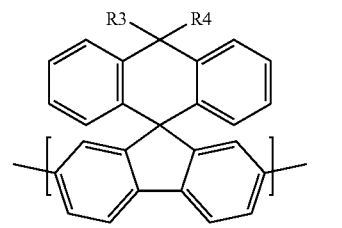

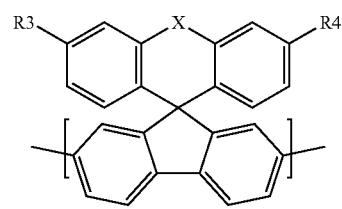

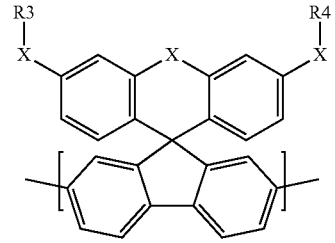

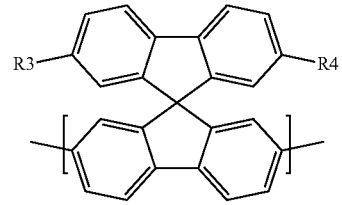

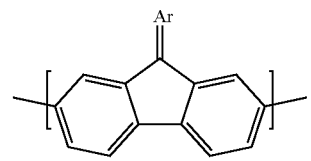

-continued
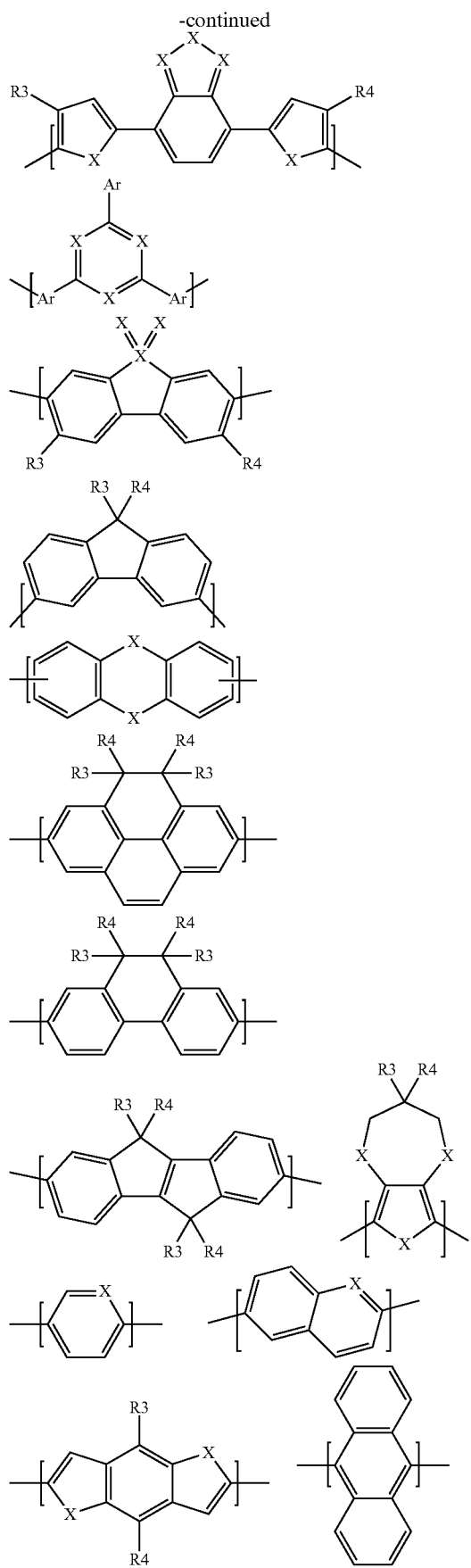
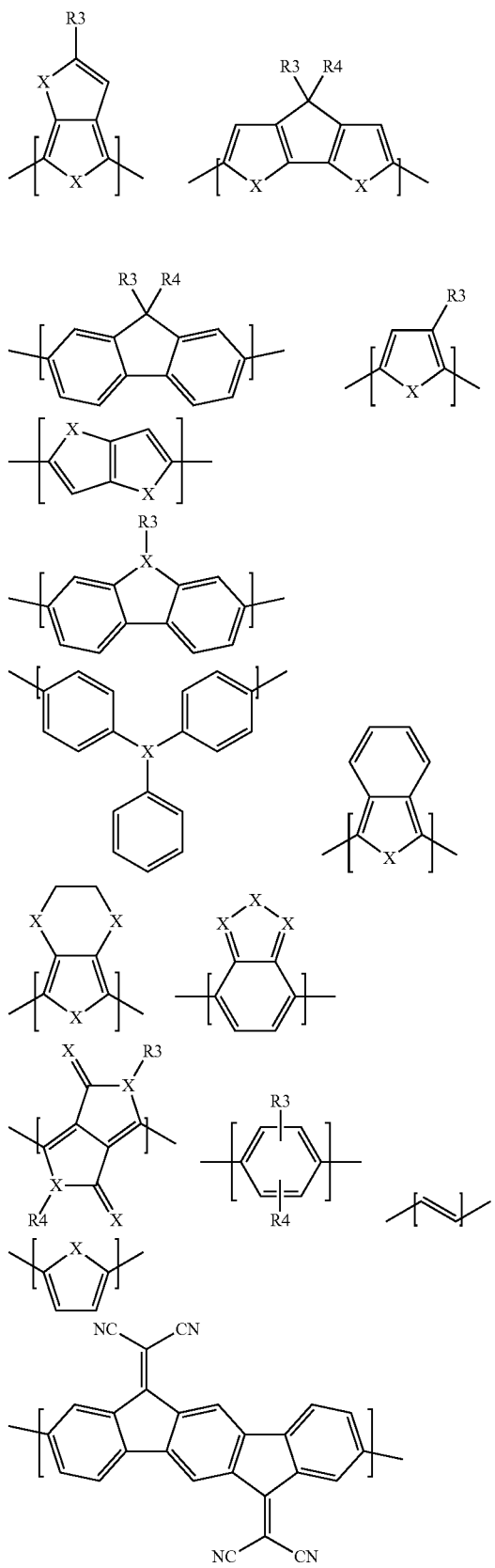

-continued

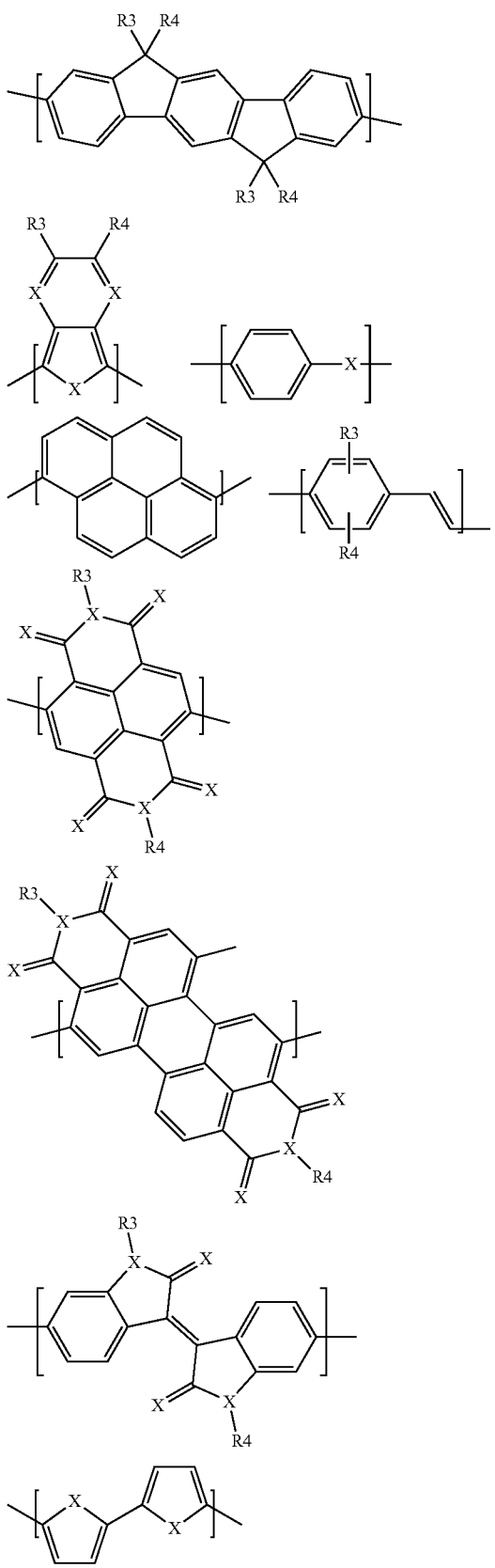

-continued

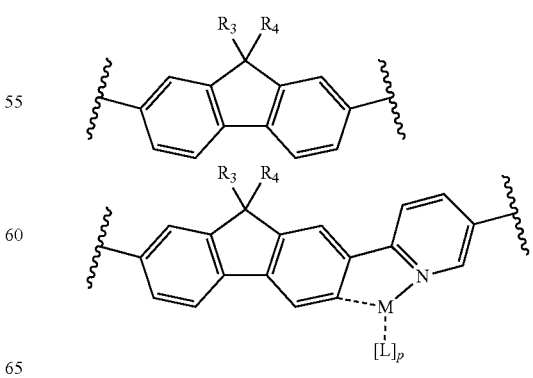

and wherein $R_3$ and $R_4$ are each groups $R_1$ and $R_2$ as defined in claim 1, or are each independently hydrogen or a group:

—$X^1$-$Q^1$ wherein $X^1$ is selected from (1-30C)alkylene, (2-30C)alkenylene, (2-30C)alkynylene, —[(CH$_2$)$_2$—O]$_n$—, —[O—(CH$_2$)$_2$]$_n$—, —[O—CH$_2$MeCH$_2$]$_n$, —[CH$_2$MeCH$_2$—O]$_n$—, [O—Si(R$_z$)$_2$]$_n$— wherein R$_z$ is (1-4C)alkyl and n is 1 to 30, and —[(CH$_2$)$_n$—(CF$_2$)$_{m'}$]— wherein n' is 0-20 and m' is 1 to 30;

$Q^1$ is a terminal group selected from the following substituents, or a salt thereof: hydrogen, halogen, methyl, hydroxyl, carboxy, (1-4C)alkoxycarbonyl, amino, —CH=CH$_2$, —C≡CH, —SH, biotin, streptavidin, —CF$_3$, —OSO$_3$H, —SO$_3$H, —OPO$_2$OH, zwitterions, and a polymerisable group selected from silane, siloxane, acrylate, epoxy, styrene;

M is a metal selected from Ir, Pt, Rh, Re, Ru, Os, Cr, Cu, Pd and Au;

L is a ligand independently selected from halo, (1-30C) hydrocarbyl optionally comprising one or more heteroatoms selected from N, O, S, Si, Ge, As or P, or an aryl or heteroaryl group optionally substituted with one or more substituents selected from (1-4C)alkyl, halo, aryl or heteroaryl;

X is a heteroatom selected from N, O, P, S, Si, Ge, As or Se;

p is 1 to 4;

and with the proviso that, in at least one monomer of formula V or VI, $Q^1$ is or comprises a group selected from amino, carboxy, hydroxyl, halogen, vinyl, alkenyl, alkynyl, carbonyl, thiol, -biotin or streptavidin, —CF$_3$, —OSO$_3$H, —SO$_3$H, —OPO$_2$OH, and zwitterions.

5. The conjugate of claim 4, wherein $A_1$ and $A_2$ are independently absent or selected from any one of the following moieties:

wherein $R_3$, $R_4$, M, L and p are as defined in claim 4.

6. The conjugate of claim 4, wherein $A_1$ or $A_2$ is absent; or wherein both $A_1$ and $A_2$ are absent.

7. The conjugate of claim 4, wherein when present

X and $X^1$ are independently selected from the group consisting of (1-30C)alkylene, (2-30C)alkenylene, (2-30C)alkynylene, —[(CH$_2$)$_m$(CF$_2$)$_n$]—, —[(CH$_2$)$_2$—O]$_n$—, —[O—(CH$_2$)$_2$]$_n$—, —[O—CHMeCH$_2$]$_n$—, —[CHMeCH$_2$—O]$_n$—, and —[O—Si(R$_z$)$_2$]$_n$—, wherein $R_z$ is methyl, n is 1 to 30, and m is 0 to 30;

Q and $Q^1$ are independently a terminal group selected from the following substituents, or a salt thereof: hydrogen, halogen, methyl, hydroxyl, carboxy, (1-4C) alkoxycarbonyl, amino, —CH═CH$_2$, —C≡CH, —SH, biotin, streptavidin, —CF$_3$, OSO$_3$H, —SO$_3$H, —OPO$_2$OH, zwitterions, and a polymerisable group selected from acrylates, epoxy and styrene;

M is a metal selected from Ir, Pt, Rh, Re, Ru, Os, Cr, Cu, Pd and Au;

L is a ligand independently selected from the group consisting of halo, (1-30C)hydrocarbyl optionally comprising one or more heteroatoms selected from N, O, S, Si or P, or an aryl or heteroaryl group optionally substituted with one or more substituents selected from (1-4C)alkyl, halo, aryl or heteroaryl; and p is 1 to 4;

and with the proviso that at least one group Q and/or $Q^1$ is or comprises a group selected from amino, carboxy, hydroxyl, halogen, vinyl, alkenyl, alkynyl, carbonyl, thiol, biotin, and streptavidin.

8. The conjugate of claim 1, wherein the π-conjugated cross-linked polymer comprises 80-99.9 mol. % of π-conjugated monomers selected from any of the following structures:

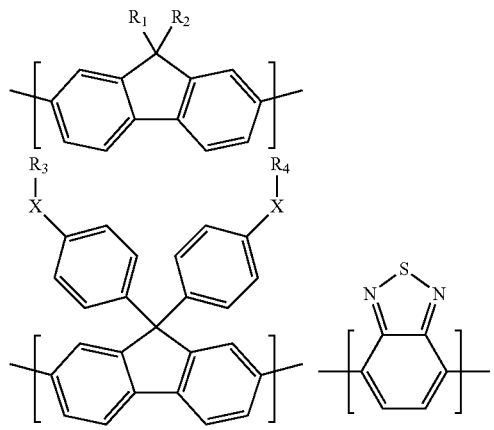

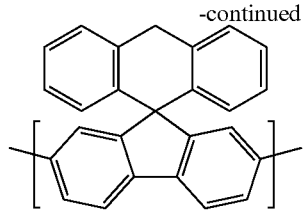

wherein $R_1$, $R_2$, $R_3$ and $R_4$ are each independently selected from: —(CH$_2$)$_n$R$_{50}$ and —(CH$_2$CH$_2$O)$_n$R$_{50}$; wherein n is 1 to 15 and $R_{50}$ is selected from —H, (1-15C)alkyl, —CO$_2$H, —CO$_2$(1-6C)alkyl, —CO$_2$Na, —CH═CH$_2$, —OC(O)-(biotin) and —OSO$_3$Na; and X is O.

9. The conjugate of claim 8, wherein $R_1$ and $R_2$ are both selected from —(CH$_2$)$_7$CH$_3$, —(CH$_2$)$_5$CO$_2$Et, —(CH$_2$)$_{10}$CO$_2$H, —(CH$_2$)$_4$CH═CH$_2$, —(CH$_2$)$_{11}$OSO$_3$Na, —(CH$_2$)$_5$CO$_2$Et, —(CH$_2$)$_{10}$CO$_2$Na, —(CH$_2$CH$_2$O)$_3$CH$_3$, —(CH$_2$)$_{11}$OC(O)-(biotin) and —(CH$_2$CH$_2$O)$_{12}$CH$_3$; and $R_3$ and $R_4$ are selected from 2-ethylhexyl, —(CH$_2$)$_{11}$OSO$_3$Na, —(CH$_2$CH$_2$O)$_n$CH$_3$ and —(CH$_2$)$_{10}$CO$_2$Na.

10. A method of forming a conjugate of claim 1, the method comprising the steps of:
(i) forming the nanoparticles by emulsion polymerisation, mini-emulsion polymerisation or dispersion polymerisation techniques to provide an aqueous suspension of nanoparticles;
(ii) reacting the nanoparticles with the drug molecule, biological molecule or cell so as to form an aqueous suspension of the conjugate.

11. The method of claim 10, wherein the nanoparticles are formed by a cross-coupling polymerisation reaction.

12. The method of claim 10, further comprising the step of purifying the aqueous suspension of nanoparticles.

13. The method of claim 12, wherein the aqueous suspension of nanoparticles is purified by contacting the aqueous suspension of nanoparticles with at least one organic solvent.

14. The method of claim 13, wherein the at least one organic solvent is either selected from the group consisting of polar and non-polar solvents; or is methanol or propanol.

15. The conjugate of claim 1, wherein the π-conjugated monomers comprise monomers having the following structure:

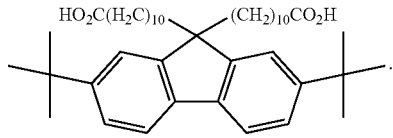

* * * * *